(12) United States Patent
Sikuljak et al.

(10) Patent No.: US 10,201,157 B2
(45) Date of Patent: Feb. 12, 2019

(54) USE OF PESTICIDAL ACTIVE CARBOXAMIDE DERIVATIVE IN SOIL AND SEED APPLICATION AND TREATMENT METHODS

(71) Applicant: BASF Agrochemical Products B.V., Arnhem (NL)

(72) Inventors: Tatjana Sikuljak, Mannheim (DE); Markus Gewehr, Hemsbach (DE); Anil Menon, Apex, NC (US)

(73) Assignee: BASF AGROCHEMICAL PRODUCTS B.V., Arnhem (NL)

( * ) Notice: Subject to any disclaimer, the term of this patent is extended or adjusted under 35 U.S.C. 154(b) by 0 days.

(21) Appl. No.: 15/029,737

(22) PCT Filed: Oct. 16, 2014

(86) PCT No.: PCT/EP2014/072192
§ 371 (c)(1),
(2) Date: Apr. 15, 2016

(87) PCT Pub. No.: WO2015/055757
PCT Pub. Date: Apr. 23, 2015

(65) Prior Publication Data
US 2016/0262386 A1    Sep. 15, 2016

Related U.S. Application Data

(60) Provisional application No. 61/906,441, filed on Nov. 20, 2013, provisional application No. 61/892,502, filed on Oct. 18, 2013.

(51) Int. Cl.
| | | |
|---|---|---|
| *A01N 37/22* | (2006.01) | |
| *A01N 43/56* | (2006.01) | |
| *A01N 25/02* | (2006.01) | |
| *A01N 37/46* | (2006.01) | |
| *A01N 43/22* | (2006.01) | |
| *A01N 43/653* | (2006.01) | |
| *A01N 43/88* | (2006.01) | |
| *A01N 43/90* | (2006.01) | |
| *A01N 47/30* | (2006.01) | |
| *A01N 51/00* | (2006.01) | |
| *A01N 57/16* | (2006.01) | |
| *A01N 57/28* | (2006.01) | |
| *A01N 63/02* | (2006.01) | |

(52) U.S. Cl.
CPC ............. *A01N 37/22* (2013.01); *A01N 37/46* (2013.01); *A01N 43/22* (2013.01); *A01N 43/56* (2013.01); *A01N 43/653* (2013.01); *A01N 43/88* (2013.01); *A01N 43/90* (2013.01); *A01N 47/30* (2013.01); *A01N 51/00* (2013.01); *A01N 57/16* (2013.01); *A01N 57/28* (2013.01); *A01N 63/02* (2013.01)

(58) Field of Classification Search
CPC combination set(s) only.
See application file for complete search history.

(56) References Cited

U.S. PATENT DOCUMENTS

| | | | | |
|---|---|---|---|---|
| 2008/0153707 A1* | 6/2008 | Gewehr | ............... | C07D 231/14 504/282 |
| 2008/0293798 A1* | 11/2008 | Dietz | ..................... | A01N 43/56 514/407 |
| 2011/0137068 A1* | 6/2011 | Aoki | ..................... | A01N 37/46 560/43 |
| 2015/0208655 A1* | 7/2015 | El Qacemi | ........... | G06Q 30/018 514/340 |

FOREIGN PATENT DOCUMENTS

| | | | |
|---|---|---|---|
| EP | 2 319 830 | 5/2011 | |
| EP | 2 529 620 | 12/2012 | |
| JP | 2011157294 | 8/2011 | |
| JP | 2011157295 | 8/2011 | |
| JP | 2011157296 | 8/2011 | |
| WO | WO 2005/073165 | 8/2005 | |
| WO | WO 2007/013150 | 2/2007 | |
| WO | WO 2007/128756 A1 * | 11/2007 | ............. A01N 37/22 |
| WO | WO 2015/055755 | 10/2014 | |
| WO | WO 2015/055752 | 4/2015 | |

OTHER PUBLICATIONS

International Search Report dated Jan. 8, 2015, prepared in International Application No. PCT/EP2014/072192.
International Preliminary Report on Patentability dated Jan. 25, 2016, prepared in International Application No. PCT/EP2014/072192.

* cited by examiner

*Primary Examiner* — John Pak
(74) *Attorney, Agent, or Firm* — Brinks Gilson & Lione

(57) ABSTRACT

The present invention relates to agricultural methods and the use of an insecticidal active carboxamide derivative in seed treatment and soil application methods.

The insecticidal carboxamide derivative is highly suitable alone or in combination with other active agricultural ingredients for controlling animal pests such as insects and/or spider mites and/or nematodes by treating the soil/growth substrate by drenching or drip application or dipping or soil injection.

17 Claims, No Drawings

USE OF PESTICIDAL ACTIVE CARBOXAMIDE DERIVATIVE IN SOIL AND SEED APPLICATION AND TREATMENT METHODS

This application is a National Stage application of International Application No. PCT/EP2014/072192, filed Oct. 16, 2014, which claims the benefit of U.S. Provisional Application No. 61/892,502, filed Oct. 18, 2013, and U.S. Provisional Application No. 61/906,441, filed Nov. 20, 2013.

The present invention relates to the use of carboxamide derivatives for controlling arthropods, especially insects and arachnids, (spider) mites and/or nematodes.

The present invention relates to the use of a carboxamide derivative for controlling soil living pests by seed treatment methods.

The present invention relates to the use of carboxamide derivatives for controlling soil living pests by soil application methods such as drenching, drip application, in-furrow application, dip application or soil injection or by seed treatment.

Invertebrate pests, arthropods and nematodes, and in particular insects and arachnids, destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests such as insects, arachnids and nematodes.

Especially soil-living pests, arthropod pests, including soil-living insects and arachnids, and especially spider mites, and nematodes, are often controlled and combated by applying an effective amount of a suitable pesticide compound to the soil, e.g. by drenching, drip application, dip application or soil injection. The pesticidal compounds may further be applied as a solid or liquid composition, e.g. such as a dust or granule formulation comprising an inert carrier, e.g. such as clay.

Methods of soil application can suffer from several problems. Pesticidal compounds are not always especially suitable for being applied by different soil application methods such as by drenching, drip application, dip application or soil injection. Their pesticidal activity may be affected in some cases.

It is therefore an object of the present invention to provide compounds having a good pesticidal activity and a good applicability in techniques of soil treatment against a large number of different invertebrate pests, especially against soil-living pests, which are difficult to control.

Some soil-applied pesticides compositions may also have potential for leaching. Therefore, care must be taken to minimize both surface and ground water contamination. Moreover, the effectiveness of the pesticide may vary depending on environmental conditions e.g. properly timed rain is needed for the successful functioning of the chemistry in the soil, but too much rain may reduce the effectiveness and may cause leaching.

It is therefore also an object of the present invention to provide compositions which are suitable for combating soil-living pests and which overcome the problems associated with the known techniques. In particular the compositions should be applicable easily and provide a long-lasting action on soil-living pests. Moreover, environmental conditions should not have an adverse effect on the effectiveness of the pesticide.

Soil application methods are considered as different techniques of applying pesticidal compounds directly or indirectly to the soil and/or ground, such as drip applications or drip irrigations (onto the soil), or soil injection, further methods of drenching the soil. Further known soil application methods are in-furrow and T-band applications.

Furthermore, object of the present inventions are methods of application by dipping roots, tubers or bulbs (referred to as dip application), by hydroponic systems or also by seed treatment.

Another of the problems the farmer is faced with in this context is, that seeds and plant roots and shoots are constantly threatened by foliar and soil insects and other pests.

Thus a further difficulty in relation to the use of such seed protection pesticides is that the repeated and exclusive application of an individual pesticidal compound leads also here in many cases to a rapid selection of soil pests, which have developed natural or adapted resistance against the active compound in question. Therefore there is a need for seed protection agents that help prevent or overcome resistance.

It is therefore a further object of the present invention to provide compounds which solve the problems of protection of the protection of seeds and growing plants, reducing the dosage rate, enhancing the spectrum of activity and/or to manage pest resistance.

The present invention therefore also provides methods for the protection of to plant proparagation material, especially seeds, from soil insects and of the resulting plant's roots and shoots from soil and foliar insects.

The invention also relates to plant proparagation material, especially seeds, which are protected from soil and foliar insects.

It is therefore especially an object of the present invention to provide methods of application, which are suitable for combating soil-living pests Surprisingly, it has now been found that carboxamide compounds of formula (I) of the present invention

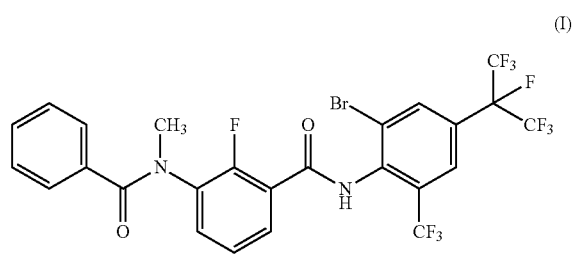 [SMILES: CN(C(=O)c1ccccc1)c1cccc(C(=O)Nc2c(Br)cc(C(F)(C(F)(F)F)C(F)(F)F)cc2C(F)(F)F)c1F]

(I)

or the tautomers, enantiomers, diastereomers or salts thereof, is highly suitable for methods for controlling and/or combating insects, acarids and/or nematodes, and especially spider mites, by soil application and seed treatment methods.

It has further been found, that mixtures of the compound of formula (I) with other agriculturally active ingredients, such as insecticides or fungicides, are especially suitable for the purpose of seed treatment.

Carboxamide derivatives showing generally pesticidal activity have been described previously. WO200573165 and WO2010018714 describe carboxamide compounds, their preparation and their use as pest control agents. WO2007013150, JP2011-157294, JP2011-157295 and JP2011-157296 describe mixtures of carboxamides with other active ingredients. The application of some carboxamide derivatives on vegetable seeds has been described in JP2011-157295.

However, their surprisingly excellent applicability for soil application techniques as well as in seed treatment methods, and their extraordinary activity against soil-living pests, especially in combination with other agricultural active ingredients have not been described previously.

Formulations

The invention also relates to agrochemical compositions suitable for applying in soil treatment methods comprising an auxiliary and at least the compound of formula (I) according to the invention.

An agrochemical composition comprises a pesticidally effective amount of a compound of formula (I). The term "effective amount" denotes an amount of the composition or of the compounds I, which is sufficient for controlling harmful pests on cultivated plants or in the protection of materials and which does not result in a substantial damage to the treated plants. Such an amount can vary in a broad range and is dependent on various factors, such as the animal pests species to be controlled, the treated cultivated plant or material, the climatic conditions and the specific compound I used.

The compounds of formula (I), their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclo¬hexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl¬naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkyl-polyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying compound I and compositions thereof, respectively, on to plant propagation material, especially seeds include dressing, coating, pelleting, dusting, soaking and infurrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

Applications

The present invention relates to the methods by use on natural substrates (soil) or artificial (growth) substrates (e.g. rock wool, glass wool, quartz sand, gravel, expanded clay, vermiculite), in the open or in closed systems (e.g. greenhouses or under film mulch) and in annual crops (such as vegetables, spices, ornamentals) or perennial crops (such as citrus plants, fruits, tropical crops, spices, nuts, grapevines, conifers and ornamentals).

It has now been found that the problems associated with combating soil-living pests by pesticide treatment of the soil can be overcome by such application methods using compounds of the present invention.

The animal pest, i.e. the insects, arachnids and nematodes, the plant, the water or the soil in which the plant is growing can be contacted with the present compounds of formula I or composition(s) containing them by any application method known in the art. As such, "contacting" includes both direct contact (applying the compounds/compositions directly on the animal pest or plant) and indirect contact (applying the compounds/compositions to the locus of the animal pest or plant). When the plant is contacted, typically the tuber, bulbs or roots of the plant are contacted. The compounds of formula (I) may further be applied to other parts of the plant, such as leaves in case of of foliar application, or to plant propagation material such as seeds in the case of seed treatment.

The compounds of formula I or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

Thus, as with regards to the use and for the purpose of the present invention, vegetables are to be understood as meaning for example fruiting vegetables and inflorescences as vegetables, i.e. bell peppers, chillies, tomatoes, aubergines, cucumbers, pumpkins, courgettes, broad beans, climbing and dwarf beans, peas, artichokes and maize. Further also leafy vegetables like head-forming lettuce, chicory, endives, various types of cress, of rocket, lamb's lettuce, iceberg lettuce, leeks, spinach and chard. Furthermore tuber vegetables, root vegetables and stem vegetables, like celeriac/celery, beetroot, carrots, radish, horseradish, scorzonera, asparagus, beet for human consumption, palm hearts and bamboo shoots. Further also bulb vegetables like onions, leeks, fennel and garlic. *Brassica* vegetables such as cauliflower, broccoli, kohlrabi, red cabbage, white cabbage, curly kale, Savoy cabbage, Brussels sprouts and Chinese cabbage are also vegetable in the sense of the present application.

Regarding the use and for the purpose of the present invention, perennial crops are to be understood as meaning citrus, for example, oranges, grapefruits, tangerines, lemons, limes, Seville oranges, cumquats and satsumas. Also pome fruit such as, for example, apples, pears and quinces, and stone fruit such as, for example, peaches, nectarines, cherries, plums, quetsch, apricots. Further grapevines, hops, olives, tea and tropical crops such as, for example, mangoes, papayas, figs, pineapples, dates, bananas, durians, kaki fruit, coconuts, cacao, coffee, avocados lychees, maracujas, and. guavas. Furthermore soft fruit such as, for example, currants, gooseberries, raspberries, blackberries, blueberries, strawberries, cranberries, kiwi fruit and American cranberries. Almonds and nuts such as, for example, hazelnuts, walnuts, pistachios, cashew nuts, para nuts, pecan nuts, butternuts, chestnuts, hickory nuts, macadamia nuts and peanuts are also fruits in the sense of the present invention.

As with regard to the use and for the purpose of the present invention, ornamentals are understood as meaning annual and perennial plants, for example cut flowers such as, for example, roses, carnations, *gerbera*, lilies, marguerites, chrysanthemums, tulips, *narcissus*, anemones, poppies, amaryllis, dahlias, azaleas, hibiscus, but also for example border plants, pot plants and perennials such as, for example, roses, *Tagetes*, violas, geraniums, fuchsias, hibiscus, chrysanthemum, busy lizzie, cyclamen, African violet, sunflowers, begonias.

Furthermore for example also bushes and conifers such as, for example, *ficus, rhododendron*, firs, spruces, pines, yews, juniper, umbrella pines, *oleander.*

As regards the use, spices are understood as meaning annual and perennial plants such as, for example, aniseed, chilli pepper, paprika, pepper, vanilla, marjoram, thyme, cloves, juniper berries, cinnamon, tarragon, coriander, saffron, ginger.

Furthermore the compounds of the present invention and the compositions comprising them are particularly important in the control of a multitude of insects on various cultivated plants, such as cereal and oil crops, for example seed of durum and other wheat, barley, oats, rye, maize (fodder maize and sugar maize/sweet and field corn), soybeans, oil crops, crucifers, cotton, bananas, rice, oilseed rape, turnip rape, sugarbeet, fodder beet, eggplants, potatoes, grass, lawn, turf, fodder grass, sugar cane or tobacco.

The compounds of the invention can also be applied preventively to places at which occurrence of the pests is expected.

"Locus" means a habitat, breeding ground, plant, seed, soil, area, material or environment in which a pest or parasite is growing or may grow.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8., Protein Eng Des Sel. 2004 January; 17(1):57-66, Nat Protoc. 2007; 2(5):1225-35, Curr Opin Chem Biol. 2006 October; 10(5):487-91. Epub 2006 Aug. 28., Biomaterials. 2001 March; 22(5):405-17, Bioconjug Chem. 2005 January-February; 16(1):113-21).

The term "cultivated plants" is to be understood also including plants that have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as ä-endotoxins, e.g. CrylA(b), CrylA(c), CrylF, CrylF(a2), CryllA(b), CrylllA, CrylllB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are disclosed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against Phytophthora infestans derived from the mexican wild potato Solanum bulbocastanum) or T4-lyso-zym (e.g. potato cultivars capable of synthesizing these proteins with increased resistance against bacteria such as Erwinia amylvora). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

As mentioned further above, soil application methods include among other known techniques in-furrow and T-band applications.

The active compound can be applied as granular as T-Band or In-furrow treatments. Granular or liquid T-Band applications are placed in front of the furrow closure wheels using plastic diffusers. In general, the band coverage pattern is approximately a couple of inches wide over an open furrow.

In furrow treatments are directed into the open furrow using plastic tubing.

Liquid formulations are applied as T-band over an open furrow.

For example, seeds are planted using cone seeders and drop nozzles are positioned over the seed furrow. The boom can be moved up or down to change band width. A flat fan nozzle can also be used: perpendicular to the row for bands and parallel to the row for in-furrow. The boom position is between the furrow opener and the press wheel which directs some (band) or all (in-furrow) of the spray into the furrow before furrow closure. When used in in-furrow applications, the active compound(s) can be applied simultaneously with the planting of the seeds, e.g. as granular, liquid or another formulation type. Alternatively, the nozzles can also be positioned behind the press wheel for an entirely surface spray of the liquid formulation comprising the active compound(s).

The compounds of formula I are also suitable for the treatment of seeds in order to protect the seed from insect pest, in particular from soil-living insect pests and the resulting plant's roots and shoots against soil pests and foliar insects.

The compounds of formula I are particularly useful for the protection of the seed from soil pests and the resulting plants roots and shoots against soil pests and foliar insects. The protection of the resulting plants roots and shoots is preferred. More preferred is the protection of resulting plants shoots from piercing and sucking insects, wherein the protection from aphids is most preferred.

The present invention therefore comprises a method for the protection of seeds from insects, in particular from soil insects and of the seedling's roots and shoots from insects, in particular from soil and foliar insects, said method comprising contacting the seeds before sowing and/or after pregermination with a compound of the general formula I or a salt thereof. Particularly preferred is a method, wherein the plants roots and shoots are protected, more preferably a method, wherein the plants shoots are protected form piercing and sucking insects, most preferably aa method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting. The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of formula I for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants. Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the formula I, or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Pests and Fungi

The invention in particular relates to soil application methods for combating soil-living arthropod pests, and nematode pests, which comprises applying to the soil a pesticidally effective amount of a compound of the present invention.

The term "soil-living" means that the habitat, breeding ground, area or environment in which a pest or parasite is growing or may grow is the soil.

The use of the compounds according to the present invention extends to a wide range of different animal pests, especially soil living pests. These include but are not limited to, the following families:

Insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouli-* ana, *Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, LithocolletIS blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis plleriana, Spodoptera frugiperda, Spodoptera littoralis, Spodoptera litura, Thaumatopoea pityocampa, Tortrix viridana, Trichoplusia ni, Tuta absoluta,* and *Zeiraphera canadensis,* beetles (*Coleoptera*), for example *Agrilus sinuatus, Agriotes lineatus, Agriotes obscurus, Amphimallus solstitialis, Anisandrus dispar, Anoplophora glabripensis, Anthonomus grandis, Anthonomus pomorum, Aphthona euphoridae, Athous haemorrhoidalis, Atomaria linearis, Blastophagus piniperda, Blitophaga undata, Byctiscus betulae, Cassida nebulosa, Cerotoma trifurcata, Cetonia aurata, Ceuthorrhynchus assimilis, Ceuthorrhynchus nap, Chaetocnema tibialis, Conoderus vespertinus, Crioceris asparagi, Ctenicera ssp., Diabrotica longicornis, Diabrotica semipunctata, Diabrotica 12-punctata Diabrotica speciosa, Diabrotica virgifera, Eplachna varivestis, Epitrix hirtipennis, Hylobius abietis, Hypera brunneipennis, Hypera postica, Ips typographus, Lema bllineata, Lema melanopus, Leptinotarsa decemlineata, Limonius californicus, Lissorhoptrus olyzophllus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga sp., Phyllopertha horticola, Phyllotreta nemorum, Phyllotreta striolata, Popilia japonica, Sitona lineatus* and, flies, mosquitoes (*Diptera*), e.g. *Ceratitis capitata, Contarinia sorghicola Dacus cucurbitae, Dacus oleae, Dasineura brassicae, Della antique, Della coarctata, Della platura, Della radicum, Liriomyza sativae, Liriomyza trifolii, Oscinella frit, Pegomya hysocyami, Phorbia antiqua, Phorbia brassicae, Phorbia coarctata, Psila rosae, Psorophora discolor, Rhagoietis cerasi, Rhagoletis pomonella, Tipula oleracea,* and *Tipula paludosa* thrips (*Thysanoptera*), e.g. *Dichromothrips corbetti, Dichromothrips* ssp., *Frankliniella fusca, Frankliniella occidentalis, Frankliniella tritia, Scirtothnps citri, Thrips oryzae, Thrips palmi* and *Thrips tabaci,* termites (*Isoptera*), e.g. *Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis,* and *Coptotermes formosanus,* bugs, aphids, leafhoppers, whiteflies, scale insects, cicadas (*Hemiptera*), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onothychis, Adelges laricis, Aphidula nasturtii, Aphis fabae, Aphis forbesi, Aphis pomi, Aphis gossypil, Aphis grossulariae, Aphis schneiden, Aphis spiraecola, Aphis sambuci, Acyrthosiphon pisum, Aulacorthum solani, Bemisia argentifolil Brachycaudus cardui, Brachycaudus helichrysi, Brachycaudus persicae, Brachycaudus prunicola, Brevicolyne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolam, Dysaphlis plantaginea, Dysaphis pyri, Empoasca fabae, EuschLstos heros, Euschistos servus, Halyomorpha halys, Hyalopterus pruni, Hyperomyzus lactucae, Macrosiphum avenae, Macrosiphum euphorbiae, Macrosiphon rosae, megacopta criberia, Megoura viciae, Melanaphis pyrarius, Metopolophium dirhodum, Myzus persicae, Myzus ascalonicus, Myzus cerasi, Myzus varians, Nasonovia ribis-nigri, Nezara viridula, Nilaparvata lugens, Pemphigus bursarlus, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphlis mall, Schizaphlis graminum, Schizoneura lanuginosa, Sitobion avenae, Trialeurodes vaporariorum, Toxoptera aurantiiand, Viteus vitifolli, Cimex lectularius, Cimex hemipterus, Reduvius senilis, Triatoma* spp., and *Arllus critatus.* ants, bees, wasps, sawflies (*Hymenoptera*), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, SolenopsIS xyloni, Pogonomyrmex barbatus, Pogonomyrmex californicus, Pheidole megacephala, Dasymutilla occidentalis, Polistes rubiginosa, Camponotus floridanus,* and *Linepithema humile,* crickets, grasshoppers, locusts (*Orthoptera*), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina,*

Arachnoidea, such as arachnids (*Acarina*), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnim, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni;* Tarsonemidae spp. such as *Phytonemus pallidus* and *Polyphagotarsonemus latus;* Tenuipalpidae spp. such as *Brevipalpus phoenicis;* Tetranychidae spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis,* Araneida, e.g. *Latrodectus mactans,* and *Loxosceles reclusa,*

Other animal pests to be controlled and combated by the methods of the present invention are:

From the family of the Pemphigidae: *Eriosoma* spp., *Pemphigus* spp., *Anuraphis* spp., *Brachycaudus* spp., in crops such as, for example, pome fruit, conifers, vegetables and ornamentals.

From the psyllid family (Psyllidae: *Psylla* spp., *Paratrioza* spp., *Trioza* spp., in crops such as, for example, citrus, vegetables, potatoes, pome fruit.

From the scale insect family (Coccidae: *Ceroplastes* spp., *Drosicha* spp. *Pulvinana* spp., *Protopuhninaria* spp., *Saissetia* spp., *Coccus* spp., in perennial crops such as, for example, citrus, grapevines, tea, pome and stone fruit, tropical crops, ornamentals, conifers, but also vegetables.

From the family of the Diaspididae: *Quadraspidiotus* spp., *Aonidiella* spp., *Lepidosaphes* spp., *Aspidiotus* spp., *Aspis* spp., *Diaspis* spp., *Parlatona* spp., *Pseudaulacaspis* spp., *Unaspis* spp., *Pinnaspis* spp., *Selenaspidus* spp., in crops such as, for example, citrus, tea, ornamentals, conifers, pome and stone fruit, grapevines, tropical crops.

From the family of the Pseudococcidae: *Pericerga*, *Pseudococcus* spp., *Planococcus* spp., *Phenacoccus* spp., *Dysmicoccus* spp., in crops such as, for example, citrus, pome and stone fruit, tea, grapevines, vegetables, ornamentals, conifers, spices and tropical crops.

Furthermore from the family of the Aleyrodidae: *Bemisia argentifolii, Bemisia tabaci, Trialeurodes vaporariorum, Aleurothrixus floccosus, Aleurodes* spp., *Dialeurodes* spp., *Parabemisia myricae* in crops such as, for example, vegetables, melons, potatoes, tobacco, soft fruit, citrus, ornamentals, conifers, cotton, potatoes and tropical crops.

Furthermore from the family of the Aphidae:

*Myzus* spp. in tobacco, stone fruit, pome fruit, soft fruit, *Brassica* vegetables, fruiting vegetables, leafy vegetables, tuber and root vegetables, melons, potatoes, spices, ornamentals and conifers.

*Aphis* spp. in cotton, tobacco, citrus, melons, beet, soft fruit, oilseed rape, fruiting vegetables, leafy vegetables, *Brassica* vegetables, tuber and root vegetables, ornamentals, potatoes, pumpkins, spices. *Rhodobium porosum* in strawberries,

*Nasonovia ribisnigri* in leafy vegetables,

*Macrosiphum* spp. in ornamentals, cereals, potatoes, leafy vegetables, *Brassica* vegetables and fruiting vegetables, strawberries, *Phorodon humuli* in hops, *Toxoptera* spp. in citrus, stone fruit, almonds, nuts, cereals, spices,

*Aulacorthum* spp. in citrus, potatoes, fruiting vegetables and leafy vegetables.

Furthermore the following from the family of the Tetranychidae:

*Tetranychus* spp., *Brevipalpus* spp., *Panonychus* spp., *Oligonycbus* spp., *Eotetranychus* spp., *Bryobia* spp. in crops such as, for example, vegetables, ornamentals, spices, conifers, citrus, stone and pome fruit, grapevines, cotton, soft fruit, melons, potatoes.

The following from the family of the Tarsonemidae: *Hermitarsonernus batus, Stenotarsonemus* spp., *Polyphagotarsonemus* spp., *Stenotarsonemus spinki* in crops such as, for example, vegetables, ornamentals, spices, conifers, tea, citrus, melons.

Furthermore the following from the *thrips* family (Thripidae): *Anaphothrips* spp., *Baliothrips* spp., *Caliothrips* spp., *Frankliruella* spp., *Heliothrips* spp., *Hercrnothrips* spp., *Rhipiphorothrips* spp., *Scirtothrips* spp., *Selenothrips* spp. and *Thrips* spp., in crops such as, for example, fruit, cotton, grapevines, soft fruit, vegetables, melons, ornamentals, spices, conifers, tropical crops, tea.

Also the following from the whitefly family (Agromyzidae): *Liriomyza* spp., *Pegomya* spp. in crops such as, for example, vegetables, melons, potatoes and ornamentals.

Also the following from the foliar nematode family (Aphelenchoididae), for example *Aphelenchoides ritzemabosi, A. fragariae, A. besseyi, A. blastophthorus* in crops such as soft fruits and ornamentals.

The methods of the present invention are applied to control and combat arachnids, especially the following ones from the family of the Tetranychidae:

*Tetranychus* spp., *Brevipalpus* spp., *Panonychus* spp., *Oligonycbus* spp., *Eotetranychus* spp. and *Bryobia* spp.

When combined with fungicidal active ingredients in the methods according to the present invention, the mixtures of compound of the formula I are also especially suitable for efficiently combating phytopathogenic fungi.

These mixtures have excellent activity against a broad spectrum of phytopathogenic fungi *Ascomycetes, Basidiomycetes, Deuteromycetes* and *Peronosporomycetes* (syn. *Oomycetes*). Some of them are systemically effective and can be employed in crop protection as foliar fungicides, as fungicides for seed dressing and as soil fungicides. They can also be used for treating seed.

They are particularly important in the control of a multitude of fungi on various cultivated plants, such as wheat, rye, barley, oats, rice, corn, lawns, bananas, cotton, soybean, coffee, sugar cane, grapevines, fruits and ornamental plants, and vegetables such as cucumbers, beans, tomatoes, potatoes and cucurbits, and on the seeds of these plants.

They are especially suitable for controlling the following plant diseases:

*Albugo* spp. (white rust) on ornamentals, vegetables (e.g. *A. candida*) and sunflowers (e.g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. altemata*), tomatoes (e.g. *A. solani* or *A. altemata*) and wheat; *Aphanomyces* spp. on sugar beets and vegetables; *Ascochyta* spp. on cereals and vegetables, e.g. *A. tritici*(anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botlyotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes* black dot), beans (e.g. *C. lindemuthianum*) and soybeans (e.g. *C. truncatum* or *C. gloeosporioides*); *Corticium* spp., e.g. *C. sasakii* (sheath blight) on rice; *Corynespora cassii-*

*cola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*: Black Foot Disease) and ornamentals; *Dematophora* (teleomorph: *Roseloinia*) *necatrix* (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophllum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (Eutypa canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* (f. sp. *glycines* now syn. *F. virguliforme*) and *F. tucumaniae* and *F. brasiliense* each causing sudden death syndrome on soybeans, and *F. verticillioides* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grainstaining connplex on rice; *Guignardia bidwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemlleia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. taxa*, *M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria Septoria* blotch) on wheat or *M. fifiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. melbomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans* late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or, 'rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyriculana* spp., e.g. *P. olyzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collo-cygni*(Rannularia leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. sclerotiorum*); *Septoria* spp. on various plants, e.g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. Pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

Mixtures and Preferred Compound Combinations

Mixtures and preferred combinations of the carboxamid compound of formula (I) with other active ingredients for soil application and seed treatment methods are described in the following.

As mentioned further above, in one embodiment of the invention, the pesticidal compound of formula (I) can be combined and used in mixture with at least another active compound II applied in agriculture, such as another insecticidal active, a fungicidal active or a biopesticide. In another embodiment of the invention, the pesticidal compound of formula (I) can be combined and used in mixture with more than one other active compound applied in agriculture. Thus the pesticidal compound of formula (I) can be combined and used in mixture with more than one other insecticide and/or with more than one fungicide.

For example the pesticidal compound of formula (I) can be combined and used in mixture with one, two three or four other agriculturally active compound selected from fungicides and/or insecticides.

Preferably such other compounds are active against said soil-living arthropod pests or soilborne phytopathogenic fungi. A skilled person is familiar with such compounds and knows which connpounds are active against a specific target organism.

The following lists M of pesticides and F of fungicides together with which the compounds according to the invention can be used and with which also potential synergistic effects might be produced, are intended to illustrate the possible combinations, but not to impose any limitation:

The following list M of pesticides, grouped and numbered according the Mode of Action Classification of the Insecticide Resistance Action Committee (IRAC), together with which the compounds according to the invention can be used and with which potential synergistic effects might be produced, is intended to illustrate the possible combinations, but not to impose any limitation:

M.1 Acetylcholine esterase (AChE) inhibitors from the class of

M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathionmethyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as:

M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, betacyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of

M.4A neonicotinoids, for example acteamiprid, chlothianidin, cycloxaprid, dinotefuran, imidacloprid, nitenpyram, thiacloprid and thiamethoxam; or the compounds M.4A.2: (2E-)-1-[(6-Chloropyridin-3-yl)methyl]-N'-nitro-2-pentylidenehydrazinecarboxinnidamide; or M4.A.3: 1-[(6-Chloropyridin-3-yl)methyl]-7-methyl-8-nitro-5-propoxy-1,2,3,5,6,7-hexahydroimidazo[1,2-a]pyridine;

or from the class M.4B nicotine;

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as

M.7A juvenile hormone analogues as hydroprene, kinoprene and methoprene; or others as M.7B fenoxycarb or M.7C pyriproxyfen;

M.8 miscellaneous non-specific (multi-site) inhibitors, for example

M.8A alkyl halides as methyl bromide and other alkyl halides, or

M.8B chloropicrin, or M.8C sulfuryl fluoride, or M.8D borax, or M.8E tartar emetic;

M.9 Selective homopteran feeding blockers, for example

M.9B pymetrozine, or M.9C flonicamid;

M.10 Mite growth inhibitors, for example

M.10A clofentezine, hexythiazox and diflovidazin, or M.10B etoxazole;

M.11 Microbial disruptors of insect midgut membranes, for example *bacillus thuringiensis* or *bacillus sphaericus* and the insecticdal proteins they produce such as *bacillus thuringiensis* subsp. *israelensis, bacillus sphaericus, bacillus thuringiensis* subsp. *aizawai, bacillus thuringiensis* subsp. *kurstaki* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example

M.12A diafenthiuron, or

M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example

M.20A hydramethylnon, or M.20B acequinocyl, or M.20C fluacrypyrim;

M.21 Mitochondrial complex I electron transport inhibitors, for example

M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example

M.22A indoxacarb, or M.22B metaflumizone, or M.22B.1: 2-[2-(4-Cyanophenyl)-1-[3-(trifluoromethyl)phenyl]ethylidene]-N-[4-(difluoromethoxy)phenyl]-hydrazinecarboxamide or M.22B.2: N-(3-Chloro-2-methylphenyl)-2-[(4-chlorophenyl)[4-[methyl(methylsulfonyl)amino]phenyl]methylene]-hydrazinecarboxamide;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example

M.24A phosphine such as aluminium phosphide, calcium phosphide, phosphine or zinc phosphide, or M.24B cyanide;

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (Rynaxypyr®), cyantraniliprole (Cyazypyr®), or the phthalamide compounds M.28.1: (R)-3-Chlor-N1-{2-methyl-4-[1,2,2,2 tetrafluor-1-(trifluormethyl)ethyl]phenyl}-N2-(1-methyl-2-methylsulfonylethyl)phthalamid and M.28.2: (S)-3-Chlor-N1-{2-methyl-4-[1,2,2,2 tetrafluor-1-(trifluormethyl)ethyl]phenyl}-N2-(1-methyl-2-methylsulfonylethyl)phthalamid, or the compound M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from M.28.5a) to M.28.5l):

M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide;

M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide;

M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide;

M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5e) N-[4,6-dichloro-2-[diethyl-lambda-4-sulfanylidene)carbamoyl]-phenyl]-2-(3-chloro-2-pyridyl)-5-(difluoromethyl)pyrazole-3-carboxamide;

M.28.5f) N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5g) N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide;

M.28.5h) N-[4,6-dibromo-2-[diethyl-lambda-4-sulfanylidene)carbamoyl]-phenyl]-2-(3-chloro-2-pyridyl)-5-(trifluoromethyl)pyrazole-3-carboxamide;

M.28.5i) N-[2-(5-Amino-1,3,4-thiadiazol-2-yl)-4-chloro-6-methylphenyl]-3-bromo-1-(3-chloro-2-pyridinyl)-1H-pyrazole-5-carboxamide;

M.28.5j) 3-Chloro-1-(3-chloro-2-pyridinyl)-N-[2,4-dichloro-6-[[(1-cyano-1-methylethyl)amino]carbonyl]phenyl]-1H-pyrazole-5-carboxamide;

M.28.5k) 3-Bromo-N-[2,4-dichloro-6-(methylcarbamoyl)phenyl]-1-(3,5-dichloro-2-pyridyl)-1H-pyrazole-5-carboxamide;

M.28.5l) N-[4-Chloro-2-[[(1,1-dimethylethyl)amino]carbonyl]-6-methylphenyl]-1-(3-chloro-2-pyridinyl)-3-(fluoromethoxy)-1H-pyrazole-5-carboxamide;

or a compound selected from

M.28.6: N-(2-cyanopropan-2-yl)-N-(2,4-dimethylphenyl)-3-iodobenzene-1,2-dicarboxamide; or M.28.7: 3-Chloro-N-(2-cyanopropan-2-yl)-N-(2,4-dimethylphenyl)-benzene-1,2-dicarboxamide;

M.28.8a) 1-(3-Chloro-2-pyridinyl)-N-[4-cyano-2-methyl-6-[(methylamino)carbonyl]phenyl]-3-[[5-(trifluoromethyl)-2H-tetrazol-2-yl]methyl]-1H-pyrazole-5-carboxamide; or M.28.8b) 1-(3-Chloro-2-pyridinyl)-N-[4-cyano-2-methyl-6-[(methylamino)carbonyl]phenyl]-3-[[5-(trifluoromethyl)-1H-tetrazol-1-yl]methyl]-1H-pyrazole-5-carboxamide;

M.UN. insecticidal active compounds of unknown or uncertain mode of action, as for example afidopyropen, afoxolaner, azadirachtin, amidoflumet, benzoximate, bifenazate, bromopropylate, chinomethionat, cryolite, dicofol, flufenerim, flometoquin, fluensulfone, fluopyram, flupyradifurone, fluralaner, metoxadiazone, piperonyl butoxide, pyflubumide, pyridalyl, pyrifluquinazon, sulfoxaflor, tioxazafen, triflumezopyrim, or the compounds M.UN.3: 11-(4-chloro-2,6-dimethylphenyl)-12-hydroxy-1,4-dioxa-9-azadispiro[4.2.4.2]-tetradec-11-en-10-one, or the compound M.UN.4: 3-(4'-fluoro-2,4-dimethylbiphenyl-3-yl)-4-hydroxy-8-oxa-1-azaspiro[4.5]dec-3-en-2-one, or the compound M.UN.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *bacillus firmus* (Votivo, I-1582); or a compound selected from the group of M.UN.6, wherein the compound is selected from M.UN.6a) to M.UN.6k):

M.UN.6a) (E/Z)—N-[1-[(6-chloro-3-pyridyl)methyl]-2-pyridylidene]-2,2,2-trifluoro-acetamide;

M.UN.6b) (E/Z)—N-[1-[(6-chloro-5-fluoro-3-pyridyl)methyl]-2-pyridylidene]-2,2,2-trifluoro-acetamide;

M.UN.6c) (E/Z)-2,2,2-trifluoro-N-[1-[(6-fluoro-3-pyridyl)methyl]-2-pyridylidene]acetamide;

M.UN.6d) (E/Z)—N-[1-[(6-bromo-3-pyridyl)methyl]-2-pyridylidene]-2,2,2-trifluoro-acetamide;

M.UN.6e) (E/Z)—N-[1-[1-(6-chloro-3-pyridyl)ethyl]-2-pyridylidene]-2,2,2-trifluoro-acetamide;

M.UN.6f) (E/Z)—N-[1-[(6-chloro-3-pyridyl)methyl]-2-pyridylidene]-2,2-difluoro-acetamide;

M.UN.6g) (E/Z)-2-chloro-N-[1-[(6-chloro-3-pyridyl)methyl]-2-pyridylidene]-2,2-difluoro-acetamide;

M.UN.6h) (E/Z)—N-[1-[(2-chloropyrimidin-5-yl)methyl]-2-pyridylidene]-2,2,2-trifluoro-acetamide;

M.UN.6i) (E/Z)—N-[1-[(6-chloro-3-pyridyl)methyl]-2-pyridylidene]-2,2,3,3,3-pentafluoropropanamide);

M.UN.6j) N-[1-[(6-chloro-3-pyridyl)methyl]-2-pyridylidene]-2,2,2-trifluoro-thioacetamide or of the compound M.UN.6k) N-[1-[(6-chloro-3-pyridyl)methyl]-2-pyridylidene]-2,2,2-trifluoro-W-isopropyl-acetamidine or the compounds M.UN.8: 8-chloro-N-[2-chloro-5-methoxyphenyl)sulfonyl]-6-trifluoromethyl)-imidazo[1,2-a]pyridine-2-carboxamide; or M.UN.9: 4-[5-(3,5-dichlorophenyl)-5-(trifluoromethyl)-4H-isoxazol-3-yl]-2-methyl-N-(1-oxothietan-3-yl)benzamide; or M.UN.10: 5-[3-[2,6-dichloro-4-(3,3-dichloroallyloxy)phenoxy]propoxy]-1H-pyrazole; or a compound selected from the group of M.UN.11, wherein the compound is selected from M.UN.11b) to M.UN.11p):

M.UN.11.b) 3-(benzoylmethylamino)-N-[2-bromo-4-[1,2,2,3,3,3-hexafluoro-1-(trifluoromethyl)propyl]-6-(trifluoromethyl)phenyl]-2-fluoro-benzamide;

M.UN.11.c) 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide;

M.UN.11.d) N-[3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide;

M.UN.11.e) N-[3-[[[2-bromo-4-[1,2,2,2-tetrafluoro-1-(trifluoromethyl)ethyl]-6-(trifluoromethyl)phenyl]amino]carbonyl]-2-fluorophenyl]-4-fluoro-N-methyl-benzamide;

M.UN.11.f) 4-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide;

M.UN.11.g) 3-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide;

M.UN.11.h) 2-chloro-N-[3-[[[2-iodo-4-[1,2,2,2-tetrafluoro-1-(trifluoromethyl)ethyl]-6-(trifluoromethyl)phenyl]amino]carbonyl]phenyl]-3-pyridinecarboxamide;

M.UN.11.i) 4-cyano-N-[2-cyano-5-[[2,6-dibromo-4-[1,2,2,3,3,3-hexafluoro-1-(trifluoromethyl)propyl]phenyl]carbamoyl]phenyl]-2-methyl-benzamide;

M.UN.11.j) 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide;

M.UN.11.k) N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methyl-benzamide;

M.UN.11.l) N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide;

M.UN.11.m) N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide;

M.UN.11.n) 4-cyano-N-[2-cyano-5-[[2,6-dichloro-4-[1,2,2,3,3,3-hexafluoro-1-(trifluoromethyl)propyl]phenyl]carbamoyl]phenyl]-2-methyl-benzamide;

M.UN.11.o) 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide;

M.UN.11.p) N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide;

or a compound selected from the group of M.UN.12, wherein the compound is selected from M.UN.12a) to M.UN.12m):

M.UN.12.a) 2-(1,3-Dioxan-2-yl)-6-[2-(3-pyridinyl)-5-thiazolyl]-pyridine;

M.UN.12.b) 2-[6-[2-(5-Fluoro-3-pyridinyl)-5-thiazolyl]-2-pyridinyl]-pyrimidine;

M.UN.12.c) 2-[6-[2-(3-Pyridinyl)-5-thiazolyl]-2-pyridinyl]-pyrimidine;

M.UN.12.d) N-Methylsulfonyl-6-[2-(3-pyridyl)thiazol-5-yl]pyridine-2-carboxamide

M.UN.12.e) N-Methylsulfonyl-6-[2-(3-pyridyl)thiazol-5-yl]pyridine-2-carboxamide

M.UN.12.f) N-Ethyl-N-[4-methyl-2-(3-pyridyl)thiazol-5-yl]-3-methylthio-propanamide M.UN.12.g) N-Methyl-N-[4-methyl-2-(3-pyridyl)thiazol-5-yl]-3-methylthio-propanamide M.UN.12.h) N,2-Dimethyl-N-[4-methyl-2-(3-pyridyl)thiazol-5-yl]-3-methylthio-propanamide M.UN.12.i) N-Ethyl-2-methyl-N-[4-methyl-2-(3-pyridyl)thiazol-5-yl]-3-methylthio-propanamide M.UN.12.j) N-[4-Chloro-2-(3-pyridyl)thiazol-5-yl]-N-ethyl-2-methyl-3-methylthio-propanamide M.UN.12.k) N-[4-Chloro-2-(3-pyridyl)thiazol-5-yl]-N,2-dimethyl-3-methylthio-propanamide M.UN.12.l) N-[4-Chloro-2-(3-pyridyl)thiazol-5-yl]-N-methyl-3-methylthio-propanamide M.UN.12.m) N-[4-Chloro-2-(3-pyridyl)thiazol-5-yl]-N-ethyl-3-methylthio-propanamide; or the compound M.UN.13: 2-(4-methoxyiminocyclohexyl)-2-(3,3,3-trifluoropropylsulfonyl)acetonitrile;

or the compounds

M.UN.14a) 1-[(6-Chloro-3-pyridinyl)methyl]-1,2,3,5,6,7-hexahydro-5-methoxy-7-methyl-8-nitroimidazo[1,2-a]pyridine; or M.UN.14b) 1-[(6-Chloropyridin-3-yl)methyl]-7-methyl-8-nitro-1,2,3,5,6,7-hexahydroimidazo[1,2-a]pyridin-5-ol; or the compound M.UN.15: 1-[(2-Chloro-1,3-thiazol-5-yl)methyl]-3-(3,5-dichlorophenyl)-9-methyl-4-oxo-4H-pyrido[1,2-a]pyrimidin-1-ium-2-olate.

M.Y Biopesticides, being pesticidal compounds of biological origin with insecticidal, acaricidal, molluscidal and/or nematicidal activity, including M.Y-1: Microbial pesticides: *Bacillus firmus, B. thuringiensis* ssp. *israelensis, B. t.* ssp. *galleriae, B. t.* ssp. *kurstaki, Beauveria bassiana, Burkholderia* sp., *Chromobacterium subtsugae, Cydia pomonella granulosis* virus, *Isaria fumosorosea, Lecanicillium longisporum, L. muscarium* (formerly *Verticillium lecanii*), *Metarhizium anisopliae, M. anisopliae* var. *acridum, Paecilomyces fumosoroseus, P. lilacinus, Paenibacillus pop-*

*piliae, Pasteuria* spp., *P. nishizawae* (Clariva®, *P. reneformis, P. usagae, Pseudomonas fluorescens, Steinernema feltiae, Streptomces galbus;* or actives on basis of *bacillus firmus* (Votivo®, 1-1582), or M.Y-2 Biochemical pesticides: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulylsenecioate, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-ylacetate, Z-7-tetradecen-2-one, Z-9-tetradecen-1-ylacetate, Z-11-tetradecenal, Z-11-tetradecen-1-ol, Acacia negra extract, extract of grapefruit seeds and pulp, extract of *Chenopodium* ambrosiodae, Catnip oil, Neem oil, Quillay extract, *Tagetes* oil or components of the ginkgo tree selected from the group consisting of bilobalide, ginkgolide A, ginkgolide B, ginkgolide C, ginkgolide J and ginkgolide M.

Preferred are combinations of the carboxamid compound of formula (I) with one or more insecticicidal active compound selected from the group consisting of acephate, chlorpyrifos, fipronil, methiocarb, thiodicarb, lamba-cyhalothrin, bifenthrin, cypermethrin, alpha-cypermethrin, tefluthrin, actemiprid, clothianidin, dinotefuran, imidacloprid, thiacloprid, thiamethoxam, abamectin, emamectin, flubendiamin, spinosad, triflumezopyrim, chlorantraniliprole or cyantraniliprole.

More preferred is the combination of the carboxamide compound of formula (I) with acephate.

More preferred is the combination of the carboxamide compound of formula (I) with chlorpyrifos.

More preferred is the combination of the carboxamide compound of formula (I) with fipronil.

More preferred is the combination of the carboxamide compound of formula (I) with methiocarb.

More preferred is the combination of the carboxamide compound of formula (I) with thiodicarb.

More preferred is the combination of the carboxamide compound of formula (I) with cypermethrin.

More preferred is the combination of the carboxamide compound of formula (I) with bifenthrin.

More preferred is the combination of the carboxamide compound of formula (I) with tefluthrin.

More preferred is the combination of the carboxamide compound of formula (I) with alpha-cypermethrin.

More preferred is the combination of the carboxamide compound of formula (I) with abamectin.

More preferred is the combination of the carboxamide compound of formula (I) with emamectin.

More preferred is the combination of the carboxamide compound of formula (I) with spinosad.

More preferred is the combination of the carboxamide compound of formula (I) with sulfoxaflor.

More preferred is the combination of the carboxamide compound of formula (I) with triflumezopyrim.

More preferred is the combination of the carboxamide compound of formula (I) with chlorantraniliprole.

More preferred is the combination of the carboxamide compound of formula (I) with cyantraniliprole.

More preferred is the combination of the carboxamide compound of formula (I) with N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide.

More preferred is the combination of the carboxamide compound of formula (I) with N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide.

More preferred is the combination of the carboxamide compound of formula (I) with N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide.

Preferred are combinations of the carboxamid compound of formula (I) with neonicotinic compounds of group M.4.

Utmost preferred is the combination of the carboxamide compound of formula (I) with acetamiprid.

Also utmost preferred is the combination of the carboxamide compound of formula (I) with clothianidin.

Also utmost preferred is the combination of the carboxamide compound of formula (I) with dinotefuran.

Also utmost preferred is the combination of the carboxamide compound of formula (I) with imidacloprid.

Also utmost preferred is the combination of the carboxamide compound of formula (I) with thiacloprid.

Also utmost preferred is the combination of the carboxamide compound of formula (I) with thiamethoxam.

More preferred is the combination of the carboxamide compound of formula (I) with actives on basis of *bacillus firmus* (Votivo, *bacillus firmus* strain I-1582).

Utmost preferred is the combination of the carboxamide compound of formula (I) with PONCHO®/VOTiVO™.

More preferred is the combination of the carboxamide compound of formula (I) with an active of *P. nishizawae* (Clariva®).

The commercially available compounds of the group M listed above may be found in The Pesticide Manual, 15th Edition, C. D. S. Tomlin, British Crop Protection Council (2011) among other publications.

The neonicotinoid cycloxaprid is known from WO20120/069266 and WO2011/06946, and the neonicotinoid compound M.4A.2, sometimes also to be named as Guadipyr, is known from WO2013/003977, and the neonicotinoid compound M.4A.3. (approved as paichongding in China) is known from WO2010/069266. The Metaflumizone analogue M.22B.1 is described in CN 10171577 and the analogue M.22B.2 in CN102126994. The phthalamides M.28.1 and M.28.2 are both known from WO 2007/101540. The anthranilamide M.28.3 has been described in WO2005/077934. The hydrazide compound M.28.4 has been described in WO 2007/043677. The anthranilamides M.28.5a) to M.28.5h) can be prepared as described in WO 2007/006670, WO2013/024009 and WO2013/024010, the anthranilamide compound M.28.5i) is described in WO2011/085575, the compound M.28.5j) in WO2008/134969, the compound M.28.5k) in US2011/046186 and the compound M.28.5l) in WO2012/034403. The diamide compounds M.28.6 and M.28.7 can be found in CN102613183. The anthranilamide compounds M.28.8a) and M.28.8b) are known from WO2010/069502.

The quinoline derivative flometoquin is shown in WO2006/013896. The aminofuranone compounds flupyradifurone is known from WO 2007/115644. The sulfoximine compound sulfoxaflor is known from WO2007/149134. From the pyrethroids group momfluorothrin is known from U.S. Pat. No. 6,908,945 and heptafluthrin from WO10133098. The oxadiazolone compound metoxadiazone can be found in JP13/166707. The pyrazole acaricide pyflubumide is known from WO2007/020986. The isoxazoline compounds have been described in following publications: fluralaner in WO2005/085216, afoxolaner in WO2009/002809 and in WO2011/149749 and the isoxazoline compound M.UN.9 in WO2013/050317. The pyripyropene derivative afidopyropen has been described in WO 2006/129714. The nematicide tioxazafen has been disclosed in WO09023721 and nematicide fluopyram in WO2008126922, nematicidal mixtures comprising flupyram in WO2010108616. The triflumezopyrim compound was described in WO2012/092115.

The spiroketal-substituted cyclic ketoenol derivative M.UN.3 is known from WO2006/089633 and the biphenyl-substituted spirocyclic ketoenol derivative M.UN.4 from WO2008/067911. The triazoylphenylsulfide M.UN.5 has been described in WO2006/043635, and biological control agents on basis of *bacillus firmus* in WO2009/124707.

The compounds M.UN.6a) to M.UN.6i) listed under M.UN.6 have been described in WO2012/029672 and compounds M.UN.6j) and M.UN.6k) in WO2013129688. The nematicide compound M.UN.8 in WO2013/055584 and the Pyridalyl-type analogue M.UN.10 in WO2010/060379. The carboxamide compounds M.UN.11.b) to M.UN.11.h) can be prepared as described in WO 2010/018714 and the carboxamide M.UN.11i) to M.UN.11.p) are described WO2010/127926. The pyridylthiazoles M.UN.12.a) to M.UN.12.c) are known from WO2010/006713, M.UN.12.c) and M.UN.12.d) WO2012000896 and M.UN.12.f) to M.UN.12.m) in WO2010129497. The malononitrile compound M.UN.13 was described in WO2009/005110. The compounds M.UN.14a) and M.UN.14b) are known from WO2007/101369. The compound M.UN.15 can be found in WO13192035.

The biopesticides of group M.Y. are disclosed further below in the paragraphs about biopesticides (from groups M.Y and F.XII).

The following list F of active fungicidal substances, in conjunction with which the compounds according to the invention also can be used, is intended to illustrate the possible combinations but does not limit them:

F.I) Respiration inhibitors

F.I 1) Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, mandestrobine, metominostrobin, orysastrobin, picoxystrobin, pyraclostrobin, pyrametostrobin, pyraoxystrobin, trifloxystrobin and 2-(2-(3-(2,6-dichlorophenyl)-1-methyl-allylideneaminooxymethyl)-phenyl)-2-methoxyimino-N-methyl-acetamide, pyribencarb, triclopyricarb/chlorodincarb, famoxadone, fenamidone;

F.I 2) inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate F.I 3) inhibitors of complex II (e.g. carboxamides): benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl) pyrazole-4-carboxamide, 1,3-dimethyl-N-(1,1,3-trimethyl-indan-4-yl)pyrazole-4-carboxamide, 3-(trifluoromethyl)-1, 5-dimethyl-N-(1,1,3-trimethylindan-4-yl)pyrazole-4-carboxamide, 1,3,5-trimethyl-N-(1,1,3-trimethylindan-4-yl) pyrazole-4-carboxamide, N-(7-fluoro-1,1,3-trimethyl-indan-4-yl)-1,3-dimethyl-pyrazole-4-carboxamide, N-[2-(2, 4-dichlorophenyl)-2-methoxy-1-methyl-ethyl]-3-(difluoromethyl)-1-methyl-pyrazole-4-carboxamide, N-[2-(2,4-difluorophenyl)phenyl]-3-(trifluoromethyl)pyrazine-2-carboxamide;

F.I 4) other respiration inhibitors (e.g. complex I, uncouplers): diflumetorim, (5,8-difluoro-quinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

F.II) Sterol biosynthesis inhibitors (SBI fungicides)

F.II 1) C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole,
1-[rel-(2S;3R)-3-(2-chlorophenyl)-2-(2,4-difluorophenyl)-oxiranylmethyl]-5-thiocyanato-1H-[1,2,4]triazole, 2-[rel-(2S;3A)-3-(2-chlorophenyl)-2-(2,4-difluorophenyl)-oxiranylmethyl]-2H-[1,2,4]triazole-3-thiol, 2-[2-chloro-4-(4-chlorophenoxy)phenyl]-1-(1,2,4-triazol-1-yl)pentan-2-ol, 1-[4-(4-chlorophenoxy)-2-(trifluoromethyl)phenyl]-1-cyclopropyl-2-(1,2,4-triazol-1-yl)ethanol, 2-[4-(4-chlorophenoxy)-2-(trifluoromethyl)phenyl]-1-(1,2,4-triazol-1-yl)butan-2-ol, 2-[2-chloro-4-(4-chlorophenoxy) phenyl]-1-(1,2,4-triazol-1-yl)butan-2-ol, 2-[4-(4-chlorophenoxy)-2-(trifluoromethyl)phenyl]-3-methyl-1-(1, 2,4-triazol-1-yl)butan-2-ol, 2-[4-(4-chlorophenoxy)-2-(trifluoromethyl)phenyl]-1-(1,2,4-triazol-1-yl)propan-2-ol, 2-[2-chloro-4-(4-chlorophenoxy)phenyl]-3-methyl-1-(1,2, 4-triazol-1-yl)butan-2-ol, 2-[4-(4-chlorophenoxy)-2-(trifluoromethyl)phenyl]-1-(1,2,4-triazol-1-yl)pentan-2-ol, 2-[4-(4-fluorophenoxy)-2-(trifluoromethyl)phenyl]-1-(1,2,4-triazol-1-yl)propan-2-ol; imidazoles: imazalil, pefurazoate, prochloraz, triflumizol; pyrimidines, pyridines and piperazines: fenarimol, nuarimol, pyrifenox, triforine, [3-(4-chloro-2-fluoro-phenyl)-5-(2,4-difluorophenyl)isoxazol-4-yl]-(3-pyridyl)methanol;

F.II 2) Delta14-reductase inhibitors: aldimorph, dodemorph, dodemorph-acetate, fenpropimorph, tridemorph, fenpropidin, piperalin, spiroxamine;

F.II 3) Inhibitors of 3-keto reductase: fenhexamid;

F.III) Nucleic acid synthesis inhibitors

F.III 1) phenylamides or acyl amino acid fungicides: benalaxyl, benalaxyl-M, kiralaxyl, metalaxyl, metalaxyl-M (mefenoxam), ofurace, oxadixyl;

F.III 2) others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4-amine;

F.IV) Inhibitors of cell division and cytoskeleton

F.IV 1) tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine F.IV 2) other cell division inhibitors: diethofencarb, ethaboxam, pencycuron, fluopicolide, zoxamide, metrafenone, pyriofenone;

F.V) Inhibitors of amino acid and protein synthesis

F.V 1) methionine synthesis inhibitors (anilino-pyrimidines): cyprodinil, mepanipyrim, pyrimethanil;

F.V 2) protein synthesis inhibitors: blasticidin-S, kasugamycin, kasugamycin hydrochloride-hydrate, mildiomycin, streptomycin, oxytetracyclin, polyoxine, validamycin A;

F.VI) Signal transduction inhibitors

F.VI 1) MAP/histidine kinase inhibitors: fluoroimid, iprodione, procymidone, vinclozolin, fenpiclonil, fludioxonil;

F.VI 2) G protein inhibitors: quinoxyfen;

F.VII) Lipid and membrane synthesis inhibitors

F.VII 1) Phospholipid biosynthesis inhibitors: edifenphos, iprobenfos, pyrazophos, isoprothiolane;

F.VII 2) lipid peroxidation: dicloran, quintozene, tecnazene, tolclofos-methyl, biphenyl, chloroneb, etridiazole;

F.VII 3) phospholipid biosynthesis and cell wall deposition: dimethomorph, flumorph, mandipropamid, pyrimorph, benthiavalicarb, iprovalicarb, valifenalate and N-(1-(1-(4-cyano-phenyl)-ethanesulfonyl)-but-2-yl) carbamic acid-(4-fluorophenyl) ester;

F.VII 4) compounds affecting cell membrane permeability and fatty acids: propamocarb, propamocarb-hydrochlorid F.VII 5) fatty acid amide hydrolase inhibitors: oxathiapiprolin;

F.VIII) Inhibitors with Multi Site Action

F.VIII 1) inorganic active substances: Bordeaux mixture, copper acetate, copper hydroxide, copper oxychloride, basic copper sulfate, sulfur;

F.VIII 2) thio- and dithiocarbamates: ferbam, mancozeb, maneb, metam, metiram, propineb, thiram, zineb, ziram;

F.VIII 3) organochlorine compounds (e.g. phthalimides, sulfamides, chloronitriles): anilazine, chlorothalonil, captafol, captan, folpet, dichlofluanid, dichlorophen, hexachlorobenzene, pentachlorphenole and its salts, phthalide, tolylfluanid, N-(4-chloro-2-nitro-phenyl)-N-ethyl-4-methyl-benzenesulfonamide;

F.VIII 4) guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;

F.IX) Cell wall synthesis inhibitors

F.IX 1) inhibitors of glucan synthesis: validamycin, polyoxin B;

F.IX 2) melanin synthesis inhibitors: pyroquilon, tricyclazole, carpropamid, dicyclomet, fenoxanil;

F.X) Plant defense inducers

F.X 1) acibenzolar-S-methyl, probenazole, isotianil, tiadinil, prohexadione-calcium;

F.X 2) phosphonates: fosetyl, fosetyl-aluminum, phosphorous acid and its salts, 4-cyclopropyl-N-(2,4-dimethoxy-phenyl)thiadiazole-5-carboxamide;

F.XI) Unknown mode of action bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, picarbutrazox, tolprocarb, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, oxin-copper, proquinazid, tebufloquin, tecloftalam, triazoxide, 2-butoxy-6-iodo-3-propylchromen-4-one, N-(cyclopropylmethoxy-imino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chloro-phenyl)-2,3-dimethyl-isoxazolidin-3-yl]-pyridine (pyrisoxazole), N-(6-methoxy-pyridin-3-yl) cyclopropane-carboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate, pentyl N-[6-[[(Z)-[(1-methyltetrazol-5-yl)-phenyl-methylene]amino]oxymethyl]-2-pyridyl]carbamate, 2-[2-[(7,8-difluoro-2-methyl-3-quinolyl)oxy]-6-fluoro-phenyl]propan-2-ol, 2-[2-fluoro-6-[(8-fluoro-2-methyl-3-quinolyl)oxy]phenyl]propan-2-ol, 3-(5-fluoro-3,3,4,4-tetramethyl-3,4-dihydroisoquinolin-1-yl)quinoline, 3-(4,4-difluoro-3,3-dimethyl-3,4-dihydroisoquinolin-1-yl)quinoline, 3-(4,4,5-trifluoro-3,3-dimethyl-3,4-dihydroisoquinolin-1-yl)quinoline;

F.XII) Biopesticides

F.XII 1) Microbial pesticides with fungicidal, bactericidal, viricidal and/or plant defense activator activity: *Ampelomyces quisqualis, Aspergillus flavus, Aureobasidium pullulans, Bacillus amyloliquefaciens, B. mojavensis, B. pumilus, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus polymyxa, Pantoea vagans, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma asperellum, T. atroviride, T. fertile, T. gamsii, T. harmatum, T. harzianum*; mixture of *T. harzianum* and *T. viride*; mixture of *T. polysporum* and *T. harzianum*; *T. stromaticum*, *T. virens* (also named *Gliocladium virens*), *T. viride*, *Typhula phacorrhiza*, *Ulocladium oudemansii*, *Verticillium dahlia*, zucchini yellow mosaic virus (avirulent strain);

F.XII 2) Biochemical pesticides with fungicidal, bactericidal, viricidal and/or plant defense activator activity: chitosan (hydrolysate), harpin protein, laminarin, Menhaden fish oil, natamycin, Plum pox virus coat protein, potassium or sodium bicarbonate, *Reynoutria sachlinensis* extract, salicylic acid, tea tree oil;

Preferrably, the fungicide is selected from Amisulbrom, Azoxystrobin, Benalaxyl, Benzovindiflupyr, Bixafen, Boscalid, Coumethoxystrobin, Coumoxystrobin, Cyazofamid, Cyproconazole, Difenoconazole, Dimethomorph, Dimoxystrobin, Ethaboxam, Fludioxonil, Fluopyram, Fluoxastrobin, Fluquinconazole, Fluxapyroxad, Hymexazole, Ipconazole, Iprodione, Isopyrazam, Metalaxyl, Metconazole, Penflufen, Penthiopyrad, Picarbutrazox, Picoxystrobin, Prochloraz, Prothioconazole, Pyraclostrobin, Pyrimethanil, Sedaxane, Silthiofam, Tebuconazole, Thiabendazol, Thiophanate methyl, Thiram, Triadimenol, Triazoxide, Trifloxystrobin, Triticonazole, N-[2-(2,4-difluorophenyl)phenyl]-3-(trifluoromethyl)pyrazine-2-carboxamide and 4-cyclopropyl-N-(2,4-dimethoxyphenyl)thiadiazole-5-carboxamide.

More preferable, the fungicide is selected from Amisulbrom, Azoxystrobin, Benzovindiflupyr, Boscalid, Difenoconazole, Dimethomorph, Fludioxonil, Fluopyram, Fluxapyroxad, Ipconazole, Metalaxyl, Penflufen, Penthiopyrad, Picarbutrazox, Picoxystrobin, Prothioconazole, Pyraclostrobin, Pyrimethanil, Sedaxane, Silthiofam, Thiophanate methyl, Trifloxystrobin, Triticonazole.

Preferred is further the combination of the carboxamide compound of formula (I) with a fungicide selected from the group consisting of 2-[2-chloro-4-(4-chlorophenoxy)phenyl]-1 (1,2,4-triazol-1-yl)pentan-2-ol, 1-[4-(4-chlorophenoxy)-2-(trifluoromethyl)phenyl]-1 cyclopropyl-2-(1,2,4-triazol-1-yl)ethanol, 2-[4-(4-chlorophenoxy)-2-(trifluorometh¬yl)phenyl]-1-(1,2,4-triazol-1-yl)butan-2-ol, 2-[2-chloro-4-(4-chlorophenoxy)phenyl]-1-(1,2,4-triazol-1-yl)butan-2-ol, 2-[4-(4-chlorophenoxy)-2-(trifluoromethyl) phenyl]-3-methyl-1-(1,2,4-triazol-1-yl)butan-2-ol, 2-[4-(4-chlorophenoxy)-2-(trifluoromethyl)¬phenyl]-1-(1,2,4-triazol-1-yl)propan-2-ol, 2-[2-chloro-4-(4-chlorophenoxy) phenyl]-3-methyl-1-(1,2,4-triazol-1-yl)butan-2-ol, 2-[4-(4-chlorophenoxy)-2-(trifluoromethyphenyl]-1-(1,2,4-triazol-1-yl)pentan-2-ol or 2-[4-(4-fluorophenoxy)-2-(trifluoromethyl)phenyl]-1-(1,2,4-triazol-1-yl)propan-2-ol.

Utmost preferred is the combination of the carboxamide compound of formula (I) with 2-[2-chloro-4-(4-chlorophenoxy)phenyl]-1 (1,2,4-triazol-1-yl)pentan-2-ol.

Utmost preferred is the combination of the carboxamide compound of formula (I) with 1-[4-(4-chlorophenoxy)-2-(trifluoromethyl)phenyl]-1 cyclopropyl-2-(1,2,4-triazol-1-yl)ethanol Utmost preferred is the combination of the carboxamide compound of formula (I) with 2-[4-(4-chlorophenoxy)-2-(trifluorometh¬yl)phenyl]-1-(1,2,4-triazol-1-yl)butan-2-ol Utmost preferred is the combination of the carboxamide compound of formula (I) with 2-[2-chloro-4-(4-chlorophenoxy)phenyl]-1-(1,2,4-triazol-1-yl)butan-2-ol Utmost preferred is the combination of the carboxamide compound of formula (I) with 2-[4-(4-chlorophenoxy)-2-(trifluoromethyl)phenyl]-3-methyl-1-(1,2,4-triazol-1-yl)butan-2-ol.

Utmost preferred is the combination of the carboxamide compound of formula (I) with 2-[4-(4-chlorophenoxy)-2-(trifluoromethyl)¬phenyl]-1-(1,2,4-triazol-1-yl)propan-2-ol.

Utmost preferred is the combination of the carboxamide compound of formula (I) with 2-[2-chloro-4-(4-chlorophenoxy)phenyl]-3-methyl-1-(1,2,4-triazol-1-yl)butan-2-ol.

Utmost preferred is the combination of the carboxamide compound of formula (I) with 2-[4-(4-chlorophenoxy)-2-(trifluoromethyl)¬phenyl]-1-(1,2,4-triazol-1-yl)pentan-2-ol.

Utmost preferred is the combination of the carboxamide compound of formula (I) with 2-[4-(4-fluorophenoxy)-2-(trifluoromethyl)¬phenyl]-1-(1,2,4-triazol-1-yl)propan-2-ol.

Utmost preferred is the combination of the carboxamide compound of formula (I) with Azoxystrobin.

Also utmost preferred is the combination of the carboxamide compound of formula (I) with Boscalid.

Also utmost preferred is the combination of the carboxamide compound of formula (I) with Difenoxonazole.

Also utmost preferred is the combination of the carboxamide compound of formula (I) with Fludioxonil.

Also utmost preferred is the combination of the carboxamide compound of formula (I) with Fluxapyroxad.

Also utmost preferred is the combination of the carboxamide compound of formula (I) with Ipconazole.

Also utmost preferred is the combination of the carboxamide compound of formula (I) with Epoxiconazole.

Also utmost preferred is the combination of the carboxamide compound of formula (I) with Metalaxyl.

Also utmost preferred is the combination of the carboxamide compound of formula (I) with Penflufen.

Also utmost preferred is the combination of the carboxamide compound of formula (I) with Pyraclostrobin.

Also utmost preferred is the combination of the carboxamide compound of formula (I) with Pyrimethanil.

Also utmost preferred is the combination of the carboxamide compound of formula (I) with Sedaxane.

Also utmost preferred is the combination of the carboxamide compound of formula (I) with Silthiofarm.

Also utmost preferred is the combination of the carboxamide compound of formula (I) with Thiophanate-Methyl.

Also utmost preferred is the combination of the carboxamide compound of formula (I) with Triticonazole.

The funicidal pesticides of chemical nature described by common names, their preparation and their activity against pests is known (cf.: http://www.alanwood.net/pesticides/); these pesticides are often commercially available.

The funicidal pesticides described by IUPAC nomenclature, their preparation and their pesticidal activity is also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 11/77514; WO13/047749, WO 10/069882, WO 13/047441, WO 03/16303, WO 09/90181, WO 13/007767, WO 13/010862, WO 13/024009 and WO 13/024010).

Biopesticides

The biopesticides from group II.M.Y or F.XII, their preparation and their pesticidal activity e.g. against harmful fungi or insects are known (e-Pesticide Manual V 5.2 (ISBN 978 1 901396 85 0) (2008-2011); http://www.epa.gov/opp00001/biopesticides/, see product lists therein; http://www.omri.org/omri-lists, see lists therein; Bio-Pesticides Database BPDB http://sitem.herts.ac.uk/aeru/bpdb/, see A to Z link therein).

The biopesticides from group II.M.Y or F.XII. may also have insecticidal, fungicidal, acaricidal, molluscidal, viricidal, bactericidal, pheromone, nematicidal, plant defense activator, plant stress reducing, plant growth regulator, plant growth promoting, plant growth regulator and/or yield enhancing activity.

Many of these biopesticides are registered and/or are commercially available: aluminium silicate (Screen™ Duo from Certis LLC, USA), Agrobacterium radio-bacter K1026 (e.g. NoGall® from Becker Underwood Pty Ltd., Australia), A. radiobacter K84 (Nature 280, 697-699, 1979; e.g. Gall-Troll® from AG Biochem, Inc., C, USA), Ampelomyces quisqualis M-10 (e.g. AQ 10® from Intrachem Bio GmbH & Co. KG, Germany), Ascophyllum nodosum (Norwegian kelp, Brown kelp) extract or filtrate (e.g. ORKA GOLD from Becker Underwood, South Africa; or Goemar® from Laboratoires Goemar, France), Aspergillus flavus NRRL 21882 isolated from a peanut in Georgia in 1991 by the USDA, National Peanut Research Laboratory (e.g. in Afla-Guard® from Syngenta, CH), mixtures of Aureobasidium pullulans DSM14940 and DSM 14941 (e.g. blastospores in Blossom-Protect® from bio-ferm GmbH, Germany), Azospirillum brasilense XOH (e.g. AZOS from Xtreme Gardening, USA or RTI Reforestation Technologies International; USA), Bacillus amyloliquefaciens FZB42 (e.g. in RhizoVital® 42 from AbiTEP GmbH, Berlin, Germany), B. amyloliquefaciens IN937a (J. Microbiol. Biotechnol. 17(2), 280-286, 2007; e.g. in BioYield® from Gustafson LLC, TX, USA), B. amyloliquefaciens IT-45 (CNCM 1-3800) (e.g. Rhizocell C from ITHEC, France), B. amyloliquefaciens subsp. plantarum MBI600 (NRRL B-50595, deposited at United States Department of Agriculture) (e.g. Integral®, Subtilex® NG from Becker Underwood, USA), B. cereus CNCM 1-1562 (U.S. Pat. No. 6,406,690), B. firmus CNCM 1-1582 (WO 2009/126473, WO 2009/124707, U.S. Pat. No. 6,406,690; Votivo® from Bayer Crop Science LP, USA), B. pumilus GB34 (ATCC 700814; e.g. in YieldShield® from Gustafson LLC, TX, USA), and Bacillus pumilus KFP9F (NRRL B-50754) (e.g. in BAC-UP or FUSION-P from Becker Underwood South Africa), B. pumilus QST 2808 (NRRL B-30087) (e.g. Sonata® and Ballad® Plus from AgraQuest Inc., USA), B. subtilis GB03 (e.g. Kodiak® or BioYield® from Gustafson, Inc., USA; or Companion® from Growth Products, Ltd., White Plains, N.Y. 10603, USA), B. subtilis GB07 (Epic® from Gustafson, Inc., USA), B. subtilis QST-713 (NRRL B-21661 in Rhapsody®, Serenade® MAX and Serenade® ASO from AgraQuest Inc., USA), B. subtilis var. amylolique-faciens FZB24 (e.g. Taegro® from Novozyme Biologicals, Inc., USA), B. subtilis var. amyloliquefaciens D747 (e.g. Double Nickel 55 from Certis LLC, USA), B. thuringiensis ssp. aizawai ABTS-1857 (e.g. in XenTari® from BioFa AG, Münsingen, Germany), B. t. ssp. aizawai SAN 401 I, ABG-6305 and ABG-6346, Bacillus t. ssp. israelensis AM65-52 (e.g. in VectoBac® from Valent BioSciences, Ill., USA), Bacillus thuringiensis ssp. kurstaki SB4 (NRRL B-50753; e.g. Beta Pro® from Becker Underwood, South Africa), B. t. ssp. kurstaki ABTS-351 identical to HD-1 (ATCC SD-1275; e.g. in Dipel® DF from Valent BioSciences, Ill., USA), B. t. ssp. kurstaki EG 2348 (e.g. in Lepinox® or Rapax® from CBC (Europe) S.r.I., Italy), B. t. ssp. tenebrionis DSM 2803 (EP 0 585 215 B1; identical to NRRL B-15939; Mycogen Corp.), B. t. ssp. tenebrionis NB-125 (DSM 5526; EP 0 585 215 B1; also referred to as SAN 4181 or ABG-6479; former production strain of NovoNordisk), B. t. ssp. tenebrionis NB-176 (or NB-176-1) a gamma-irridated, induced high-yielding mutant of strain NB-125 (DSM 5480; EP 585 215 B1; Novodor® from Valent BioSciences, Switzerland), Beauveria bassiana ATCC 74040 (e.g. in Naturalis® from CBC (Europe) S.r.I., Italy), B. bassiana DSM 12256 (US 200020031495; e.g. BioExpert® SC from Live Sytems Technology S.A., Colombia), B. bassiana GHA (BotaniGard® 22WGP from Laverlam Int. Corp., USA), B. bassiana PPRI 5339 (ARSEF number 5339 in the USDA ARS collection of entomopathogenic fungal cultures; NRRL 50757) (e.g. BroadBand® from Becker Underwood, South Africa), B. brongniartii (e.g. in Melocont® from Agrifutur, Agrianello, Italy, for control of cockchafer; J. Appl. Microbiol. 100(5), 1063-72, 2006), Bradyrhizobium sp. (e.g. Vault® from Becker Underwood, USA), B. japonicum (e.g. VAULT® from Becker Underwood, USA), Candida oleophila 1-182 (NRRL Y-18846; e.g. Aspire® from Ecogen Inc., USA, Phytoparasitica 23(3), 231-234, 1995), C. oleophila strain O (NRRL Y-2317; Biological Control 51, 403-408, 2009) Candida saitoana (e.g. Biocure® (in mixture with lysozyme) and BioCoat® from Micro Flo Company, USA (BASF SE) and Arysta), Chitosan (e.g. Armour-Zen® from BotriZen Ltd., NZ), Clonostachys rosea f. catenulata, also named Gliocladium catenulatum (e.g. isolate J 1446: Prestop® from Verdera Oy, Finland), Chromobacterium subtsugae PRAA4-1 isolated from soil under an eastern hemlock (Tsuga canadensis) in the Catoctin Mountain region of central Maryland (e.g. in GRANDEVO from Marrone Bio Innovations, USA), Coniothyrium minitans CON/M/91-08 (e.g. Contans® WG from Prophyta, Germany), Cryphonectria parasitica (e.g. Endothia parasitica from CNICM, France), Cryptococcus albidus (e.g. YIELD PLUS® from Anchor Bio-Technologies, South Africa), Cryptophlebia leucotreta granulovirus (CrleGV) (e.g. in CRYPTEX from Adermatt Biocontrol, Switzerland), Cydia pomonella granulovirus (CpGV) V03 (DSM GV-0006; e.g. in MADEX Max from Andermatt Biocontrol, Switzerland), CpGV V22 (DSM GV-0014; e.g. in MADEX Twin from Adermatt Biocontrol, Switzerland), Delftia acidovorans RAY209 (ATCC PTA-4249; WO 2003/57861; e.g. in BIOBOOST from Brett Young, Winnipeg, Canada), Dilophosphora alopecuri (Twist Fungus from Becker Underwood, Australia), Ecklonia maxima (kelp) extract (e.g. KELPAK SL from Kelp Products Ltd, South Africa), formononetin (e.g. in MYCONATE from Plant Health Care plc, U.K.), Fusarium oxysporum (e.g. BIO-FOX® from S.I.A.P.A., Italy, FUSACLEAN® from Natural Plant Protection, France), Glomus intraradices (e.g. MYC 4000 from ITHEC, France), Glomus intraradices RTI-801 (e.g. MYKOS from Xtreme Gardening, USA or RTI Reforestation Technologies International; USA), grapefruit seeds and pulp extract (e.g. BC-1000 from Chemie S.A., Chile), harpin (alpha-beta) protein (e.g. MESSENGER or HARP-N-Tek from Plant Health Care plc, U.K.; Science 257, 1-132, 1992), Heterorhabditis bacteriophaga (e.g. Nemasys® G from Becker Underwood Ltd., UK), Isaria fumosorosea Apopka-97 (ATCC 20874) (PFR-97™ from Certis LLC, USA), cis-jasmone (U.S. Pat. No. 8,221,736), laminarin (e.g. in VACCIPLANT from Laboratoires Goemar, St. Malo, France or Stähler SA, Switzerland), *Lecanicillium longisporum* KV42 and KV71 (e.g. VERTALEC® from Koppert BV, Netherlands), *L. muscarium* KV01 (formerly *Verticillium lecanii*) (e.g. MYCOTAL from Koppert BV, Netherlands), *Lysobacter antibioticus* 13-1 (Biological Control 45, 288-296, 2008), *L. antibioticus* HS124 (Curr. Microbiol. 59(6), 608-615, 2009), *L. enzymogenes* 3.1T8 (Microbiol. Res. 158, 107-115; Biological Control 31(2), 145-154, 2004), *Metarhizium anisopliae* var. *acridum* IMI 330189 (isolated from *Ornithacris cavroisi* in Niger; also NRRL 50758) (e.g. GREEN MUSCLE® from Becker Underwood, South Africa), *M. a.* var. *acridum* FI-985 (e.g. GREEN GUARD® SC from Becker Underwood Pty Ltd, Australia), *M. anisopliae* FI-1045 (e.g. BIOCANE® from Becker Underwood Pty Ltd, Australia), *M. anisopliae* F52 (DSM 3884, ATCC 90448; e.g. MET52® Novozymes Biologicals BioAg Group, Canada), *M. anisopliae* ICIPE 69 (e.g. METATHRIPOL from ICIPE, Nairobe, Kenya), *Metschnikowia fructicola* (NRRL Y-30752; e.g. SHEMER® from Agrogreen, Israel, now distributed by Bayer CropSciences, Germany; U.S. Pat. No. 6,994,849), *Microdochium dimerum* (e.g. ANTIBOT® from Agrauxine, France), *Microsphaeropsis ochracea* P130A (ATCC 74412 isolated from apple leaves from an abandoned orchard, St-Joseph-du-Lac, Quebec, Canada in 1993; Mycologia 94(2), 297-301, 2002), *Muscodor albus* QST 20799 originally isolated from the bark of a cinnamon tree in Honduras (e.g. in development products Muscudor™ or QRD300 from AgraQuest, USA), Neem oil (e.g. TRILOGY®, TRIACT® 70 EC from Certis LLC, USA), *Nomuraea rileyi* strains SA86101, GU87401, SR86151, CG128 and VA9101, *Paecilomyces fumosoroseus* FE 9901 (e.g. NO FLY™ from Natural Industries, Inc., USA), *P. lilacinus* 251 (e.g. in BioAct®/ MeloCon® from Prophyta, Germany; Crop Protection 27, 352-361, 2008; originally isolated from infected nematode eggs in the Philippines), *P. lilacinus* DSM 15169 (e.g. NEMATA® SC from Live Systems Technology S.A., Colombia), *P. lilacinus* BCP2 (NRRL 50756; e.g. PL GOLD from Becker Underwood BioAg SA Ltd, South Africa), mixture of *Paenibacillus alvei* NAS6G6 (NRRL B-50755), *Pantoea vagans* (formerly *agglomerans*) C9-1 (originally isolated in 1994 from apple stem tissue; BlightBan C9-1® from NuFrams America Inc., USA, for control of fire blight in apple; J. Bacteriol. 192(24) 6486-6487, 2010), *Pasteuria* spp. ATCC PTA-9643 (WO 2010/085795), *Pasteuria* spp. ATCC SD-5832 (WO 2012/064527), *P. nishizawae* (WO 2010/80169), *P. penetrans* (U.S. Pat. No. 5,248,500), *P. ramose* (WO 2010/80619), *P. thornea* (WO 2010/80169), *P. usgae* (WO 2010/80169), *Penicillium bilaiae* (e.g. Jump Start® from Novozymes Biologicals BioAg Group, Canada, originally isolated from soil in southern Alberta; Fertilizer Res. 39, 97-103, 1994), *Phlebiopsis gigantea* (e.g. RotStop® from Verdera Oy, Finland), *Pichia anomala* WRL-076 (NRRL Y-30842; U.S. Pat. No. 8,206,972), potassium bicarbonate (e.g. Amicarb® fromm Stahler SA, Switzerland), potassium silicate (e.g. Sil-MATRIX™ from Certis LLC, USA), *Pseudozyma flocculosa* PF-A22 UL (e.g. Sporodex® from Plant Products Co. Ltd., Canada), *Pseudomonas* sp. DSM 13134 (WO 2001/40441, e.g. in PRORADIX from Sourcon Padena GmbH & Co. KG, Hechinger Str. 262, 72072 Tubingen, Germany), *P. chloraphis* MA 342 (e.g. in CERALL or CEDEMON from BioAgri AB, Uppsala, Sweden), *P. fluorescens* CL 145A (e.g. in ZEQUANOX from Marrone BioInnovations, Davis, Calif., USA; J. Invertebr. Pathol. 113(1):104-14, 2013), *Pythium oligandrum* DV 74 (ATCC 38472; e.g. POLYVERSUM® from Remeslo SSRO, Biopreparaty, Czech Rep. and GOWAN, USA; US 2013/0035230), *Reynoutria sachlinensis* extract (e.g. REGALIA® SC from Marrone BioInnovations, Davis, Calif., USA), *Rhizobium leguminosarum* bv. *phaseolii* (e.g. RHIZO-STICK from Becker Underwood, USA), *R. I. trifolii* RP113-7 (e.g. DORMAL from Becker Underwood, USA; Appl. Environ. Microbiol. 44(5), 1096-1101), *R. I.* bv. *viciae* P1NP3Cst (also referred to as 1435; New Phytol 179(1), 224-235, 2008; e.g. in NODULATOR PL Peat Granule from Becker Underwood, USA; or in NODULATOR XL PL bfrom Becker Underwood, Canada), *R. I.* bv. *viciae* SU303 (e.g. NODULAID Group E from Becker Underwood, Australia), *R. I.* bv. *viciae* WSM1455 (e.g. NODULAID Group F from Becker Underwood, Australia), *R. tropici* SEMIA 4080 (identical to PRF 81; Soil Biology & Biochemistry 39, 867-876, 2007), *Sinorhizobium meliloti* MSDJ0848 (INRA, France) also referred to as strain 2011 or RCR2011 (Mol Gen Genomics (2004) 272: 1-17; e.g. DORMAL ALFALFA from Becker Underwood, USA; NITRAGIN® Gold from Novozymes Biologicals BioAg Group, Canada), *Sphaerodes mycoparasitica* IDAC 301008-01 (WO 2011/022809), *Steinernema carpocapsae* (e.g. MILLENIUM® from Becker Underwood Ltd., UK), *S. feltiae* (NEMASHIELD®) from BioWorks, Inc., USA; NEMASYS® from Becker Underwood Ltd., UK), *S. kraussei* L137 (NEMASYS® L from Becker Underwood Ltd., UK), *Streptomyces griseoviridis* K61 (e.g. MYCOSTOP® from Verdera Oy, Espoo, Finland; Crop Protection 25, 468-475, 2006), *S. lydicus* WYEC 108 (e.g. Actinovate® from Natural Industries, Inc., USA, U.S. Pat. No. 5,403,584), *S. violaceusniger* YCED-9 (e.g. DT-9® from Natural Industries, Inc., USA, U.S. Pat. No. 5,968, 503), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. asperellum* ICC 012 (e.g. in TENET WP, REMDIER WP, BIOTEN WP from Isagro NC, USA, BIO-TAM from AgraQuest, USA), *T. atroviride* LC52 (e.g. SENTINEL® from Agrimm Technologies Ltd, NZ), *T. atroviride* CNCM 1-1237 (e.g. in Esquive WG from Agrauxine S.A., France, e.g. against pruning wound diseases on vine and plant root pathogens), *T. fertile* JM41R (NRRL 50759; e.g. RICHPLUS™ from Becker Underwood Bio Ag SA Ltd, South Africa), *T. gamsii* ICC 080 (e.g. in TENET WP, REMDIER WP, BIOTEN WP from Isagro NC, USA, BIO-TAM from AgraQuest, USA), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (also named *Gliocladium virens*) (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy) and *Ulocladium oudemansii* HRU3 (e.g. in BOTRY-ZEN® from BotryZen Ltd, NZ).

Strains can be sourced from genetic resource and deposition centers: American Type Culture Collection, 10801 University Blvd., Manassas, Va. 20110-2209, USA (strains with ATCC prefic); CABI Europe—International Mycological Institute, Bakeham Lane, Egham, Surrey, TW20 9TYN-RRL, UK (strains with prefices CABI and IMI); Centraalbureau voor Schimmelcultures, Fungal Biodiversity Centre, Uppsalaan 8, PO Box 85167, 3508 AD Utrecht, Netherlands (strains with prefic CBS); Division of Plant Industry, CSIRO, Canberra, Australia (strains with prefix CC); Collection Nationale de Cultures de Microorganismes, Institut Pasteur, 25 rue du Docteur Roux, F-75724 PARIS Cedex 15 (strains with prefix CNCM); Leibniz-Institut DSMZ-Deutsche Sammlung von Mikroorganismen und Zellkulturen GmbH, InhoffenstraRe 7 B, 38124 Braunschweig, Germany (strains with prefix DSM); International Depositary Authority of Canada Collection, Canada (strains with prefix IDAC); International Collection of Micro-organisms from Plants, Landcare Research, Private Bag 92170, Auckland Mail Centre, Auckland 1142, New Zealand (strains with prefix ICMP); IITA, PMB 5320, Ibadan, Nigeria (strains with prefix IITA); The National Collections of Industrial and Marine Bacteria Ltd., Torry Research Station, P.O. Box 31, 135 Abbey Road, Aberdeen, AB9 8DG, Scotland (strains with prefix NCIMB); ARS Culture Collection of the National Center for Agricultural Utilization Research, Agricultural Research Service, U.S. Department of Agriculture, 1815 North University Street, Peoria, Ill. 61604, USA (strains with prefix NRRL); Department of Scientific and Industrial Research Culture Collection, Applied Biochemistry Division, Palmerston North, New Zealand (strains with prefix NZP); FEPAGRO-Fundação Estadual de Pesquisa Agropecuaria, Rua Gonsalves Dias, 570, Bairro Menino Deus, Porto Alegre/RS, Brazil (strains with prefix SEMIA); SARDI, Adelaide, South Australia (strains with prefix SRDI); U.S. Department of Agriculture, Agricultural Research Service, Soybean and Alfalfa Research Laboratory, BARC-West, 10300 Baltimore Boulevard, Building 011, Room 19-9, Beltsville, Md. 20705, USA (strains with prefix USDA: Beltsville Rhizobium Culture Collection Catalog March 1987 USDA-ARS ARS-30: http://pdf.usaid.gov/pdf_docs/PNAAW891.pdf); and Murdoch University, Perth, Western Australia (strains with prefix WSM). Further strains may be found at the Global catalogue of Microorganisms: http://gcm.wfcc.info/and http://www.landcareresearch.co.nz/resources/collections/icmp and further references to strain collections and their prefixes at http://refs.wdcm.org/collections.htm.

Bacillus amyloliquefaciens subsp. plantarum MBI600 (NRRL B-50595) is deposited under accession number NRRL B-50595 with the strain designation Bacillus subtilis 1430 (and identical to NCIMB 1237). Recently, MBI 600 has been re-classified as Bacillus amyloliquefaciens subsp. plantarum based on polyphasic testing which combines classical microbiological methods relying on a mixture of traditional tools (such as culture-based methods) and molecular tools (such as genotyping and fatty acids analysis). Thus, Bacillus subtilis MBI600 (or MBI 600 or MBI-600) is identical to Bacillus amyloliquefaciens subsp. plantarum MBI600, formerly Bacillus subtilis MBI600. Bacillus amyloliquefaciens MBI600 is known as plant growth-promoting rice seed treatment from Int. J. Microbiol. Res. 3(2) (2011), 120-130 and further described e.g. in US 2012/0149571 A1. This strain MBI600 is e.g. commercially available as liquid formulation product INTEGRAL® (Becker-Underwood Inc., USA).

Bacillus subtilis strain FB17 was originally isolated from red beet roots in North America (System Appl. Microbiol 27 (2004) 372-379). This B. subtilis strain promotes plant health (US 2010/0260735 A1; WO 2011/109395 A2). B. subtilis FB17 has also been deposited at ATCC under number PTA-11857 on Apr. 26, 2011. Bacillus subtilis strain FB17 may be referred elsewhere to as UD1022 or UD10-22.

Bacillus amyloliquefaciens AP-136 (NRRL B-50614), B. amyloliquefaciens AP-188 (NRRL B-50615), B. amyloliquefaciens AP-218 (NRRL B-50618), B. amyloliquefaciens AP-219 (NRRL B-50619), B. amyloliquefaciens AP-295 (NRRL B-50620), B. japonicum SEMIA 5079 (e.g. Gelfix 5 or Adhere 60 from Nitral Urbana Laoborations, Brazil, a BASF Company), B. japonicum SEMIA 5080 (e.g. GELFIX 5 or ADHERE 60 from Nitral Urbana Laoborations, Brazil, a BASF Company), B. mojavensis AP-209 (NRRL B-50616), B. solisalsi AP-217 (NRRL B-50617), B. pumilus strain INR-7 (otherwise referred to as BU-F22 (NRRL B-50153) and BU-F33 (NRRL B-50185)), B. simplex ABU 288 (NRRL B-50340) and B. amyloliquefaciens subsp. plantarum MBI600 (NRRL B-50595) have been mentioned i.a. in US patent appl. 20120149571, U.S. Pat. No. 8,445,255, WO 2012/079073. Bradyrhizobium japonicum USDA 3 is known from U.S. Pat. No. 7,262,151. Jasmonic acid or salts (jasmonates) or derivatives include without limitation potassium jasmonate, sodium jasmonate, lithium jasmonate, ammonium jasmonate, dimethyl-ammonium jasmonate, isopropylammonium jasmonate, diolammonium jasmonate, diethtriethanolammonium jasmonate, jasmonic acid methyl ester, jasmonic acid amide, jasmonic acid methylamide, jasmonic acid-L-amino acid (amide-linked) conjugates (e.g., conjugates with L-isoleucine, L-valine, L-leucine, or L-phenylalanine), 12-oxo-phytodienoic acid, coronatine, coronafacoyl-L-serine, coronafacoyl-L-threonine, methyl esters of 1-oxo-indanoyl-isoleucine, methyl esters of 1-oxo-indanoyl-leucine, coronalon (2-[(6-ethyl-l-oxo-indane-4-carbonyl)-amino]-3-methyl-pentanoic acid methyl ester), linoleic acid or derivatives thereof and cis-jasmone, or combinations of any of the above.

Humates are humic and fulvic acids extracted from a form of lignite coal and clay, known as leonardite. Humic acids are organic acids that occur in humus and other organically derived materials such as peat and certain soft coal. They have been shown to increase fertilizer efficiency in phosphate and micro-nutrient uptake by plants as well as aiding in the development of plant root systems. Bilobalide and the ginkgolides are known components of the ginkgo tree. Bilobalide is the common name for (3aS,5aR,8aS,9R,10aR)-9-tert-butyl-8,9-dihydroxydihydro-9H-furo[2,3-b]furo[3',2'; 2,3]cyclopenta[1,2-c]furan-2,4,7(3H,8H)-trione (CAS 33570-04-6) and the following ginkgolides Ginkgolide (CAS 15291-75-5), Ginkgolide B (CAS 15291-77-7), Ginkgolide C (15291-76-6), Ginkgolide J (15291-79-9), Ginkgolide M (15291-78-8) have also been previously described and recorded. The compounds are commercially available, or can be obtained, preferably from ginkgo leaves by methods known in the art and described e.g. in U.S. Pat. No. 5,700,468, EP-A 360 556, EP-A 0 431 535 and JP-A 09-110713. Further, the compounds Bilobalide (in enantiopure form), Ginkgolide A (in its racemic form) and Ginkgolide B (in its racemic form) can be obtained by chemical synthesis, as disclosed e.g. in Tetrahedron Letters (1988), 29(28), 3423-6, Tetrahedron Letters (1988), 29(26), 3205-6 and Journal of the American Chemical Society (2000), 122(35), 8453-8463, respectively.

MIXTURE EXAMPLES

Examples of some mixtures according to the present invention are described in the tables hereinbelow.

The agriculturally active component II, with which the compound of formula I can be combined, is an insecticide or a fungicide as identified and abbreviated according to the codes listed in table B.

TABLE B

| Component II | Abbr. |
|---|---|
| Azoxystrobin | II-F-1 |
| Trifloxistrobin | II-F-2 |
| Picoxystrobin | II-F-3 |
| Pyraclostrobin | II-F-4 |
| Sedaxane | II-F-5 |
| Penthiopyrad | II-F-6 |
| Penflufen | II-F-7 |
| Fluopyram | II-F-8 |
| Fluxapyroxad | II-F-9 |
| Boscalid | II-F-10 |
| Oxathiapiprolin | II-F-11 |
| Metalaxyl | II-F-12 |
| Metalaxyl-M | II-F-13 |
| Ethaboxam | II-F-14 |
| Dimethomorph | II-F-15 |
| Valifenalate | II-F-16 |
| Cyproconazole | II-F-17 |
| Difenoconazole | II-F-18 |
| Prothioconazole | II-F-19 |
| Flutriafol | II-F-20 |
| Thiabendazole | II-F-21 |
| Ipconazole | II-F-22 |
| Tebuconazole | II-F-23 |
| Triadimenol | II-F-24 |
| Prochloraz | II-F-25 |
| Fluquinconazole | II-F-26 |
| Triticonazole | II-F-27 |
| Fludioxinil | II-F-28 |
| Carboxin | II-F-29 |
| Silthiofam | II-F-30 |
| Ziram | II-F-31 |
| Thiram | II-F-32 |
| Carbendazim | II-F-33 |
| thiophanate methyl | II-F-34 |
| Fipronil | II-I-1 |
| Clothianidin | II-I-2 |
| Thiamethoxam | II-I-3 |
| Acetamiprid | II-I-4 |
| Dinotefuran | II-I-5 |
| Imidacloprid | II-I-6 |
| Thiacloprid | II-I-7 |
| Sulfoxaflor | II-I-8 |
| Methiocarb | II-I-9 |
| Tefluthrin | II-I-10 |
| Bifenthrin | II-I-11 |
| Cypermethrin | II-I-12 |
| Alphacypermethrin | II-I-13 |
| Spinosad | II-I-14 |
| cyantraniliprole | II-I-15 |
| Chlorantraniliprole | II-I-16 |
| Thiodicarb | II-I-17 |
| Triflumezopyrim (Mesoionic) | II-I-18 |
| Acephate | II-I-19 |
| chlorpyrifos | II-I-20 |
| Flupyradifurone | II-I-21 |
| Abamectin | II-I-22 |

In certain embodiments, the present invention relates to mixtures comprising the compound of formula (I) and at least one further agriculturally active component II, such as an insecticide or a fungicide of table B.

Thus, the mixtures comprise compound of formula (I) and a further agriculturally active component II of Table B.

Thus, in the context of the present invention, each of the rows of Table B-1 corresponds to one mixture of compound I (of formula (I)) to be applied in the methods according to the present invention.

TABLE B-1

| Mixture No. | Comp. I | Comp. II |
|---|---|---|
| M.B1.1 | I | II-F-1 |
| M.B1.2 | I | II-F-2 |
| M.B1.3 | I | II-F-3 |
| M.B1.4 | I | II-F-4 |
| M.B1.5 | I | II-F-5 |
| M.B1.6 | I | II-F-6 |
| M.B1.7 | I | II-F-7 |
| M.B1.8 | I | II-F-8 |
| M.B1.9 | I | II-F-9 |
| M.B1.10 | I | II-F-10 |
| M.B1.11 | I | II-F-11 |
| M.B1.12 | I | II-F-12 |
| M.B1.13 | I | II-F-13 |
| M.B1.14 | I | II-F-14 |
| M.B1.15 | I | II-F-15 |
| M.B1.16 | I | II-F-16 |
| M.B1.17 | I | II-F-17 |
| M.B1.18 | I | II-F-18 |
| M.B1.19 | I | II-F-19 |
| M.B1.20 | I | II-F-20 |
| M.B1.21 | I | II-F-21 |
| M.B1.22 | I | II-F-22 |
| M.B1.23 | I | II-F-23 |
| M.B1.24 | I | II-F-24 |
| M.B1.25 | I | II-F-25 |
| M.B1.26 | I | II-F-26 |
| M.B1.27 | I | II-F-27 |
| M.B1.28 | I | II-F-28 |
| M.B1.29 | I | II-F-29 |
| M.B1.30 | I | II-F-30 |
| M.B1.31 | I | II-F-31 |
| M.B1.32 | I | II-F-32 |
| M.B1.33 | I | II-F-33 |
| M.B1.34 | I | II-F-34 |
| M.B1.35 | I | II-I-1 |
| M.B1.36 | I | II-I-2 |
| M.B1.37 | I | II-I-3 |
| M.B1.38 | I | II-I-4 |
| M.B1.39 | I | II-I-5 |
| M.B1.40 | I | II-I-6 |
| M.B1.41 | I | II-I-7 |
| M.B1.42 | I | II-I-8 |
| M.B1.43 | I | II-I-9 |
| M.B1.44 | I | II-I-10 |
| M.B1.45 | I | II-I-11 |
| M.B1.46 | I | II-I-12 |
| M.B1.47 | I | II-I-13 |
| M.B1.48 | I | II-I-14 |
| M.B1.49 | I | II-I-15 |
| M.B1.50 | I | II-I-16 |
| M.B1.51 | I | II-I-17 |
| M.B1.52 | I | II-I-18 |
| M.B1.53 | I | II-I-19 |
| M.B1.54 | I | II-I-20 |
| M.B1.55 | I | II-I-21 |
| M.B1.56 | I | II-I-22 |

In another embodiment of the present invention, the mixtures comprise the compound of formula (I) and two agriculturally active components (active compound II and active compound III) selected from the compounds listed in Table B.

Thus, in this further embodiment, the mixtures comprise compound of formula (I) and two fungicides or two insecticides or compound of formula (I) and one fungicide and one insecticide, selected from table B.

Thus, in the context of the present invention, each of the rows of Table T-1 corresponds to one mixture of compound I (of formula I) to be applied in the methods according to the present invention.

TABLE T-1

| Mixture No. | Comp. I | Comp. II | Comp. III |
| --- | --- | --- | --- |
| M.T1.1 | I | II-F-1 | II-F-5 |
| M.T1.2 | I | II-F-1 | II-F-6 |
| M.T1.3 | I | II-F-1 | II-F-7 |
| M.T1.4 | I | II-F-1 | II-F-8 |
| M.T1.5 | I | II-F-1 | II-F-9 |
| M.T1.6 | I | II-F-1 | II-F-10 |
| M.T1.7 | I | II-F-1 | II-F-11 |
| M.T1.8 | I | II-F-1 | II-F-12 |
| M.T1.9 | I | II-F-1 | II-F-13 |
| M.T1.10 | I | II-F-1 | II-F-14 |
| M.T1.11 | I | II-F-1 | II-F-15 |
| M.T1.12 | I | II-F-1 | II-F-16 |
| M.T1.13 | I | II-F-1 | II-F-17 |
| M.T1.14 | I | II-F-1 | II-F-18 |
| M.T1.15 | I | II-F-1 | II-F-19 |
| M.T1.16 | I | II-F-1 | II-F-20 |
| M.T1.17 | I | II-F-1 | II-F-21 |
| M.T1.18 | I | II-F-1 | II-F-22 |
| M.T1.19 | I | II-F-1 | II-F-23 |
| M.T1.20 | I | II-F-1 | II-F-24 |
| M.T1.21 | I | II-F-1 | II-F-25 |
| M.T1.22 | I | II-F-1 | II-F-26 |
| M.T1.23 | I | II-F-1 | II-F-27 |
| M.T1.24 | I | II-F-1 | II-F-28 |
| M.T1.25 | I | II-F-1 | II-F-29 |
| M.T1.26 | I | II-F-1 | II-F-30 |
| M.T1.27 | I | II-F-1 | II-F-31 |
| M.T1.28 | I | II-F-1 | II-F-32 |
| M.T1.29 | I | II-F-1 | II-F-33 |
| M.T1.30 | I | II-F-1 | II-F-34 |
| M.T1.31 | I | II-F-2 | II-F-5 |
| M.T1.32 | I | II-F-2 | II-F-6 |
| M.T1.33 | I | II-F-2 | II-F-7 |
| M.T1.34 | I | II-F-2 | II-F-8 |
| M.T1.35 | I | II-F-2 | II-F-9 |
| M.T1.36 | I | II-F-2 | II-F-10 |
| M.T1.37 | I | II-F-2 | II-F-11 |
| M.T1.38 | I | II-F-2 | II-F-12 |
| M.T1.39 | I | II-F-2 | II-F-13 |
| M.T1.40 | I | II-F-2 | II-F-14 |
| M.T1.41 | I | II-F-2 | II-F-15 |
| M.T1.42 | I | II-F-2 | II-F-16 |
| M.T1.43 | I | II-F-2 | II-F-17 |
| M.T1.44 | I | II-F-2 | II-F-18 |
| M.T1.45 | I | II-F-2 | II-F-19 |
| M.T1.46 | I | II-F-2 | II-F-20 |
| M.T1.47 | I | II-F-2 | II-F-21 |
| M.T1.48 | I | II-F-2 | II-F-22 |
| M.T1.49 | I | II-F-2 | II-F-23 |
| M.T1.50 | I | II-F-2 | II-F-24 |
| M.T1.51 | I | II-F-2 | II-F-25 |
| M.T1.52 | I | II-F-2 | II-F-26 |
| M.T1.53 | I | II-F-2 | II-F-27 |
| M.T1.54 | I | II-F-2 | II-F-28 |
| M.T1.55 | I | II-F-2 | II-F-29 |
| M.T1.56 | I | II-F-2 | II-F-30 |
| M.T1.57 | I | II-F-2 | II-F-31 |
| M.T1.58 | I | II-F-2 | II-F-32 |
| M.T1.59 | I | II-F-2 | II-F-33 |
| M.T1.60 | I | II-F-2 | II-F-34 |
| M.T1.61 | I | II-F-3 | II-F-5 |
| M.T1.62 | I | II-F-3 | II-F-6 |
| M.T1.63 | I | II-F-3 | II-F-7 |
| M.T1.64 | I | II-F-3 | II-F-8 |
| M.T1.65 | I | II-F-3 | II-F-9 |
| M.T1.66 | I | II-F-3 | II-F-10 |
| M.T1.67 | I | II-F-3 | II-F-11 |
| M.T1.68 | I | II-F-3 | II-F-12 |
| M.T1.69 | I | II-F-3 | II-F-13 |
| M.T1.70 | I | II-F-3 | II-F-14 |
| M.T1.71 | I | II-F-3 | II-F-15 |
| M.T1.72 | I | II-F-3 | II-F-16 |
| M.T1.73 | I | II-F-3 | II-F-17 |
| M.T1.74 | I | II-F-3 | II-F-18 |
| M.T1.75 | I | II-F-3 | II-F-19 |
| M.T1.76 | I | II-F-3 | II-F-20 |
| M.T1.77 | I | II-F-3 | II-F-21 |
| M.T1.78 | I | II-F-3 | II-F-22 |
| M.T1.79 | I | II-F-3 | II-F-23 |
| M.T1.80 | I | II-F-3 | II-F-24 |
| M.T1.81 | I | II-F-3 | II-F-25 |
| M.T1.82 | I | II-F-3 | II-F-26 |
| M.T1.83 | I | II-F-3 | II-F-27 |
| M.T1.84 | I | II-F-3 | II-F-28 |
| M.T1.85 | I | II-F-3 | II-F-29 |
| M.T1.86 | I | II-F-3 | II-F-30 |
| M.T1.87 | I | II-F-3 | II-F-31 |
| M.T1.88 | I | II-F-3 | II-F-32 |
| M.T1.89 | I | II-F-3 | II-F-33 |
| M.T1.90 | I | II-F-3 | II-F-34 |
| M.T1.91 | I | II-F-4 | II-F-5 |
| M.T1.92 | I | II-F-4 | II-F-6 |
| M.T1.93 | I | II-F-4 | II-F-7 |
| M.T1.94 | I | II-F-4 | II-F-8 |
| M.T1.95 | I | II-F-4 | II-F-9 |
| M.T1.96 | I | II-F-4 | II-F-10 |
| M.T1.97 | I | II-F-4 | II-F-11 |
| M.T1.98 | I | II-F-4 | II-F-12 |
| M.T1.99 | I | II-F-4 | II-F-13 |
| M.T1.100 | I | II-F-4 | II-F-14 |
| M.T1.101 | I | II-F-4 | II-F-15 |
| M.T1.102 | I | II-F-4 | II-F-16 |
| M.T1.103 | I | II-F-4 | II-F-17 |
| M.T1.104 | I | II-F-4 | II-F-18 |
| M.T1.105 | I | II-F-4 | II-F-19 |
| M.T1.106 | I | II-F-4 | II-F-20 |
| M.T1.107 | I | II-F-4 | II-F-21 |
| M.T1.108 | I | II-F-4 | II-F-22 |
| M.T1.109 | I | II-F-4 | II-F-23 |
| M.T1.110 | I | II-F-4 | II-F-24 |
| M.T1.111 | I | II-F-4 | II-F-25 |
| M.T1.112 | I | II-F-4 | II-F-26 |
| M.T1.113 | I | II-F-4 | II-F-27 |
| M.T1.114 | I | II-F-4 | II-F-28 |
| M.T1.115 | I | II-F-4 | II-F-29 |
| M.T1.116 | I | II-F-4 | II-F-30 |
| M.T1.117 | I | II-F-4 | II-F-31 |
| M.T1.118 | I | II-F-4 | II-F-32 |
| M.T1.119 | I | II-F-4 | II-F-33 |
| M.T1.120 | I | II-F-4 | II-F-34 |
| M.T1.121 | I | II-F-5 | II-F-11 |
| M.T1.122 | I | II-F-5 | II-F-12 |
| M.T1.123 | I | II-F-5 | II-F-13 |
| M.T1.124 | I | II-F-5 | II-F-14 |
| M.T1.125 | I | II-F-5 | II-F-15 |
| M.T1.126 | I | II-F-5 | II-F-16 |
| M.T1.127 | I | II-F-5 | II-F-17 |
| M.T1.128 | I | II-F-5 | II-F-18 |
| M.T1.129 | I | II-F-5 | II-F-19 |
| M.T1.130 | I | II-F-5 | II-F-20 |
| M.T1.131 | I | II-F-5 | II-F-21 |
| M.T1.132 | I | II-F-5 | II-F-22 |
| M.T1.133 | I | II-F-5 | II-F-23 |
| M.T1.134 | I | II-F-5 | II-F-24 |
| M.T1.135 | I | II-F-5 | II-F-25 |
| M.T1.136 | I | II-F-5 | II-F-26 |
| M.T1.137 | I | II-F-5 | II-F-27 |
| M.T1.138 | I | II-F-5 | II-F-28 |
| M.T1.139 | I | II-F-5 | II-F-29 |
| M.T1.140 | I | II-F-5 | II-F-30 |
| M.T1.141 | I | II-F-5 | II-F-31 |
| M.T1.142 | I | II-F-5 | II-F-32 |
| M.T1.143 | I | II-F-5 | II-F-33 |
| M.T1.144 | I | II-F-5 | II-F-34 |
| M.T1.145 | I | II-F-6 | II-F-11 |
| M.T1.146 | I | II-F-6 | II-F-12 |
| M.T1.147 | I | II-F-6 | II-F-13 |
| M.T1.148 | I | II-F-6 | II-F-14 |

TABLE T-1-continued

| Mixture No. | Comp. I | Comp. II | Comp. III |
|---|---|---|---|
| M.T1.149 | I | II-F-6 | II-F-15 |
| M.T1.150 | I | II-F-6 | II-F-16 |
| M.T1.151 | I | II-F-6 | II-F-17 |
| M.T1.152 | I | II-F-6 | II-F-18 |
| M.T1.153 | I | II-F-6 | II-F-19 |
| M.T1.154 | I | II-F-6 | II-F-20 |
| M.T1.155 | I | II-F-6 | II-F-21 |
| M.T1.156 | I | II-F-6 | II-F-22 |
| M.T1.157 | I | II-F-6 | II-F-23 |
| M.T1.158 | I | II-F-6 | II-F-24 |
| M.T1.159 | I | II-F-6 | II-F-25 |
| M.T1.160 | I | II-F-6 | II-F-26 |
| M.T1.161 | I | II-F-6 | II-F-27 |
| M.T1.162 | I | II-F-6 | II-F-28 |
| M.T1.163 | I | II-F-6 | II-F-29 |
| M.T1.164 | I | II-F-6 | II-F-30 |
| M.T1.165 | I | II-F-6 | II-F-31 |
| M.T1.166 | I | II-F-6 | II-F-32 |
| M.T1.167 | I | II-F-6 | II-F-33 |
| M.T1.168 | I | II-F-6 | II-F-34 |
| M.T1.169 | I | II-F-6 | II-F-11 |
| M.T1.170 | I | II-F-6 | II-F-12 |
| M.T1.171 | I | II-F-6 | II-F-13 |
| M.T1.172 | I | II-F-6 | II-F-14 |
| M.T1.173 | I | II-F-6 | II-F-15 |
| M.T1.174 | I | II-F-6 | II-F-16 |
| M.T1.175 | I | II-F-6 | II-F-17 |
| M.T1.176 | I | II-F-6 | II-F-18 |
| M.T1.177 | I | II-F-6 | II-F-19 |
| M.T1.178 | I | II-F-6 | II-F-20 |
| M.T1.179 | I | II-F-6 | II-F-21 |
| M.T1.180 | I | II-F-6 | II-F-22 |
| M.T1.181 | I | II-F-6 | II-F-23 |
| M.T1.182 | I | II-F-6 | II-F-24 |
| M.T1.183 | I | II-F-6 | II-F-25 |
| M.T1.184 | I | II-F-6 | II-F-26 |
| M.T1.185 | I | II-F-6 | II-F-27 |
| M.T1.186 | I | II-F-6 | II-F-28 |
| M.T1.187 | I | II-F-6 | II-F-29 |
| M.T1.188 | I | II-F-6 | II-F-30 |
| M.T1.189 | I | II-F-6 | II-F-31 |
| M.T1.190 | I | II-F-6 | II-F-32 |
| M.T1.191 | I | II-F-6 | II-F-33 |
| M.T1.192 | I | II-F-6 | II-F-34 |
| M.T1.193 | I | II-F-7 | II-F-11 |
| M.T1.194 | I | II-F-7 | II-F-12 |
| M.T1.195 | I | II-F-7 | II-F-13 |
| M.T1.196 | I | II-F-7 | II-F-14 |
| M.T1.197 | I | II-F-7 | II-F-15 |
| M.T1.198 | I | II-F-7 | II-F-16 |
| M.T1.199 | I | II-F-7 | II-F-17 |
| M.T1.200 | I | II-F-7 | II-F-18 |
| M.T1.201 | I | II-F-7 | II-F-19 |
| M.T1.202 | I | II-F-7 | II-F-20 |
| M.T1.203 | I | II-F-7 | II-F-21 |
| M.T1.204 | I | II-F-7 | II-F-22 |
| M.T1.205 | I | II-F-7 | II-F-23 |
| M.T1.206 | I | II-F-7 | II-F-24 |
| M.T1.207 | I | II-F-7 | II-F-25 |
| M.T1.208 | I | II-F-7 | II-F-26 |
| M.T1.209 | I | II-F-7 | II-F-27 |
| M.T1.210 | I | II-F-7 | II-F-28 |
| M.T1.211 | I | II-F-7 | II-F-29 |
| M.T1.212 | I | II-F-7 | II-F-30 |
| M.T1.213 | I | II-F-7 | II-F-31 |
| M.T1.214 | I | II-F-7 | II-F-32 |
| M.T1.215 | I | II-F-7 | II-F-33 |
| M.T1.216 | I | II-F-7 | II-F-34 |
| M.T1.217 | I | II-F-8 | II-F-11 |
| M.T1.218 | I | II-F-8 | II-F-12 |
| M.T1.219 | I | II-F-8 | II-F-13 |
| M.T1.220 | I | II-F-8 | II-F-14 |
| M.T1.221 | I | II-F-8 | II-F-15 |
| M.T1.222 | I | II-F-8 | II-F-16 |
| M.T1.223 | I | II-F-8 | II-F-17 |
| M.T1.224 | I | II-F-8 | II-F-18 |
| M.T1.225 | I | II-F-8 | II-F-19 |
| M.T1.226 | I | II-F-8 | II-F-20 |
| M.T1.227 | I | II-F-8 | II-F-21 |
| M.T1.228 | I | II-F-8 | II-F-22 |
| M.T1.229 | I | II-F-8 | II-F-23 |
| M.T1.230 | I | II-F-8 | II-F-24 |
| M.T1.231 | I | II-F-8 | II-F-25 |
| M.T1.232 | I | II-F-8 | II-F-26 |
| M.T1.233 | I | II-F-8 | II-F-27 |
| M.T1.234 | I | II-F-8 | II-F-28 |
| M.T1.235 | I | II-F-8 | II-F-29 |
| M.T1.236 | I | II-F-8 | II-F-30 |
| M.T1.237 | I | II-F-8 | II-F-31 |
| M.T1.238 | I | II-F-8 | II-F-32 |
| M.T1.239 | I | II-F-8 | II-F-33 |
| M.T1.240 | I | II-F-8 | II-F-34 |
| M.T1.241 | I | II-F-9 | II-F-11 |
| M.T1.242 | I | II-F-9 | II-F-12 |
| M.T1.243 | I | II-F-9 | II-F-13 |
| M.T1.244 | I | II-F-9 | II-F-14 |
| M.T1.245 | I | II-F-9 | II-F-15 |
| M.T1.246 | I | II-F-9 | II-F-16 |
| M.T1.247 | I | II-F-9 | II-F-17 |
| M.T1.248 | I | II-F-9 | II-F-18 |
| M.T1.249 | I | II-F-9 | II-F-19 |
| M.T1.250 | I | II-F-9 | II-F-20 |
| M.T1.251 | I | II-F-9 | II-F-21 |
| M.T1.252 | I | II-F-9 | II-F-22 |
| M.T1.253 | I | II-F-9 | II-F-23 |
| M.T1.254 | I | II-F-9 | II-F-24 |
| M.T1.255 | I | II-F-9 | II-F-25 |
| M.T1.256 | I | II-F-9 | II-F-26 |
| M.T1.257 | I | II-F-9 | II-F-27 |
| M.T1.258 | I | II-F-9 | II-F-28 |
| M.T1.259 | I | II-F-9 | II-F-29 |
| M.T1.260 | I | II-F-9 | II-F-30 |
| M.T1.261 | I | II-F-9 | II-F-31 |
| M.T1.262 | I | II-F-9 | II-F-32 |
| M.T1.263 | I | II-F-9 | II-F-33 |
| M.T1.264 | I | II-F-9 | II-F-34 |
| M.T1.265 | I | II-F-10 | II-F-11 |
| M.T1.266 | I | II-F-10 | II-F-12 |
| M.T1.267 | I | II-F-10 | II-F-13 |
| M.T1.268 | I | II-F-10 | II-F-14 |
| M.T1.269 | I | II-F-10 | II-F-15 |
| M.T1.270 | I | II-F-10 | II-F-16 |
| M.T1.271 | I | II-F-10 | II-F-17 |
| M.T1.272 | I | II-F-10 | II-F-18 |
| M.T1.273 | I | II-F-10 | II-F-19 |
| M.T1.274 | I | II-F-10 | II-F-20 |
| M.T1.275 | I | II-F-10 | II-F-21 |
| M.T1.276 | I | II-F-10 | II-F-22 |
| M.T1.277 | I | II-F-10 | II-F-23 |
| M.T1.278 | I | II-F-10 | II-F-24 |
| M.T1.279 | I | II-F-10 | II-F-25 |
| M.T1.280 | I | II-F-10 | II-F-26 |
| M.T1.281 | I | II-F-10 | II-F-27 |
| M.T1.282 | I | II-F-10 | II-F-28 |
| M.T1.283 | I | II-F-10 | II-F-29 |
| M.T1.284 | I | II-F-10 | II-F-30 |
| M.T1.285 | I | II-F-10 | II-F-31 |
| M.T1.286 | I | II-F-10 | II-F-32 |
| M.T1.287 | I | II-F-10 | II-F-33 |
| M.T1.288 | I | II-F-10 | II-F-34 |
| M.T1.289 | I | II-F-11 | II-F-17 |
| M.T1.290 | I | II-F-11 | II-F-18 |
| M.T1.291 | I | II-F-11 | II-F-19 |
| M.T1.292 | I | II-F-11 | II-F-20 |
| M.T1.293 | I | II-F-11 | II-F-21 |
| M.T1.294 | I | II-F-11 | II-F-22 |
| M.T1.295 | I | II-F-11 | II-F-23 |
| M.T1.296 | I | II-F-11 | II-F-24 |
| M.T1.297 | I | II-F-11 | II-F-25 |
| M.T1.298 | I | II-F-11 | II-F-26 |
| M.T1.299 | I | II-F-11 | II-F-27 |
| M.T1.300 | I | II-F-11 | II-F-28 |
| M.T1.301 | I | II-F-11 | II-F-29 |
| M.T1.302 | I | II-F-11 | II-F-30 |

TABLE T-1-continued

| Mixture No. | Comp. I | Comp. II | Comp. III |
|---|---|---|---|
| M.T1.303 | I | II-F-11 | II-F-31 |
| M.T1.304 | I | II-F-11 | II-F-32 |
| M.T1.305 | I | II-F-11 | II-F-33 |
| M.T1.306 | I | II-F-11 | II-F-34 |
| M.T1.307 | I | II-F-12 | II-F-17 |
| M.T1.308 | I | II-F-12 | II-F-18 |
| M.T1.309 | I | II-F-12 | II-F-19 |
| M.T1.310 | I | II-F-12 | II-F-20 |
| M.T1.311 | I | II-F-12 | II-F-21 |
| M.T1.312 | I | II-F-12 | II-F-22 |
| M.T1.313 | I | II-F-12 | II-F-23 |
| M.T1.314 | I | II-F-12 | II-F-24 |
| M.T1.315 | I | II-F-12 | II-F-25 |
| M.T1.316 | I | II-F-12 | II-F-26 |
| M.T1.317 | I | II-F-12 | II-F-27 |
| M.T1.318 | I | II-F-12 | II-F-28 |
| M.T1.319 | I | II-F-12 | II-F-29 |
| M.T1.320 | I | II-F-12 | II-F-30 |
| M.T1.321 | I | II-F-12 | II-F-31 |
| M.T1.322 | I | II-F-12 | II-F-32 |
| M.T1.323 | I | II-F-12 | II-F-33 |
| M.T1.324 | I | II-F-12 | II-F-34 |
| M.T1.325 | I | II-F-13 | II-F-17 |
| M.T1.326 | I | II-F-13 | II-F-18 |
| M.T1.327 | I | II-F-13 | II-F-19 |
| M.T1.328 | I | II-F-13 | II-F-20 |
| M.T1.329 | I | II-F-13 | II-F-21 |
| M.T1.330 | I | II-F-13 | II-F-22 |
| M.T1.331 | I | II-F-13 | II-F-23 |
| M.T1.332 | I | II-F-13 | II-F-24 |
| M.T1.333 | I | II-F-13 | II-F-25 |
| M.T1.334 | I | II-F-13 | II-F-26 |
| M.T1.335 | I | II-F-13 | II-F-27 |
| M.T1.336 | I | II-F-13 | II-F-28 |
| M.T1.337 | I | II-F-13 | II-F-29 |
| M.T1.338 | I | II-F-13 | II-F-30 |
| M.T1.339 | I | II-F-13 | II-F-31 |
| M.T1.340 | I | II-F-13 | II-F-32 |
| M.T1.341 | I | II-F-13 | II-F-33 |
| M.T1.342 | I | II-F-13 | II-F-34 |
| M.T1.343 | I | II-F-14 | II-F-17 |
| M.T1.344 | I | II-F-14 | II-F-18 |
| M.T1.345 | I | II-F-14 | II-F-19 |
| M.T1.346 | I | II-F-14 | II-F-20 |
| M.T1.347 | I | II-F-14 | II-F-21 |
| M.T1.348 | I | II-F-14 | II-F-22 |
| M.T1.349 | I | II-F-14 | II-F-23 |
| M.T1.350 | I | II-F-14 | II-F-24 |
| M.T1.351 | I | II-F-14 | II-F-25 |
| M.T1.352 | I | II-F-14 | II-F-26 |
| M.T1.353 | I | II-F-14 | II-F-27 |
| M.T1.354 | I | II-F-14 | II-F-28 |
| M.T1.355 | I | II-F-14 | II-F-29 |
| M.T1.356 | I | II-F-14 | II-F-30 |
| M.T1.357 | I | II-F-14 | II-F-31 |
| M.T1.358 | I | II-F-14 | II-F-32 |
| M.T1.359 | I | II-F-14 | II-F-33 |
| M.T1.360 | I | II-F-14 | II-F-34 |
| M.T1.361 | I | II-F-15 | II-F-17 |
| M.T1.362 | I | II-F-15 | II-F-18 |
| M.T1.363 | I | II-F-15 | II-F-19 |
| M.T1.364 | I | II-F-15 | II-F-20 |
| M.T1.365 | I | II-F-15 | II-F-21 |
| M.T1.366 | I | II-F-15 | II-F-22 |
| M.T1.367 | I | II-F-15 | II-F-23 |
| M.T1.368 | I | II-F-15 | II-F-24 |
| M.T1.369 | I | II-F-15 | II-F-25 |
| M.T1.370 | I | II-F-15 | II-F-26 |
| M.T1.371 | I | II-F-15 | II-F-27 |
| M.T1.372 | I | II-F-15 | II-F-28 |
| M.T1.373 | I | II-F-15 | II-F-29 |
| M.T1.374 | I | II-F-15 | II-F-30 |
| M.T1.375 | I | II-F-15 | II-F-31 |
| M.T1.376 | I | II-F-15 | II-F-32 |
| M.T1.377 | I | II-F-15 | II-F-33 |
| M.T1.378 | I | II-F-15 | II-F-34 |
| M.T1.379 | I | II-F-16 | II-F-17 |
| M.T1.380 | I | II-F-16 | II-F-18 |
| M.T1.381 | I | II-F-16 | II-F-19 |
| M.T1.382 | I | II-F-16 | II-F-20 |
| M.T1.383 | I | II-F-16 | II-F-21 |
| M.T1.384 | I | II-F-16 | II-F-22 |
| M.T1.385 | I | II-F-16 | II-F-23 |
| M.T1.386 | I | II-F-16 | II-F-24 |
| M.T1.387 | I | II-F-16 | II-F-25 |
| M.T1.388 | I | II-F-16 | II-F-26 |
| M.T1.389 | I | II-F-16 | II-F-27 |
| M.T1.390 | I | II-F-16 | II-F-28 |
| M.T1.391 | I | II-F-16 | II-F-29 |
| M.T1.392 | I | II-F-16 | II-F-30 |
| M.T1.393 | I | II-F-16 | II-F-31 |
| M.T1.394 | I | II-F-16 | II-F-32 |
| M.T1.395 | I | II-F-16 | II-F-33 |
| M.T1.396 | I | II-F-16 | II-F-34 |
| M.T1.397 | I | II-F-17 | II-F-28 |
| M.T1.398 | I | II-F-17 | II-F-29 |
| M.T1.399 | I | II-F-17 | II-F-30 |
| M.T1.400 | I | II-F-17 | II-F-31 |
| M.T1.401 | I | II-F-17 | II-F-32 |
| M.T1.402 | I | II-F-17 | II-F-33 |
| M.T1.403 | I | II-F-17 | II-F-34 |
| M.T1.404 | I | II-F-18 | II-F-28 |
| M.T1.405 | I | II-F-18 | II-F-29 |
| M.T1.406 | I | II-F-18 | II-F-30 |
| M.T1.407 | I | II-F-18 | II-F-31 |
| M.T1.408 | I | II-F-18 | II-F-32 |
| M.T1.409 | I | II-F-18 | II-F-33 |
| M.T1.410 | I | II-F-18 | II-F-34 |
| M.T1.411 | I | II-F-19 | II-F-28 |
| M.T1.412 | I | II-F-19 | II-F-29 |
| M.T1.413 | I | II-F-19 | II-F-30 |
| M.T1.414 | I | II-F-19 | II-F-31 |
| M.T1.415 | I | II-F-19 | II-F-32 |
| M.T1.416 | I | II-F-19 | II-F-33 |
| M.T1.417 | I | II-F-19 | II-F-34 |
| M.T1.418 | I | II-F-20 | II-F-28 |
| M.T1.419 | I | II-F-20 | II-F-29 |
| M.T1.420 | I | II-F-20 | II-F-30 |
| M.T1.421 | I | II-F-20 | II-F-31 |
| M.T1.422 | I | II-F-20 | II-F-32 |
| M.T1.423 | I | II-F-20 | II-F-33 |
| M.T1.424 | I | II-F-20 | II-F-34 |
| M.T1.425 | I | II-F-21 | II-F-28 |
| M.T1.426 | I | II-F-21 | II-F-29 |
| M.T1.427 | I | II-F-21 | II-F-30 |
| M.T1.428 | I | II-F-21 | II-F-31 |
| M.T1.429 | I | II-F-21 | II-F-32 |
| M.T1.430 | I | II-F-21 | II-F-33 |
| M.T1.431 | I | II-F-21 | II-F-34 |
| M.T1.432 | I | II-F-22 | II-F-28 |
| M.T1.433 | I | II-F-22 | II-F-29 |
| M.T1.434 | I | II-F-22 | II-F-30 |
| M.T1.435 | I | II-F-22 | II-F-31 |
| M.T1.436 | I | II-F-22 | II-F-32 |
| M.T1.437 | I | II-F-22 | II-F-33 |
| M.T1.438 | I | II-F-22 | II-F-34 |
| M.T1.439 | I | II-F-23 | II-F-28 |
| M.T1.440 | I | II-F-23 | II-F-29 |
| M.T1.441 | I | II-F-23 | II-F-30 |
| M.T1.442 | I | II-F-23 | II-F-31 |
| M.T1.443 | I | II-F-23 | II-F-32 |
| M.T1.444 | I | II-F-23 | II-F-33 |
| M.T1.445 | I | II-F-23 | II-F-34 |
| M.T1.446 | I | II-F-24 | II-F-28 |
| M.T1.447 | I | II-F-24 | II-F-29 |
| M.T1.448 | I | II-F-24 | II-F-30 |
| M.T1.449 | I | II-F-24 | II-F-31 |
| M.T1.450 | I | II-F-24 | II-F-32 |
| M.T1.451 | I | II-F-24 | II-F-33 |
| M.T1.452 | I | II-F-24 | II-F-34 |
| M.T1.453 | I | II-F-25 | II-F-28 |
| M.T1.454 | I | II-F-25 | II-F-29 |
| M.T1.455 | I | II-F-25 | II-F-30 |
| M.T1.456 | I | II-F-25 | II-F-31 |

TABLE T-1-continued

| Mixture No. | Comp. I | Comp. II | Comp. III |
|---|---|---|---|
| M.T1.457 | I | II-F-25 | II-F-32 |
| M.T1.458 | I | II-F-25 | II-F-33 |
| M.T1.459 | I | II-F-25 | II-F-34 |
| M.T1.460 | I | II-F-26 | II-F-28 |
| M.T1.461 | I | II-F-26 | II-F-29 |
| M.T1.462 | I | II-F-26 | II-F-30 |
| M.T1.463 | I | II-F-26 | II-F-31 |
| M.T1.464 | I | II-F-26 | II-F-32 |
| M.T1.465 | I | II-F-26 | II-F-33 |
| M.T1.466 | I | II-F-26 | II-F-34 |
| M.T1.467 | I | II-F-27 | II-F-28 |
| M.T1.468 | I | II-F-27 | II-F-29 |
| M.T1.469 | I | II-F-27 | II-F-30 |
| M.T1.470 | I | II-F-27 | II-F-31 |
| M.T1.471 | I | II-F-27 | II-F-32 |
| M.T1.472 | I | II-F-27 | II-F-33 |
| M.T1.473 | I | II-F-27 | II-F-34 |
| M.T1.474 | I | II-F-28 | II-F-29 |
| M.T1.475 | I | II-F-28 | II-F-30 |
| M.T1.476 | I | II-F-28 | II-F-31 |
| M.T1.477 | I | II-F-28 | II-F-32 |
| M.T1.478 | I | II-F-28 | II-F-33 |
| M.T1.479 | I | II-F-28 | II-F-34 |
| M.T1.480 | I | II-F-30 | II-F-29 |
| M.T1.481 | I | II-F-30 | II-F-31 |
| M.T1.482 | I | II-F-30 | II-F-32 |
| M.T1.483 | I | II-F-30 | II-F-33 |
| M.T1.484 | I | II-F-30 | II-F-34 |
| M.T1.485 | I | II-F-29 | II-F-31 |
| M.T1.486 | I | II-F-29 | II-F-32 |
| M.T1.487 | I | II-F-29 | II-F-33 |
| M.T1.488 | I | II-F-29 | II-F-34 |
| M.T1.489 | I | II-I-1 | II-F-1 |
| M.T1.490 | I | II-I-1 | II-F-2 |
| M.T1.491 | I | II-I-1 | II-F-3 |
| M.T1.492 | I | II-I-1 | II-F-4 |
| M.T1.493 | I | II-I-1 | II-F-5 |
| M.T1.494 | I | II-I-1 | II-F-6 |
| M.T1.495 | I | II-I-1 | II-F-7 |
| M.T1.496 | I | II-I-1 | II-F-8 |
| M.T1.497 | I | II-I-1 | II-F-9 |
| M.T1.498 | I | II-I-1 | II-F-10 |
| M.T1.499 | I | II-I-1 | II-F-11 |
| M.T1.500 | I | II-I-1 | II-F-12 |
| M.T1.501 | I | II-I-1 | II-F-13 |
| M.T1.502 | I | II-I-1 | II-F-14 |
| M.T1.503 | I | II-I-1 | II-F-15 |
| M.T1.504 | I | II-I-1 | II-F-16 |
| M.T1.505 | I | II-I-1 | II-F-17 |
| M.T1.506 | I | II-I-1 | II-F-18 |
| M.T1.507 | I | II-I-1 | II-F-19 |
| M.T1.508 | I | II-I-1 | II-F-20 |
| M.T1.509 | I | II-I-1 | II-F-21 |
| M.T1.510 | I | II-I-1 | II-F-22 |
| M.T1.511 | I | II-I-1 | II-F-23 |
| M.T1.512 | I | II-I-1 | II-F-24 |
| M.T1.513 | I | II-I-1 | II-F-25 |
| M.T1.514 | I | II-I-1 | II-F-26 |
| M.T1.515 | I | II-I-1 | II-F-27 |
| M.T1.516 | I | II-I-1 | II-F-28 |
| M.T1.517 | I | II-I-1 | II-F-29 |
| M.T1.518 | I | II-I-1 | II-F-30 |
| M.T1.519 | I | II-I-1 | II-F-31 |
| M.T1.520 | I | II-I-1 | II-F-32 |
| M.T1.521 | I | II-I-1 | II-F-33 |
| M.T1.522 | I | II-I-1 | II-F-34 |
| M.T1.523 | I | II-I-1 | II-I-22 |
| M.T1.524 | I | II-I-2 | II-F-1 |
| M.T1.525 | I | II-I-2 | II-F-2 |
| M.T1.526 | I | II-I-2 | II-F-3 |
| M.T1.527 | I | II-I-2 | II-F-4 |
| M.T1.528 | I | II-I-2 | II-F-5 |
| M.T1.529 | I | II-I-2 | II-F-6 |
| M.T1.530 | I | II-I-2 | II-F-7 |
| M.T1.531 | I | II-I-2 | II-F-8 |
| M.T1.532 | I | II-I-2 | II-F-9 |
| M.T1.533 | I | II-I-2 | II-F-10 |
| M.T1.534 | I | II-I-2 | II-F-11 |
| M.T1.535 | I | II-I-2 | II-F-12 |
| M.T1.536 | I | II-I-2 | II-F-13 |
| M.T1.537 | I | II-I-2 | II-F-14 |
| M.T1.538 | I | II-I-2 | II-F-15 |
| M.T1.539 | I | II-I-2 | II-F-16 |
| M.T1.540 | I | II-I-2 | II-F-17 |
| M.T1.541 | I | II-I-2 | II-F-18 |
| M.T1.542 | I | II-I-2 | II-F-19 |
| M.T1.543 | I | II-I-2 | II-F-20 |
| M.T1.544 | I | II-I-2 | II-F-21 |
| M.T1.545 | I | II-I-2 | II-F-22 |
| M.T1.546 | I | II-I-2 | II-F-23 |
| M.T1.547 | I | II-I-2 | II-F-24 |
| M.T1.548 | I | II-I-2 | II-F-25 |
| M.T1.549 | I | II-I-2 | II-F-26 |
| M.T1.550 | I | II-I-2 | II-F-27 |
| M.T1.551 | I | II-I-2 | II-F-28 |
| M.T1.552 | I | II-I-2 | II-F-29 |
| M.T1.553 | I | II-I-2 | II-F-30 |
| M.T1.554 | I | II-I-2 | II-F-31 |
| M.T1.555 | I | II-I-2 | II-F-32 |
| M.T1.556 | I | II-I-2 | II-F-33 |
| M.T1.557 | I | II-I-2 | II-F-34 |
| M.T1.558 | I | II-I-2 | II-I-22 |
| M.T1.559 | I | II-I-3 | II-F-1 |
| M.T1.560 | I | II-I-3 | II-F-2 |
| M.T1.561 | I | II-I-3 | II-F-3 |
| M.T1.562 | I | II-I-3 | II-F-4 |
| M.T1.563 | I | II-I-3 | II-F-5 |
| M.T1.564 | I | II-I-3 | II-F-6 |
| M.T1.565 | I | II-I-3 | II-F-7 |
| M.T1.566 | I | II-I-3 | II-F-8 |
| M.T1.567 | I | II-I-3 | II-F-9 |
| M.T1.568 | I | II-I-3 | II-F-10 |
| M.T1.569 | I | II-I-3 | II-F-11 |
| M.T1.570 | I | II-I-3 | II-F-12 |
| M.T1.571 | I | II-I-3 | II-F-13 |
| M.T1.572 | I | II-I-3 | II-F-14 |
| M.T1.573 | I | II-I-3 | II-F-15 |
| M.T1.574 | I | II-I-3 | II-F-16 |
| M.T1.575 | I | II-I-3 | II-F-17 |
| M.T1.576 | I | II-I-3 | II-F-18 |
| M.T1.577 | I | II-I-3 | II-F-19 |
| M.T1.578 | I | II-I-3 | II-F-20 |
| M.T1.579 | I | II-I-3 | II-F-21 |
| M.T1.580 | I | II-I-3 | II-F-22 |
| M.T1.581 | I | II-I-3 | II-F-23 |
| M.T1.582 | I | II-I-3 | II-F-24 |
| M.T1.583 | I | II-I-3 | II-F-25 |
| M.T1.584 | I | II-I-3 | II-F-26 |
| M.T1.585 | I | II-I-3 | II-F-27 |
| M.T1.586 | I | II-I-3 | II-F-28 |
| M.T1.587 | I | II-I-3 | II-F-29 |
| M.T1.588 | I | II-I-3 | II-F-30 |
| M.T1.589 | I | II-I-3 | II-F-31 |
| M.T1.590 | I | II-I-3 | II-F-32 |
| M.T1.591 | I | II-I-3 | II-F-33 |
| M.T1.592 | I | II-I-3 | II-F-34 |
| M.T1.593 | I | II-I-3 | II-I-22 |
| M.T1.594 | I | II-I-4 | II-F-1 |
| M.T1.595 | I | II-I-4 | II-F-2 |
| M.T1.596 | I | II-I-4 | II-F-3 |
| M.T1.597 | I | II-I-4 | II-F-4 |
| M.T1.598 | I | II-I-4 | II-F-5 |
| M.T1.599 | I | II-I-4 | II-F-6 |
| M.T1.600 | I | II-I-4 | II-F-7 |
| M.T1.601 | I | II-I-4 | II-F-8 |
| M.T1.602 | I | II-I-4 | II-F-9 |
| M.T1.603 | I | II-I-4 | II-F-10 |
| M.T1.604 | I | II-I-4 | II-F-11 |
| M.T1.605 | I | II-I-4 | II-F-12 |
| M.T1.606 | I | II-I-4 | II-F-13 |
| M.T1.607 | I | II-I-4 | II-F-14 |
| M.T1.608 | I | II-I-4 | II-F-15 |
| M.T1.609 | I | II-I-4 | II-F-16 |
| M.T1.610 | I | II-I-4 | II-F-17 |

TABLE T-1-continued

| Mixture No. | Comp. I | Comp. II | Comp. III |
|---|---|---|---|
| M.T1.611 | I | II-I-4 | II-F-18 |
| M.T1.612 | I | II-I-4 | II-F-19 |
| M.T1.613 | I | II-I-4 | II-F-20 |
| M.T1.614 | I | II-I-4 | II-F-21 |
| M.T1.615 | I | II-I-4 | II-F-22 |
| M.T1.616 | I | II-I-4 | II-F-23 |
| M.T1.617 | I | II-I-4 | II-F-24 |
| M.T1.618 | I | II-I-4 | II-F-25 |
| M.T1.619 | I | II-I-4 | II-F-26 |
| M.T1.620 | I | II-I-4 | II-F-27 |
| M.T1.621 | I | II-I-4 | II-F-28 |
| M.T1.622 | I | II-I-4 | II-F-29 |
| M.T1.623 | I | II-I-4 | II-F-30 |
| M.T1.624 | I | II-I-4 | II-F-31 |
| M.T1.625 | I | II-I-4 | II-F-32 |
| M.T1.626 | I | II-I-4 | II-F-33 |
| M.T1.627 | I | II-I-4 | II-F-34 |
| M.T1.628 | I | II-I-4 | II-1-22 |
| M.T1.629 | I | II-I-5 | II-F-1 |
| M.T1.630 | I | II-I-5 | II-F-2 |
| M.T1.631 | I | II-I-5 | II-F-3 |
| M.T1.632 | I | II-I-5 | II-F-4 |
| M.T1.633 | I | II-I-5 | II-F-5 |
| M.T1.634 | I | II-I-5 | II-F-6 |
| M.T1.635 | I | II-I-5 | II-F-7 |
| M.T1.636 | I | II-I-5 | II-F-8 |
| M.T1.637 | I | II-I-5 | II-F-9 |
| M.T1.638 | I | II-I-5 | II-F-10 |
| M.T1.639 | I | II-I-5 | II-F-11 |
| M.T1.640 | I | II-I-5 | II-F-12 |
| M.T1.641 | I | II-I-5 | II-F-13 |
| M.T1.642 | I | II-I-5 | II-F-14 |
| M.T1.643 | I | II-I-5 | II-F-15 |
| M.T1.644 | I | II-I-5 | II-F-16 |
| M.T1.645 | I | II-I-5 | II-F-17 |
| M.T1.646 | I | II-I-5 | II-F-18 |
| M.T1.647 | I | II-I-5 | II-F-19 |
| M.T1.648 | I | II-I-5 | II-F-20 |
| M.T1.649 | I | II-I-5 | II-F-21 |
| M.T1.650 | I | II-I-5 | II-F-22 |
| M.T1.651 | I | II-I-5 | II-F-23 |
| M.T1.652 | I | II-I-5 | II-F-24 |
| M.T1.653 | I | II-I-5 | II-F-25 |
| M.T1.654 | I | II-I-5 | II-F-26 |
| M.T1.655 | I | II-I-5 | II-F-27 |
| M.T1.656 | I | II-I-5 | II-F-28 |
| M.T1.657 | I | II-I-5 | II-F-29 |
| M.T1.658 | I | II-I-5 | II-F-30 |
| M.T1.659 | I | II-I-5 | II-F-31 |
| M.T1.660 | I | II-I-5 | II-F-32 |
| M.T1.661 | I | II-I-5 | II-F-33 |
| M.T1.662 | I | II-I-5 | II-F-34 |
| M.T1.663 | I | II-I-5 | II-I-22 |
| M.T1.664 | I | II-I-6 | II-F-1 |
| M.T1.665 | I | II-I-6 | II-F-2 |
| M.T1.666 | I | II-I-6 | II-F-3 |
| M.T1.667 | I | II-I-6 | II-F-4 |
| M.T1.668 | I | II-I-6 | II-F-5 |
| M.T1.669 | I | II-I-6 | II-F-6 |
| M.T1.670 | I | II-I-6 | II-F-7 |
| M.T1.671 | I | II-I-6 | II-F-8 |
| M.T1.672 | I | II-I-6 | II-F-9 |
| M.T1.673 | I | II-I-6 | II-F-10 |
| M.T1.674 | I | II-I-6 | II-F-11 |
| M.T1.675 | I | II-I-6 | II-F-12 |
| M.T1.676 | I | II-I-6 | II-F-13 |
| M.T1.677 | I | II-I-6 | II-F-14 |
| M.T1.678 | I | II-I-6 | II-F-15 |
| M.T1.679 | I | II-I-6 | II-F-16 |
| M.T1.680 | I | II-I-6 | II-F-17 |
| M.T1.681 | I | II-I-6 | II-F-18 |
| M.T1.682 | I | II-I-6 | II-F-19 |
| M.T1.683 | I | II-I-6 | II-F-20 |
| M.T1.684 | I | II-I-6 | II-F-21 |
| M.T1.685 | I | II-I-6 | II-F-22 |
| M.T1.686 | I | II-I-6 | II-F-23 |
| M.T1.687 | I | II-I-6 | II-F-24 |
| M.T1.688 | I | II-I-6 | II-F-25 |
| M.T1.689 | I | II-I-6 | II-F-26 |
| M.T1.690 | I | II-I-6 | II-F-27 |
| M.T1.691 | I | II-I-6 | II-F-28 |
| M.T1.692 | I | II-I-6 | II-F-29 |
| M.T1.693 | I | II-I-6 | II-F-30 |
| M.T1.694 | I | II-I-6 | II-F-31 |
| M.T1.695 | I | II-I-6 | II-F-32 |
| M.T1.696 | I | II-I-6 | II-F-33 |
| M.T1.697 | I | II-I-6 | II-F-34 |
| M.T1.698 | I | II-I-6 | II-I-22 |
| M.T1.699 | I | II-I-7 | II-F-1 |
| M.T1.700 | I | II-I-7 | II-F-2 |
| M.T1.701 | I | II-I-7 | II-F-3 |
| M.T1.702 | I | II-I-7 | II-F-4 |
| M.T1.703 | I | II-I-7 | II-F-5 |
| M.T1.704 | I | II-I-7 | II-F-6 |
| M.T1.705 | I | II-I-7 | II-F-7 |
| M.T1.706 | I | II-I-7 | II-F-8 |
| M.T1.707 | I | II-I-7 | II-F-9 |
| M.T1.708 | I | II-I-7 | II-F-10 |
| M.T1.709 | I | II-I-7 | II-F-11 |
| M.T1.710 | I | II-I-7 | II-F-12 |
| M.T1.711 | I | II-I-7 | II-F-13 |
| M.T1.712 | I | II-I-7 | II-F-14 |
| M.T1.713 | I | II-I-7 | II-F-15 |
| M.T1.714 | I | II-I-7 | II-F-16 |
| M.T1.715 | I | II-I-7 | II-F-17 |
| M.T1.716 | I | II-I-7 | II-F-18 |
| M.T1.717 | I | II-I-7 | II-F-19 |
| M.T1.718 | I | II-I-7 | II-F-20 |
| M.T1.719 | I | II-I-7 | II-F-21 |
| M.T1.720 | I | II-I-7 | II-F-22 |
| M.T1.721 | I | II-I-7 | II-F-23 |
| M.T1.722 | I | II-I-7 | II-F-24 |
| M.T1.723 | I | II-I-7 | II-F-25 |
| M.T1.724 | I | II-I-7 | II-F-26 |
| M.T1.725 | I | II-I-7 | II-F-27 |
| M.T1.726 | I | II-I-7 | II-F-28 |
| M.T1.727 | I | II-I-7 | II-F-29 |
| M.T1.728 | I | II-I-7 | II-F-30 |
| M.T1.729 | I | II-I-7 | II-F-31 |
| M.T1.730 | I | II-I-7 | II-F-32 |
| M.T1.731 | I | II-I-7 | II-F-33 |
| M.T1.732 | I | II-I-7 | II-F-34 |
| M.T1.733 | I | II-I-7 | II-I-22 |
| M.T1.734 | I | II-I-8 | II-F-1 |
| M.T1.735 | I | II-I-8 | II-F-2 |
| M.T1.736 | I | II-I-8 | II-F-3 |
| M.T1.737 | I | II-I-8 | II-F-4 |
| M.T1.738 | I | II-I-8 | II-F-5 |
| M.T1.739 | I | II-I-8 | II-F-6 |
| M.T1.740 | I | II-I-8 | II-F-7 |
| M.T1.741 | I | II-I-8 | II-F-8 |
| M.T1.742 | I | II-I-8 | II-F-9 |
| M.T1.743 | I | II-I-8 | II-F-10 |
| M.T1.744 | I | II-I-8 | II-F-11 |
| M.T1.745 | I | II-I-8 | II-F-12 |
| M.T1.746 | I | II-I-8 | II-F-13 |
| M.T1.747 | I | II-I-8 | II-F-14 |
| M.T1.748 | I | II-I-8 | II-F-15 |
| M.T1.749 | I | II-I-8 | II-F-16 |
| M.T1.750 | I | II-I-8 | II-F-17 |
| M.T1.751 | I | II-I-8 | II-F-18 |
| M.T1.752 | I | II-I-8 | II-F-19 |
| M.T1.753 | I | II-I-8 | II-F-20 |
| M.T1.754 | I | II-I-8 | II-F-21 |
| M.T1.755 | I | II-I-8 | II-F-22 |
| M.T1.756 | I | II-I-8 | II-F-23 |
| M.T1.757 | I | II-I-8 | II-F-24 |
| M.T1.758 | I | II-I-8 | II-F-25 |
| M.T1.759 | I | II-I-8 | II-F-26 |
| M.T1.760 | I | II-I-8 | II-F-27 |
| M.T1.761 | I | II-I-8 | II-F-28 |
| M.T1.762 | I | II-I-8 | II-F-29 |
| M.T1.763 | I | II-I-8 | II-F-30 |
| M.T1.764 | I | II-I-8 | II-F-31 |

TABLE T-1-continued

| Mixture No. | Comp. I | Comp. II | Comp. III |
|---|---|---|---|
| M.T1.765 | I | II-I-8 | II-F-32 |
| M.T1.766 | I | II-I-8 | II-F-33 |
| M.T1.767 | I | II-I-8 | II-F-34 |
| M.T1.768 | I | II-I-8 | II-I-22 |
| M.T1.769 | I | II-I-9 | II-F-1 |
| M.T1.770 | I | II-I-9 | II-F-2 |
| M.T1.771 | I | II-I-9 | II-F-3 |
| M.T1.772 | I | II-I-9 | II-F-4 |
| M.T1.773 | I | II-I-9 | II-F-5 |
| M.T1.774 | I | II-I-9 | II-F-6 |
| M.T1.775 | I | II-I-9 | II-F-7 |
| M.T1.776 | I | II-I-9 | II-F-8 |
| M.T1.777 | I | II-I-9 | II-F-9 |
| M.T1.778 | I | II-I-9 | II-F-10 |
| M.T1.779 | I | II-I-9 | II-F-11 |
| M.T1.780 | I | II-I-9 | II-F-12 |
| M.T1.781 | I | II-I-9 | II-F-13 |
| M.T1.782 | I | II-I-9 | II-F-14 |
| M.T1.783 | I | II-I-9 | II-F-15 |
| M.T1.784 | I | II-I-9 | II-F-16 |
| M.T1.785 | I | II-I-9 | II-F-17 |
| M.T1.786 | I | II-I-9 | II-F-18 |
| M.T1.787 | I | II-I-9 | II-F-19 |
| M.T1.788 | I | II-I-9 | II-F-20 |
| M.T1.789 | I | II-I-9 | II-F-21 |
| M.T1.790 | I | II-I-9 | II-F-22 |
| M.T1.791 | I | II-I-9 | II-F-23 |
| M.T1.792 | I | II-I-9 | II-F-24 |
| M.T1.793 | I | II-I-9 | II-F-25 |
| M.T1.794 | I | II-I-9 | II-F-26 |
| M.T1.795 | I | II-I-9 | II-F-27 |
| M.T1.796 | I | II-I-9 | II-F-28 |
| M.T1.797 | I | II-I-9 | II-F-29 |
| M.T1.798 | I | II-I-9 | II-F-30 |
| M.T1.799 | I | II-I-9 | II-F-31 |
| M.T1.800 | I | II-I-9 | II-F-32 |
| M.T1.801 | I | II-I-9 | II-F-33 |
| M.T1.802 | I | II-I-9 | II-F-34 |
| M.T1.803 | I | II-I-9 | II-I-22 |
| M.T1.804 | I | II-I-10 | II-F-1 |
| M.T1.805 | I | II-I-10 | II-F-2 |
| M.T1.806 | I | II-I-10 | II-F-3 |
| M.T1.807 | I | II-I-10 | II-F-4 |
| M.T1.808 | I | II-I-10 | II-F-5 |
| M.T1.809 | I | II-I-10 | II-F-6 |
| M.T1.810 | I | II-I-10 | II-F-7 |
| M.T1.811 | I | II-I-10 | II-F-8 |
| M.T1.812 | I | II-I-10 | II-F-9 |
| M.T1.813 | I | II-I-10 | II-F-10 |
| M.T1.814 | I | II-I-10 | II-F-11 |
| M.T1.815 | I | II-I-10 | II-F-12 |
| M.T1.816 | I | II-I-10 | II-F-13 |
| M.T1.817 | I | II-I-10 | II-F-14 |
| M.T1.818 | I | II-I-10 | II-F-15 |
| M.T1.819 | I | II-I-10 | II-F-16 |
| M.T1.820 | I | II-I-10 | II-F-17 |
| M.T1.821 | I | II-I-10 | II-F-18 |
| M.T1.822 | I | II-I-10 | II-F-19 |
| M.T1.823 | I | II-I-10 | II-F-20 |
| M.T1.824 | I | II-I-10 | II-F-21 |
| M.T1.825 | I | II-I-10 | II-F-22 |
| M.T1.826 | I | II-I-10 | II-F-23 |
| M.T1.827 | I | II-I-10 | II-F-24 |
| M.T1.828 | I | II-I-10 | II-F-25 |
| M.T1.829 | I | II-I-10 | II-F-26 |
| M.T1.830 | I | II-I-10 | II-F-27 |
| M.T1.831 | I | II-I-10 | II-F-28 |
| M.T1.832 | I | II-I-10 | II-F-29 |
| M.T1.833 | I | II-I-10 | II-F-30 |
| M.T1.834 | I | II-I-10 | II-F-31 |
| M.T1.835 | I | II-I-10 | II-F-32 |
| M.T1.836 | I | II-I-10 | II-F-33 |
| M.T1.837 | I | II-I-10 | II-F-34 |
| M.T1.838 | I | II-I-10 | II-I-22 |
| M.T1.839 | I | II-I-11 | II-F-1 |
| M.T1.840 | I | II-I-11 | II-F-2 |
| M.T1.841 | I | II-I-11 | II-F-3 |
| M.T1.842 | I | II-I-11 | II-F-4 |
| M.T1.843 | I | II-I-11 | II-F-5 |
| M.T1.844 | I | II-I-11 | II-F-6 |
| M.T1.845 | I | II-I-11 | II-F-7 |
| M.T1.846 | I | II-I-11 | II-F-8 |
| M.T1.847 | I | II-I-11 | II-F-9 |
| M.T1.848 | I | II-I-11 | II-F-10 |
| M.T1.849 | I | II-I-11 | II-F-11 |
| M.T1.850 | I | II-I-11 | II-F-12 |
| M.T1.851 | I | II-I-11 | II-F-13 |
| M.T1.852 | I | II-I-11 | II-F-14 |
| M.T1.853 | I | II-I-11 | II-F-15 |
| M.T1.854 | I | II-I-11 | II-F-16 |
| M.T1.855 | I | II-I-11 | II-F-17 |
| M.T1.856 | I | II-I-11 | II-F-18 |
| M.T1.857 | I | II-I-11 | II-F-19 |
| M.T1.858 | I | II-I-11 | II-F-20 |
| M.T1.859 | I | II-I-11 | II-F-21 |
| M.T1.860 | I | II-I-11 | II-F-22 |
| M.T1.861 | I | II-I-11 | II-F-23 |
| M.T1.862 | I | II-I-11 | II-F-24 |
| M.T1.863 | I | II-I-11 | II-F-25 |
| M.T1.864 | I | II-I-11 | II-F-26 |
| M.T1.865 | I | II-I-11 | II-F-27 |
| M.T1.866 | I | II-I-11 | II-F-28 |
| M.T1.867 | I | II-I-11 | II-F-29 |
| M.T1.868 | I | II-I-11 | II-F-30 |
| M.T1.869 | I | II-I-11 | II-F-31 |
| M.T1.870 | I | II-I-11 | II-F-32 |
| M.T1.871 | I | II-I-11 | II-F-33 |
| M.T1.872 | I | II-I-11 | II-F-34 |
| M.T1.873 | I | II-I-11 | II-I-22 |
| M.T1.874 | I | II-I-12 | II-F-1 |
| M.T1.875 | I | II-I-12 | II-F-2 |
| M.T1.876 | I | II-I-12 | II-F-3 |
| M.T1.877 | I | II-I-12 | II-F-4 |
| M.T1.878 | I | II-I-12 | II-F-5 |
| M.T1.879 | I | II-I-12 | II-F-6 |
| M.T1.880 | I | II-I-12 | II-F-7 |
| M.T1.881 | I | II-I-12 | II-F-8 |
| M.T1.882 | I | II-I-12 | II-F-9 |
| M.T1.883 | I | II-I-12 | II-F-10 |
| M.T1.884 | I | II-I-12 | II-F-11 |
| M.T1.885 | I | II-I-12 | II-F-12 |
| M.T1.886 | I | II-I-12 | II-F-13 |
| M.T1.887 | I | II-I-12 | II-F-14 |
| M.T1.888 | I | II-I-12 | II-F-15 |
| M.T1.889 | I | II-I-12 | II-F-16 |
| M.T1.890 | I | II-I-12 | II-F-17 |
| M.T1.891 | I | II-I-12 | II-F-18 |
| M.T1.892 | I | II-I-12 | II-F-19 |
| M.T1.893 | I | II-I-12 | II-F-20 |
| M.T1.894 | I | II-I-12 | II-F-21 |
| M.T1.895 | I | II-I-12 | II-F-22 |
| M.T1.896 | I | II-I-12 | II-F-23 |
| M.T1.897 | I | II-I-12 | II-F-24 |
| M.T1.898 | I | II-I-12 | II-F-25 |
| M.T1.899 | I | II-I-12 | II-F-26 |
| M.T1.900 | I | II-I-12 | II-F-27 |
| M.T1.901 | I | II-I-12 | II-F-28 |
| M.T1.902 | I | II-I-12 | II-F-29 |
| M.T1.903 | I | II-I-12 | II-F-30 |
| M.T1.904 | I | II-I-12 | II-F-31 |
| M.T1.905 | I | II-I-12 | II-F-32 |
| M.T1.906 | I | II-I-12 | II-F-33 |
| M.T1.907 | I | II-I-12 | II-F-34 |
| M.T1.908 | I | II-I-12 | II-I-22 |
| M.T1.909 | I | II-I-13 | II-F-1 |
| M.T1.910 | I | II-I-13 | II-F-2 |
| M.T1.911 | I | II-I-13 | II-F-3 |
| M.T1.912 | I | II-I-13 | II-F-4 |
| M.T1.913 | I | II-I-13 | II-F-5 |
| M.T1.914 | I | II-I-13 | II-F-6 |
| M.T1.915 | I | II-I-13 | II-F-7 |
| M.T1.916 | I | II-I-13 | II-F-8 |
| M.T1.917 | I | II-I-13 | II-F-9 |
| M.T1.918 | I | II-I-13 | II-F-10 |

TABLE T-1-continued

| Mixture No. | Comp. I | Comp. II | Comp. III |
|---|---|---|---|
| M.T1.919 | I | II-I-13 | II-F-11 |
| M.T1.920 | I | II-I-13 | II-F-12 |
| M.T1.921 | I | II-I-13 | II-F-13 |
| M.T1.922 | I | II-I-13 | II-F-14 |
| M.T1.923 | I | II-I-13 | II-F-15 |
| M.T1.924 | I | II-I-13 | II-F-16 |
| M.T1.925 | I | II-I-13 | II-F-17 |
| M.T1.926 | I | II-I-13 | II-F-18 |
| M.T1.927 | I | II-I-13 | II-F-19 |
| M.T1.928 | I | II-I-13 | II-F-20 |
| M.T1.929 | I | II-I-13 | II-F-21 |
| M.T1.930 | I | II-I-13 | II-F-22 |
| M.T1.931 | I | II-I-13 | II-F-23 |
| M.T1.932 | I | II-I-13 | II-F-24 |
| M.T1.933 | I | II-I-13 | II-F-25 |
| M.T1.934 | I | II-I-13 | II-F-26 |
| M.T1.935 | I | II-I-13 | II-F-27 |
| M.T1.936 | I | II-I-13 | II-F-28 |
| M.T1.937 | I | II-I-13 | II-F-29 |
| M.T1.938 | I | II-I-13 | II-F-30 |
| M.T1.939 | I | II-I-13 | II-F-31 |
| M.T1.940 | I | II-I-13 | II-F-32 |
| M.T1.941 | I | II-I-13 | II-F-33 |
| M.T1.942 | I | II-I-13 | II-F-34 |
| M.T1.943 | I | II-I-13 | II-I-22 |
| M.T1.944 | I | II-I-14 | II-F-1 |
| M.T1.945 | I | II-I-14 | II-F-2 |
| M.T1.946 | I | II-I-14 | II-F-3 |
| M.T1.947 | I | II-I-14 | II-F-4 |
| M.T1.948 | I | II-I-14 | II-F-5 |
| M.T1.949 | I | II-I-14 | II-F-6 |
| M.T1.950 | I | II-I-14 | II-F-7 |
| M.T1.951 | I | II-I-14 | II-F-8 |
| M.T1.952 | I | II-I-14 | II-F-9 |
| M.T1.953 | I | II-I-14 | II-F-10 |
| M.T1.954 | I | II-I-14 | II-F-11 |
| M.T1.955 | I | II-I-14 | II-F-12 |
| M.T1.956 | I | II-I-14 | II-F-13 |
| M.T1.957 | I | II-I-14 | II-F-14 |
| M.T1.958 | I | II-I-14 | II-F-15 |
| M.T1.959 | I | II-I-14 | II-F-16 |
| M.T1.960 | I | II-I-14 | II-F-17 |
| M.T1.961 | I | II-I-14 | II-F-18 |
| M.T1.962 | I | II-I-14 | II-F-19 |
| M.T1.963 | I | II-I-14 | II-F-20 |
| M.T1.964 | I | II-I-14 | II-F-21 |
| M.T1.965 | I | II-I-14 | II-F-22 |
| M.T1.966 | I | II-I-14 | II-F-23 |
| M.T1.967 | I | II-I-14 | II-F-24 |
| M.T1.968 | I | II-I-14 | II-F-25 |
| M.T1.969 | I | II-I-14 | II-F-26 |
| M.T1.970 | I | II-I-14 | II-F-27 |
| M.T1.971 | I | II-I-14 | II-F-28 |
| M.T1.972 | I | II-I-14 | II-F-29 |
| M.T1.973 | I | II-I-14 | II-F-30 |
| M.T1.974 | I | II-I-14 | II-F-31 |
| M.T1.975 | I | II-I-14 | II-F-32 |
| M.T1.976 | I | II-I-14 | II-F-33 |
| M.T1.977 | I | II-I-14 | II-F-34 |
| M.T1.978 | I | II-I-14 | II-I-22 |
| M.T1.979 | I | II-I-15 | II-F-1 |
| M.T1.980 | I | II-I-15 | II-F-2 |
| M.T1.981 | I | II-I-15 | II-F-3 |
| M.T1.982 | I | II-I-15 | II-F-4 |
| M.T1.983 | I | II-I-15 | II-F-5 |
| M.T1.984 | I | II-I-15 | II-F-6 |
| M.T1.985 | I | II-I-15 | II-F-7 |
| M.T1.986 | I | II-I-15 | II-F-8 |
| M.T1.987 | I | II-I-15 | II-F-9 |
| M.T1.988 | I | II-I-15 | II-F-10 |
| M.T1.989 | I | II-I-15 | II-F-11 |
| M.T1.990 | I | II-I-15 | II-F-12 |
| M.T1.991 | I | II-I-15 | II-F-13 |
| M.T1.992 | I | II-I-15 | II-F-14 |
| M.T1.993 | I | II-I-15 | II-F-15 |
| M.T1.994 | I | II-I-15 | II-F-16 |
| M.T1.995 | I | II-I-15 | II-F-17 |
| M.T1.996 | I | II-I-15 | II-F-18 |
| M.T1.997 | I | II-I-15 | II-F-19 |
| M.T1.998 | I | II-I-15 | II-F-20 |
| M.T1.999 | I | II-I-15 | II-F-21 |
| M.T1.1000 | I | II-I-15 | II-F-22 |
| M.T1.1001 | I | II-I-15 | II-F-23 |
| M.T1.1002 | I | II-I-15 | II-F-24 |
| M.T1.1003 | I | II-I-15 | II-F-25 |
| M.T1.1004 | I | II-I-15 | II-F-26 |
| M.T1.1005 | I | II-I-15 | II-F-27 |
| M.T1.1006 | I | II-I-15 | II-F-28 |
| M.T1.1007 | I | II-I-15 | II-F-29 |
| M.T1.1008 | I | II-I-15 | II-F-30 |
| M.T1.1009 | I | II-I-15 | II-F-31 |
| M.T1.1010 | I | II-I-15 | II-F-32 |
| M.T1.1011 | I | II-I-15 | II-F-33 |
| M.T1.1012 | I | II-I-15 | II-F-34 |
| M.T1.1013 | I | II-I-15 | II-I-22 |
| M.T1.1014 | I | II-I-16 | II-F-1 |
| M.T1.1015 | I | II-I-16 | II-F-2 |
| M.T1.1016 | I | II-I-16 | II-F-3 |
| M.T1.1017 | I | II-I-16 | II-F-4 |
| M.T1.1018 | I | II-I-16 | II-F-5 |
| M.T1.1019 | I | II-I-16 | II-F-6 |
| M.T1.1020 | I | II-I-16 | II-F-7 |
| M.T1.1021 | I | II-I-16 | II-F-8 |
| M.T1.1022 | I | II-I-16 | II-F-9 |
| M.T1.1023 | I | II-I-16 | II-F-10 |
| M.T1.1024 | I | II-I-16 | II-F-11 |
| M.T1.1025 | I | II-I-16 | II-F-12 |
| M.T1.1026 | I | II-I-16 | II-F-13 |
| M.T1.1027 | I | II-I-16 | II-F-14 |
| M.T1.1028 | I | II-I-16 | II-F-15 |
| M.T1.1029 | I | II-I-16 | II-F-16 |
| M.T1.1030 | I | II-I-16 | II-F-17 |
| M.T1.1031 | I | II-I-16 | II-F-18 |
| M.T1.1032 | I | II-I-16 | II-F-19 |
| M.T1.1033 | I | II-I-16 | II-F-20 |
| M.T1.1034 | I | II-I-16 | II-F-21 |
| M.T1.1035 | I | II-I-16 | II-F-22 |
| M.T1.1036 | I | II-I-16 | II-F-23 |
| M.T1.1037 | I | II-I-16 | II-F-24 |
| M.T1.1038 | I | II-I-16 | II-F-25 |
| M.T1.1039 | I | II-I-16 | II-F-26 |
| M.T1.1040 | I | II-I-16 | II-F-27 |
| M.T1.1041 | I | II-I-16 | II-F-28 |
| M.T1.1042 | I | II-I-16 | II-F-29 |
| M.T1.1043 | I | II-I-16 | II-F-30 |
| M.T1.1044 | I | II-I-16 | II-F-31 |
| M.T1.1045 | I | II-I-16 | II-F-32 |
| M.T1.1046 | I | II-I-16 | II-F-33 |
| M.T1.1047 | I | II-I-16 | II-F-34 |
| M.T1.1048 | I | II-I-16 | II-I-22 |
| M.T1.1049 | I | II-I-17 | II-F-1 |
| M.T1.1050 | I | II-I-17 | II-F-2 |
| M.T1.1051 | I | II-I-17 | II-F-3 |
| M.T1.1052 | I | II-I-17 | II-F-4 |
| M.T1.1053 | I | II-I-17 | II-F-5 |
| M.T1.1054 | I | II-I-17 | II-F-6 |
| M.T1.1055 | I | II-I-17 | II-F-7 |
| M.T1.1056 | I | II-I-17 | II-F-8 |
| M.T1.1057 | I | II-I-17 | II-F-9 |
| M.T1.1058 | I | II-I-17 | II-F-10 |
| M.T1.1059 | I | II-I-17 | II-F-11 |
| M.T1.1060 | I | II-I-17 | II-F-12 |
| M.T1.1061 | I | II-I-17 | II-F-13 |
| M.T1.1062 | I | II-I-17 | II-F-14 |
| M.T1.1063 | I | II-I-17 | II-F-15 |
| M.T1.1064 | I | II-I-17 | II-F-16 |
| M.T1.1065 | I | II-I-17 | II-F-17 |
| M.T1.1066 | I | II-I-17 | II-F-18 |
| M.T1.1067 | I | II-I-17 | II-F-19 |
| M.T1.1068 | I | II-I-17 | II-F-20 |
| M.T1.1069 | I | II-I-17 | II-F-21 |
| M.T1.1070 | I | II-I-17 | II-F-22 |
| M.T1.1071 | I | II-I-17 | II-F-23 |
| M.T1.1072 | I | II-I-17 | II-F-24 |

TABLE T-1-continued

| Mixture No. | Comp. I | Comp. II | Comp. III |
|---|---|---|---|
| M.T1.1073 | I | II-I-17 | II-F-25 |
| M.T1.1074 | I | II-I-17 | II-F-26 |
| M.T1.1075 | I | II-I-17 | II-F-27 |
| M.T1.1076 | I | II-I-17 | II-F-28 |
| M.T1.1077 | I | II-I-17 | II-F-29 |
| M.T1.1078 | I | II-I-17 | II-F-30 |
| M.T1.1079 | I | II-I-17 | II-F-31 |
| M.T1.1080 | I | II-I-17 | II-F-32 |
| M.T1.1081 | I | II-I-17 | II-F-33 |
| M.T1.1082 | I | II-I-17 | II-F-34 |
| M.T1.1083 | I | II-I-17 | II-I-22 |
| M.T1.1084 | I | II-I-18 | II-F-1 |
| M.T1.1085 | I | II-I-18 | II-F-2 |
| M.T1.1086 | I | II-I-18 | II-F-3 |
| M.T1.1087 | I | II-I-18 | II-F-4 |
| M.T1.1088 | I | II-I-18 | II-F-5 |
| M.T1.1089 | I | II-I-18 | II-F-6 |
| M.T1.1090 | I | II-I-18 | II-F-7 |
| M.T1.1091 | I | II-I-18 | II-F-8 |
| M.T1.1092 | I | II-I-18 | II-F-9 |
| M.T1.1093 | I | II-I-18 | II-F-10 |
| M.T1.1094 | I | II-I-18 | II-F-11 |
| M.T1.1095 | I | II-I-18 | II-F-12 |
| M.T1.1096 | I | II-I-18 | II-F-13 |
| M.T1.1097 | I | II-I-18 | II-F-14 |
| M.T1.1098 | I | II-I-18 | II-F-15 |
| M.T1.1099 | I | II-I-18 | II-F-16 |
| M.T1.1100 | I | II-I-18 | II-F-17 |
| M.T1.1101 | I | II-I-18 | II-F-18 |
| M.T1.1102 | I | II-I-18 | II-F-19 |
| M.T1.1103 | I | II-I-18 | II-F-20 |
| M.T1.1104 | I | II-I-18 | II-F-21 |
| M.T1.1105 | I | II-I-18 | II-F-22 |
| M.T1.1106 | I | II-I-18 | II-F-23 |
| M.T1.1107 | I | II-I-18 | II-F-24 |
| M.T1.1108 | I | II-I-18 | II-F-25 |
| M.T1.1109 | I | II-I-18 | II-F-26 |
| M.T1.1110 | I | II-I-18 | II-F-27 |
| M.T1.1111 | I | II-I-18 | II-F-28 |
| M.T1.1112 | I | II-I-18 | II-F-29 |
| M.T1.1113 | I | II-I-18 | II-F-30 |
| M.T1.1114 | I | II-I-18 | II-F-31 |
| M.T1.1115 | I | II-I-18 | II-F-32 |
| M.T1.1116 | I | II-I-18 | II-F-33 |
| M.T1.1117 | I | II-I-18 | II-F-34 |
| M.T1.1118 | I | II-I-18 | II-I-22 |
| M.T1.1119 | I | II-I-19 | II-F-1 |
| M.T1.1120 | I | II-I-19 | II-F-2 |
| M.T1.1121 | I | II-I-19 | II-F-3 |
| M.T1.1122 | I | II-I-19 | II-F-4 |
| M.T1.1123 | I | II-I-19 | II-F-5 |
| M.T1.1124 | I | II-I-19 | II-F-6 |
| M.T1.1125 | I | II-I-19 | II-F-7 |
| M.T1.1126 | I | II-I-19 | II-F-8 |
| M.T1.1127 | I | II-I-19 | II-F-9 |
| M.T1.1128 | I | II-I-19 | II-F-10 |
| M.T1.1129 | I | II-I-19 | II-F-11 |
| M.T1.1130 | I | II-I-19 | II-F-12 |
| M.T1.1131 | I | II-I-19 | II-F-13 |
| M.T1.1132 | I | II-I-19 | II-F-14 |
| M.T1.1133 | I | II-I-19 | II-F-15 |
| M.T1.1134 | I | II-I-19 | II-F-16 |
| M.T1.1135 | I | II-I-19 | II-F-17 |
| M.T1.1136 | I | II-I-19 | II-F-18 |
| M.T1.1137 | I | II-I-19 | II-F-19 |
| M.T1.1138 | I | II-I-19 | II-F-20 |
| M.T1.1139 | I | II-I-19 | II-F-21 |
| M.T1.1140 | I | II-I-19 | II-F-22 |
| M.T1.1141 | I | II-I-19 | II-F-23 |
| M.T1.1142 | I | II-I-19 | II-F-24 |
| M.T1.1143 | I | II-I-19 | II-F-25 |
| M.T1.1144 | I | II-I-19 | II-F-26 |
| M.T1.1145 | I | II-I-19 | II-F-27 |
| M.T1.1146 | I | II-I-19 | II-F-28 |
| M.T1.1147 | I | II-I-19 | II-F-29 |
| M.T1.1148 | I | II-I-19 | II-F-30 |
| M.T1.1149 | I | II-I-19 | II-F-31 |
| M.T1.1150 | I | II-I-19 | II-F-32 |
| M.T1.1151 | I | II-I-19 | II-F-33 |
| M.T1.1152 | I | II-I-19 | II-F-34 |
| M.T1.1153 | I | II-I-19 | II-I-22 |
| M.T1.1154 | I | II-I-20 | II-F-1 |
| M.T1.1155 | I | II-I-20 | II-F-2 |
| M.T1.1156 | I | II-I-20 | II-F-3 |
| M.T1.1157 | I | II-I-20 | II-F-4 |
| M.T1.1158 | I | II-I-20 | II-F-5 |
| M.T1.1159 | I | II-I-20 | II-F-6 |
| M.T1.1160 | I | II-I-20 | II-F-7 |
| M.T1.1161 | I | II-I-20 | II-F-8 |
| M.T1.1162 | I | II-I-20 | II-F-9 |
| M.T1.1163 | I | II-I-20 | II-F-10 |
| M.T1.1164 | I | II-I-20 | II-F-11 |
| M.T1.1165 | I | II-I-20 | II-F-12 |
| M.T1.1166 | I | II-I-20 | II-F-13 |
| M.T1.1167 | I | II-I-20 | II-F-14 |
| M.T1.1168 | I | II-I-20 | II-F-15 |
| M.T1.1169 | I | II-I-20 | II-F-16 |
| M.T1.1170 | I | II-I-20 | II-F-17 |
| M.T1.1171 | I | II-I-20 | II-F-18 |
| M.T1.1172 | I | II-I-20 | II-F-19 |
| M.T1.1173 | I | II-I-20 | II-F-20 |
| M.T1.1174 | I | II-I-20 | II-F-21 |
| M.T1.1175 | I | II-I-20 | II-F-22 |
| M.T1.1176 | I | II-I-20 | II-F-23 |
| M.T1.1177 | I | II-I-20 | II-F-24 |
| M.T1.1178 | I | II-I-20 | II-F-25 |
| M.T1.1179 | I | II-I-20 | II-F-26 |
| M.T1.1180 | I | II-I-20 | II-F-27 |
| M.T1.1181 | I | II-I-20 | II-F-28 |
| M.T1.1182 | I | II-I-20 | II-F-29 |
| M.T1.1183 | I | II-I-20 | II-F-30 |
| M.T1.1184 | I | II-I-20 | II-F-31 |
| M.T1.1185 | I | II-I-20 | II-F-32 |
| M.T1.1186 | I | II-I-20 | II-F-33 |
| M.T1.1187 | I | II-I-20 | II-F-34 |
| M.T1.1188 | I | II-I-20 | II-I-22 |
| M.T1.1189 | I | II-I-21 | II-F-1 |
| M.T1.1190 | I | II-I-21 | II-F-2 |
| M.T1.1191 | I | II-I-21 | II-F-3 |
| M.T1.1192 | I | II-I-21 | II-F-4 |
| M.T1.1193 | I | II-I-21 | II-F-5 |
| M.T1.1194 | I | II-I-21 | II-F-6 |
| M.T1.1195 | I | II-I-21 | II-F-7 |
| M.T1.1196 | I | II-I-21 | II-F-8 |
| M.T1.1197 | I | II-I-21 | II-F-9 |
| M.T1.1198 | I | II-I-21 | II-F-10 |
| M.T1.1199 | I | II-I-21 | II-F-11 |
| M.T1.1200 | I | II-I-21 | II-F-12 |
| M.T1.1201 | I | II-I-21 | II-F-13 |
| M.T1.1202 | I | II-I-21 | II-F-14 |
| M.T1.1203 | I | II-I-21 | II-F-15 |
| M.T1.1204 | I | II-I-21 | II-F-16 |
| M.T1.1205 | I | II-I-21 | II-F-17 |
| M.T1.1206 | I | II-I-21 | II-F-18 |
| M.T1.1207 | I | II-I-21 | II-F-19 |
| M.T1.1208 | I | II-I-21 | II-F-20 |
| M.T1.1209 | I | II-I-21 | II-F-21 |
| M.T1.1210 | I | II-I-21 | II-F-22 |
| M.T1.1211 | I | II-I-21 | II-F-23 |
| M.T1.1212 | I | II-I-21 | II-F-24 |
| M.T1.1213 | I | II-I-21 | II-F-25 |
| M.T1.1214 | I | II-I-21 | II-F-26 |
| M.T1.1215 | I | II-I-21 | II-F-27 |
| M.T1.1216 | I | II-I-21 | II-F-28 |
| M.T1.1217 | I | II-I-21 | II-F-29 |
| M.T1.1218 | I | II-I-21 | II-F-30 |
| M.T1.1219 | I | II-I-21 | II-F-31 |
| M.T1.1220 | I | II-I-21 | II-F-32 |
| M.T1.1221 | I | II-I-21 | II-F-33 |
| M.T1.1222 | I | II-I-21 | II-F-34 |
| M.T1.1223 | I | II-I-21 | II-I-22 |
| M.T1.1224 | I | II-I-1 | II-I-2 |
| M.T1.1225 | I | II-I-1 | II-I-3 |
| M.T1.1226 | I | II-I-1 | II-I-4 |

TABLE T-1-continued

| Mixture No. | Comp. I | Comp. II | Comp. III |
|---|---|---|---|
| M.T1.1227 | I | II-I-1 | II-I-5 |
| M.T1.1228 | I | II-I-1 | II-I-6 |
| M.T1.1229 | I | II-I-1 | II-I-7 |
| M.T1.1230 | I | II-I-1 | II-I-8 |
| M.T1.1231 | I | II-I-1 | II-I-9 |
| M.T1.1232 | I | II-I-1 | II-I-10 |
| M.T1.1233 | I | II-I-1 | II-I-11 |
| M.T1.1234 | I | II-I-1 | II-I-12 |
| M.T1.1235 | I | II-I-1 | II-I-13 |
| M.T1.1236 | I | II-I-1 | II-I-14 |
| M.T1.1237 | I | II-I-1 | II-I-15 |
| M.T1.1238 | I | II-I-1 | II-I-16 |
| M.T1.1239 | I | II-I-1 | II-I-17 |
| M.T1.1240 | I | II-I-1 | II-I-18 |
| M.T1.1241 | I | II-I-1 | II-I-19 |
| M.T1.1242 | I | II-I-1 | II-I-20 |
| M.T1.1243 | I | II-I-1 | II-I-21 |
| M.T1.1244 | I | II-I-12 | II-I-2 |
| M.T1.1245 | I | II-I-12 | II-I-3 |
| M.T1.1246 | I | II-I-12 | II-I-4 |
| M.T1.1247 | I | II-I-12 | II-I-5 |
| M.T1.1248 | I | II-I-12 | II-I-6 |
| M.T1.1249 | I | II-I-12 | II-I-7 |
| M.T1.1250 | I | II-I-12 | II-I-8 |
| M.T1.1251 | I | II-I-12 | II-I-9 |
| M.T1.1252 | I | II-I-12 | II-I-10 |
| M.T1.1253 | I | II-I-12 | II-I-14 |
| M.T1.1254 | I | II-I-12 | II-I-15 |
| M.T1.1255 | I | II-I-12 | II-I-16 |
| M.T1.1256 | I | II-I-12 | II-I-17 |
| M.T1.1257 | I | II-I-12 | II-I-18 |
| M.T1.1258 | I | II-I-12 | II-I-19 |
| M.T1.1259 | I | II-I-12 | II-I-20 |
| M.T1.1260 | I | II-I-12 | II-I-21 |
| M.T1.1261 | I | II-I-12 | II-I-2 |
| M.T1.1262 | I | II-I-12 | II-I-3 |
| M.T1.1263 | I | II-I-12 | II-I-4 |
| M.T1.1264 | I | II-I-12 | II-I-5 |
| M.T1.1265 | I | II-I-12 | II-I-6 |
| M.T1.1266 | I | II-I-12 | II-I-7 |
| M.T1.1267 | I | II-I-12 | II-I-8 |
| M.T1.1268 | I | II-I-12 | II-I-9 |
| M.T1.1269 | I | II-I-12 | II-I-10 |
| M.T1.1270 | I | II-I-12 | II-I-14 |
| M.T1.1271 | I | II-I-12 | II-I-15 |
| M.T1.1272 | I | II-I-12 | II-I-16 |
| M.T1.1273 | I | II-I-12 | II-I-17 |
| M.T1.1274 | I | II-I-12 | II-I-18 |
| M.T1.1275 | I | II-I-12 | II-I-19 |
| M.T1.1276 | I | II-I-12 | II-I-20 |
| M.T1.1277 | I | II-I-12 | II-I-21 |
| M.T1.1278 | I | II-I-13 | II-I-2 |
| M.T1.1279 | I | II-I-13 | II-I-3 |
| M.T1.1280 | I | II-I-13 | II-I-4 |
| M.T1.1281 | I | II-I-13 | II-I-5 |
| M.T1.1282 | I | II-I-13 | II-I-6 |
| M.T1.1283 | I | II-I-13 | II-I-7 |
| M.T1.1284 | I | II-I-13 | II-I-8 |
| M.T1.1285 | I | II-I-13 | II-I-9 |
| M.T1.1286 | I | II-I-13 | II-I-10 |
| M.T1.1287 | I | II-I-13 | II-I-14 |
| M.T1.1288 | I | II-I-13 | II-I-15 |
| M.T1.1289 | I | II-I-13 | II-I-16 |
| M.T1.1290 | I | II-I-13 | II-I-17 |
| M.T1.1291 | I | II-I-13 | II-I-18 |
| M.T1.1292 | I | II-I-13 | II-I-19 |
| M.T1.1293 | I | II-I-13 | II-I-20 |
| M.T1.1294 | I | II-I-13 | II-I-21 |
| M.T1.1295 | I | II-I-2 | II-I-8 |
| M.T1.1296 | I | II-I-2 | II-I-9 |
| M.T1.1297 | I | II-I-2 | II-I-10 |
| M.T1.1298 | I | II-I-2 | II-I-14 |
| M.T1.1299 | I | II-I-2 | II-I-15 |
| M.T1.1300 | I | II-I-2 | II-I-16 |
| M.T1.1301 | I | II-I-2 | II-I-17 |
| M.T1.1302 | I | II-I-2 | II-I-19 |
| M.T1.1303 | I | II-I-2 | II-I-20 |
| M.T1.1304 | I | II-I-2 | II-I-8 |
| M.T1.1305 | I | II-I-2 | II-I-9 |
| M.T1.1306 | I | II-I-2 | II-I-10 |
| M.T1.1307 | I | II-I-2 | II-I-14 |
| M.T1.1308 | I | II-I-2 | II-I-15 |
| M.T1.1309 | I | II-I-2 | II-I-16 |
| M.T1.1310 | I | II-I-2 | II-I-17 |
| M.T1.1311 | I | II-I-2 | II-I-19 |
| M.T1.1312 | I | II-I-2 | II-I-20 |
| M.T1.1313 | I | II-I-3 | II-I-8 |
| M.T1.1314 | I | II-I-3 | II-I-9 |
| M.T1.1315 | I | II-I-3 | II-I-10 |
| M.T1.1316 | I | II-I-3 | II-I-14 |
| M.T1.1317 | I | II-I-3 | II-I-15 |
| M.T1.1318 | I | II-I-3 | II-I-16 |
| M.T1.1319 | I | II-I-3 | II-I-17 |
| M.T1.1320 | I | II-I-3 | II-I-19 |
| M.T1.1321 | I | II-I-3 | II-I-20 |
| M.T1.1322 | I | II-I-4 | II-I-8 |
| M.T1.1323 | I | II-I-4 | II-I-9 |
| M.T1.1324 | I | II-I-4 | II-I-10 |
| M.T1.1325 | I | II-I-4 | II-I-14 |
| M.T1.1326 | I | II-I-4 | II-I-15 |
| M.T1.1327 | I | II-I-4 | II-I-16 |
| M.T1.1328 | I | II-I-4 | II-I-17 |
| M.T1.1329 | I | II-I-4 | II-I-19 |
| M.T1.1330 | I | II-I-4 | II-I-20 |
| M.T1.1331 | I | II-I-5 | II-I-8 |
| M.T1.1332 | I | II-I-5 | II-I-9 |
| M.T1.1333 | I | II-I-5 | II-I-10 |
| M.T1.1334 | I | II-I-5 | II-I-14 |
| M.T1.1335 | I | II-I-5 | II-I-15 |
| M.T1.1336 | I | II-I-5 | II-I-16 |
| M.T1.1337 | I | II-I-5 | II-I-17 |
| M.T1.1338 | I | II-I-5 | II-I-19 |
| M.T1.1339 | I | II-I-5 | II-I-20 |
| M.T1.1340 | I | II-I-5 | II-I-8 |
| M.T1.1341 | I | II-I-5 | II-I-9 |
| M.T1.1342 | I | II-I-5 | II-I-10 |
| M.T1.1343 | I | II-I-5 | II-I-14 |
| M.T1.1344 | I | II-I-5 | II-I-15 |
| M.T1.1345 | I | II-I-5 | II-I-16 |
| M.T1.1346 | I | II-I-5 | II-I-17 |
| M.T1.1347 | I | II-I-5 | II-I-19 |
| M.T1.1348 | I | II-I-5 | II-I-20 |
| M.T1.1349 | I | II-I-6 | II-I-8 |
| M.T1.1350 | I | II-I-6 | II-I-9 |
| M.T1.1351 | I | II-I-6 | II-I-10 |
| M.T1.1352 | I | II-I-6 | II-I-14 |
| M.T1.1353 | I | II-I-6 | II-I-15 |
| M.T1.1354 | I | II-I-6 | II-I-16 |
| M.T1.1355 | I | II-I-6 | II-I-17 |
| M.T1.1356 | I | II-I-6 | II-I-19 |
| M.T1.1357 | I | II-I-6 | II-I-20 |
| M.T1.1358 | I | II-I-7 | II-I-8 |
| M.T1.1359 | I | II-I-7 | II-I-9 |
| M.T1.1360 | I | II-I-7 | II-I-10 |
| M.T1.1361 | I | II-I-7 | II-I-14 |
| M.T1.1362 | I | II-I-7 | II-I-15 |
| M.T1.1363 | I | II-I-7 | II-I-16 |
| M.T1.1364 | I | II-I-7 | II-I-17 |
| M.T1.1365 | I | II-I-7 | II-I-19 |
| M.T1.1366 | I | II-I-7 | II-I-20 |
| M.T1.1367 | I | II-I-21 | II-I-8 |
| M.T1.1368 | I | II-I-21 | II-I-9 |
| M.T1.1369 | I | II-I-21 | II-I-10 |
| M.T1.1370 | I | II-I-21 | II-I-14 |
| M.T1.1371 | I | II-I-21 | II-I-15 |
| M.T1.1372 | I | II-I-21 | II-I-16 |
| M.T1.1373 | I | II-I-21 | II-I-17 |
| M.T1.1374 | I | II-I-21 | II-I-19 |
| M.T1.1375 | I | II-I-21 | II-I-20 |
| M.T1.1376 | I | II-I-18 | II-I-8 |
| M.T1.1377 | I | II-I-18 | II-I-9 |
| M.T1.1378 | I | II-I-18 | II-I-10 |
| M.T1.1379 | I | II-I-18 | II-I-14 |
| M.T1.1380 | I | II-I-18 | II-I-15 |

TABLE T-1-continued

| Mixture No. | Comp. I | Comp. II | Comp. III |
|---|---|---|---|
| M.T1.1381 | I | II-I-18 | II-I-16 |
| M.T1.1382 | I | II-I-18 | II-I-17 |
| M.T1.1383 | I | II-I-18 | II-I-19 |
| M.T1.1384 | I | II-I-18 | II-I-20 |
| M.T1.1385 | I | II-I-16 | II-I-8 |
| M.T1.1386 | I | II-I-16 | II-I-9 |
| M.T1.1387 | I | II-I-16 | II-I-10 |
| M.T1.1388 | I | II-I-16 | II-I-14 |
| M.T1.1389 | I | II-I-16 | II-I-15 |
| M.T1.1390 | I | II-I-16 | II-I-17 |
| M.T1.1391 | I | II-I-16 | II-I-19 |
| M.T1.1392 | I | II-I-16 | II-I-20 |
| M.T1.1393 | I | II-I-15 | II-I-8 |
| M.T1.1394 | I | II-I-15 | II-I-9 |
| M.T1.1395 | I | II-I-15 | II-I-10 |
| M.T1.1396 | I | II-I-15 | II-I-14 |
| M.T1.1397 | I | II-I-15 | II-I-17 |
| M.T1.1398 | I | II-I-15 | II-I-19 |
| M.T1.1399 | I | II-I-15 | II-I-20 |
| M.T1.1400 | I | II-I-8 | II-I-9 |
| M.T1.1401 | I | II-I-8 | II-I-10 |
| M.T1.1402 | I | II-I-8 | II-I-14 |
| M.T1.1403 | I | II-I-8 | II-I-20 |
| M.T1.1404 | I | II-I-19 | II-I-9 |
| M.T1.1405 | I | II-I-19 | II-I-10 |
| M.T1.1406 | I | II-I-19 | II-I-14 |
| M.T1.1407 | I | II-I-19 | II-I-20 |
| M.T1.1408 | I | II-I-17 | II-I-9 |
| M.T1.1409 | I | II-I-17 | II-I-10 |
| M.T1.1410 | I | II-I-17 | II-I-14 |
| M.T1.1411 | I | II-I-17 | II-I-20 |
| M.T1.1412 | I | II-I-10 | II-I-9 |
| M.T1.1413 | I | II-I-10 | II-I-14 |
| M.T1.1414 | I | II-I-10 | II-I-20 |

As mentioned above, the mixtures according to the present invention may comprise the compound of formula (I) combined with one, two, three or four other active ingredients. Thus, mixtures as disclosed in table T-1 above, may additionally comprise further one or two active ingredients, selected from fungicides or insecticides.

According to one embodiment, the components of the composition according to the invention, such as parts of a kit or parts of a binary or ternary mixture, may be mixed by the user himself in a spray tank and further auxiliaries may be added, if appropriate.

In a further embodiment, either individual components of the composition according to the invention or partially premixed components, e.g. components comprising compounds I and/or active substances from the groups M.1 to M.Y or F.I) to F.XII) listed above, may be mixed by the user in a spray tank and further auxiliaries and additives may be added, if appropriate.

In a further embodiment, either individual components of the composition according to the invention or partially premixed components, e.g. components comprising compounds I and/or active substances from the groups M.1 to M.Y or F.I) to F.XII) listed above, can be applied jointly (e.g. after tank mix) or consecutively.

BIOLOGICAL EXAMPLES

Biological Tests

The applicability of compounds of formula (I) alone or in combination with other active ingredients in application methods according to the present invention may be evaluated in test examples as provided herein below or in similar assays. These test examples are not to be construed in any way as limiting.

As mentioned above, mixtures of compound of formula (I) with other agriculturally active ingredients may show surprisingly synergistic effects, which can also be demonstrated in the biological test systems described below.

Synergism can be described as an interaction where the combined effect of two or more compounds is greater than the sum of the individual effects of each of the compounds. The presence of a synergistic effect in terms of percent control, between two mixing partners (X and Y) can be calculated using the Colby equation (Colby, S. R., 1967, Calculating Synergistic and Antagonistic Responses in Herbicide Combinations, *Weeds*, 15, 20-22):

$$E = X + Y - \frac{XY}{100}$$

When the observed combined control effect is greater than the expected combined control effect (E), then the combined effect is synergistic.

The analysis of synergism or antagonism between the mixtures or compositions was determined using Colby's equation.

B.1 Control of Animal Pests

With regard to the control of animal pests affecting plant propagation material, especially seeds, the following test systems and results demonstrate the pesticidal activity of the carboxamide compound of formula I alone and its synergistic pesticidal activity in combination with other insecticidal active ingredients.

Test B.1.1 Control of Wireworm (*Melanotus communis*)

For evaluating control of wireworm (*Melanotus communis*) through direct contact method, the individual insects were dipped directly into compound solution.

The compounds or mixtures were dissolved in acetone at different concentrations. The compounds or mixtures were formulated using a solution containing 50% (v/v) acetone in water with 0.02 wt % Kinetic®.

For the experimental mixtures, identical volumes of both mixing partners were mixed together to achieve the desired respective concentrations. Wireworms were dipped directly into solution for three seconds and then allowed to air dry on filter paper.

About 11 $cm^3$ of water-moistened loamy sand was dispensed into each 16-$cm^2$ cell of a 32-cell rearing tray. One treated wireworm larva was infested into each cell along with two germinating wheat seeds. Cells were then covered with adhesive bio-assay tray lids. Each cell was a replicate and replication was 10×. After infestation, the test was maintained in an incubator at 26±1° C. in the dark. Mortality (dead+moribund insects) was evaluated 3 days after treatment (DAT) and mean percent mortality was calculated relative to the untreated control. The results are listed in table B.1.1.

TABLE B.1.1

| *Melanotus communis* | concentration [ppm] | Average Control % |
|---|---|---|
| Test B.1.1a): | | |
| Carboxamide compound of formula I | 3 | 33 |
| Cyantraniliprole | 225 | 22 |

TABLE B.1.1-continued

| Melanotus communis | concentration [ppm] | Average Control % |
|---|---|---|
| Cyantraniliprole + Carboxamide compound of formula I | 225 + 3 | 78* |
| Test B.1.1.b) | | |
| Carboxamide compound of formula I | 3 | 33 |
| Emamectin | 800 | 11 |
| Emamectin + Carboxamide compound of formula I | 800 + 3 | 44* |
| Test B.1.1.c) | | |
| Carboxamide compound of formula I | 3 | 33 |
| Fipronil | 30 | 22 |
| Fipronil + Carboxamide compound of formula I | 30 + 3 | 89* |
| Test B.1.1.d) | | |
| Carboxamide compound of formula I | 3 | 33 |
| Thiamethoxam | 25 | 11 |
| Thiamethoxam + Carboxamide compound of formula I | 25 + 3 | 44* |

*synergistic control effect according to Colby's equation

Test B.1.2 Control of Western Corn Rootworm (*Diabrotica virgifera virgifera*)

For evaluating control of western corn rootworm (*Diabrotica virgifera virgifera*) through maximum exposure method, the insects were exposed to treated soil.

The compounds or mixtures were first dissolved in acetone, and then mixed with soil to obtain the desired different ppm concentrations (w/w) of compound/soil or mixture/soil. For experimental mixtures, identical volumes of both mixing partners were mixed together to achieve the desired respective concentrations. Treatments were applied in solution to sifted (#10 sieve) loamy sand in a plastic bag. Treatments were thoroughly incorporated by sealing and shaking each bag by hand and allowing the solution to soak through the soil mass for at least 10 minutes. Bags were then unsealed and kept open in a fume hood overnight to evaporate the solvent from the soil.

One day after treatment (DAT) water for moisture and water-soaked millet seed as a food source were added to each bag and incorporated thoroughly. About 11 cm³ of the millet and soil mixture was dispensed into a 1-oz. plastic cup. Each cup was infested with 10 western corn rootworm second-instar larvae and covered. Each cup was a replicate and replication was 3x. The test was maintained in an incubator at 26±1° C. in the dark. Mortality (dead+moribund insects) was evaluated 3 days after infestation (DAI) and mean percent mortality was calculated relative to the untreated control. The results are listed in table B.1.2.

TABLE B.1,2

| Diabrotica virgifera virgifera | concentration [ppm compound or mixture/soil] | Average Control % |
|---|---|---|
| Test B.1.2.a) | | |
| Carboxamide compound of formula I | 0.01 | 30 |
| Clothianidin | 0.1 | 33 |
| Clothianidin + Carboxamide compound of formula I | 0.1 + 0.01 | 70* |
| Test B.1.2.b) | | |
| Carboxamide compound of formula I | 0.01 | 30 |
| Cyantraniliprole | 3.1 | 23 |
| Cyantraniliprole + Carboxamide compound of formula I | 3.1 + 0.01 | 50* |
| Test B.1.2.c) | | |
| Carboxamide compound of formula I | 0.01 | 30 |
| Fipronil | 0.03 | 27 |
| Fipronil + Carboxamide compound of formula I | 0.03 + 0.01 | 63* |
| Test B.1.2.d) | | |
| Carboxamide compound of formula I | 0.01 | 30 |
| Imidacloprid | 0.13 | 17 |
| Imidacloprid + Carboxamide compound of formula I | 0.13 + 0.01 | 63* |
| Test B.1.2.e) | | |
| Carboxamide compound of formula I | 0.01 | 30 |
| Thiacloprid | 0.2 | 37 |
| Thiacloprid + Carboxamide compound of formula I | 0.2 + 0.01 | 70* |

*synergistic control effect according to Colby's equation

Test B.1.3 Control of Black Cutworm (*Agrotis ipsilon*)

For evaluating control of black cutworm (*Agrotis ipsilon*) through direct contact method, the individual insects were dipped directly into compound solution.

The compounds or mixtures were dissolved in acetone at different concentrations. The compounds or mixtures were formulated using a solution containing 50% (v/v) acetone in water with 0.02 wt % Kinetic®. For experimental mixtures, identical volumes of both mixing partners were mixed together to achieve the desired respective concentrations. Second-instar black cutworms were dipped directly into solution for three seconds and then allowed to air dry on filter paper. One treated black cutworm larva was infested into each 16-cm² cell of a 32-cell rearing tray along with the excised shoot of a corn plant and a moistened cotton wick. Cells were then covered with adhesive bio-assay tray lids. Each cell was a replicate and replication was 16x. After infestation, the test was maintained in an incubator at 25.5±1° C. and a 14L:10D light cycle. Mortality (dead+moribund insects) was evaluated 1 and 5 days after treatment (DAT) and mean percent mortality was calculated relative to the untreated control. The results are listed in table B.1.3.

TABLE B.1.3

| Agrotis ipsilon | concentration [ppm] | Average Control % 1 DAT | Average Control % 5 DAT |
|---|---|---|---|
| Test B.1.3.a) | | | |
| Carboxamide compound of formula I | 3 | 38 | 44 |
| Fipronil | 300 | 13 | 31 |
| Fipronil + v | 300 + 3 | 81* | 81* |

*synergistic control effect according to Colby's equation

Test B.1.4 Control of Seedcorn Maggot (*Della platura*)

For evaluating control of seedcorn maggot (*Della platura*) through maximum exposure, the insects were exposed to treated soil.

The compounds or mixtures were first dissolved in acetone, and then mixed with soil to obtain the desired different ppm concentrations (w/w) of compound/soil or mixture/soil. For experimental mixtures, identical volumes of both mixing partners were mixed together to achieve the desired respective concentrations. Treatments were applied in solution to dry, sifted (#10 sieve) play sand in a glass jar. Treatments were thoroughly incorporated by capping and shaking each jar by hand and allowing the solution to soak through the sand mass for at least 10 minutes. The jars were then uncapped and the sand was kept in a fume hood for 4 hours to evaporate the solvent.

After the sand was dry, 10 cm$^3$ of the treated sand was dispensed into a 1-oz. plastic cup with bone meal in the bottom as a food source. Each cup was moistened with 4 ml water, infested with five seedcorn maggot second-instar larvae, and covered. Each cup was a replicate and replication was 5×. The test was maintained in an incubator at 22±1° C. in the dark. Mortality (dead+moribund insects) was evaluated 2 days after treatment (DAT) and mean percent mortality was calculated relative to the untreated control. The results are listed in table B.1.4.

TABLE B.1.4

| Della platura | concentration [ppm compound or mixture/soil] | Average Control % |
|---|---|---|
| Test B.1.4.a) | | |
| Carboxamide compound of formula I | 0.06 | 21 |
| Cyantraniliprole | 10 | 64 |
| Cyantraniliprole + Carboxamide compound of formula I | 10 + 0.06 | 96* |
| Test B.1.4.b) | | |
| V | 0.06 | 21 |
| Imidacloprid | 3 | 18 |
| Imidacloprid + Carboxamide compound of formula I | 3 + 0.06 | 52* |

*synergistic control effect according to Colby's equation

Test B.1.5 Control of Root-Knot Nematodes (*Meloidogyne* spp.)

For evaluating control of root-knot nematodes (*Meloidogyne* spp.) through exposure via drench application, the nematodes were introduced to treated cucumber plants.

The compounds or mixtures were dissolved in acetone at different concentrations. The compounds or mixtures were formulated using a solution containing 50% (v/v) acetone in water with 0.02 wt % Kinetic®. For experimental mixtures, identical volumes of both mixing partners were mixed together to achieve the desired respective concentrations.

Germinated cucumber seeds were planted in 1-oz black plastic cups (one seed per cup) with dry, sifted (#10 sieve) play sand. Treatments were applied as a drench in 7 ml solution to each cup which were held in a fume hood for 1 hour to allow acetone to evaporate. The cups were moved to an environmental chamber (25±2° C., 24 L) and watered daily for the duration of the test. Each cup was a replicate and replication was 5×. At the cucumber's cotyledon stage, each cup was infested with 500 root-knot nematode juveniles (J2s) in 1 ml distilled water.

Four weeks after infestation, cucumber roots were washed off and galls and egg masses were counted. Control was calculated as the reduction in galls or egg masses relative to the untreated control. Mean percent control was calculated for each treatment. The results are listed in table B.1.5.

TABLE B.1.5

| Della platura | concentration [mg compound or mixture/plant] | Average Gall Control % | Average Egg Mass Control % |
|---|---|---|---|
| Test B.1.5.a) | | | |
| Carboxamide compound of formula I | 0.3 | 35 | −21 |
| Abamectin | 0.017 | 40 | 39 |
| Abamectin + Carboxamide compound of formula I | 0.017 + 0.3 | 99* | 100* |
| Test B.1.5.b) | | | |
| Carboxamide compound of formula I | 0.3 | 35 | −21 |
| Abamectin | 0.008 | 24 | 17 |
| Abamectin + Carboxamide compound of formula I | 0.008 + 0.3 | 100* | 99* |

*synergistic control effect according to Colby's equation

Further examples of assays with which the control of soil infesting pests may be evaluated are described in the following.

BP.1.1 Assays for Spider Mites (*Tetranychus*)

Test BP.1.2 Soil Drench Assay in Lima Bean

Test solution comprising a compound of the present invention is prepared at desired concentration using water and an organic solvent. Potted lima been plants are treated with test solution by means of soil drenching. The test compounds are applied as a soil drench in 2 ml of solution at the rate of 4 mg active ingredient/plant (2 mg/ml). Technical material is dissolved in acetone, and distilled water was added to achieve a final concentration of 5% acetone. Four days after treatment, a mixed population of two spotted spider mites (*Tetranychus urticae*) is released onto the leaves. After infestation, plants are kept on a light cart in the laboratory and top watered daily.

Five days after the release of spider mites, the acaricidal efficacy is measured by means of the rating of the damage caused by spider mites or the spider mite mortality: the number of TSSM are counted on plants, percent damage as lesions is visually assessed and means are calculated for each treatment. Mean percent population reduction relative to the solvent blank control is calculated. Mean percent reduction in damage relative to the solvent blank is calculated as 100−(Mean % lesions in treatment/Mean % lesions in Solvent blank)*100.

Test BP.1.3 Seed Treatment Assay in Cotton

Test solution comprising a compound of the present invention is prepared at desired concentration using water and an organic solvent. Cotton seeds are coated with such prepared test solution at the rate 0.5 mg active ingredient/seed and sown to the pots. After plant emergence, a mixed population of two spotted spider mites is released onto the leaves.

Four days after the release of spider mites, the acaricidal efficacy is measured by means of the rating of the damage caused by spider mites or the spider mite mortality: percent damage as lesions was visually assessed and means are calculated for each treatment. Mean percent reduction in damage relative to the solvent blank is calculated as 100−(Mean % lesions in treatment/Mean % lesions in Solvent blank)*100.

Test BP.1.4 Seed Treatment Assay in Cucumber

Test solution comprising a compound of the present invention is prepared at desired concentration using water and acetone as organic solvent. Cucumber seeds are coated with such prepared test solution applied at the rate of 0.5 mg active ingredient/seed and sown to the pots. After plant emergence (eleven days after treatment & planting), a mixed population of two spotted spider mites is released onto the leaves.

Four days after the release of spider mites, the acaricidal efficacy is measured by means of the rating of the damage caused by spider mites.

Percent damage as lesions is visually assessed, and means are calculated for each treatment.

Mean percent damage reduction relative to the olvent blank is calculated as 100−(mean % lesions in treatment/mean % lesions in Solvent blank)*100.

BP.1.5 Assays for Nematode (*Meloidogyne*)

Test B.2.1 Tomato Soil Drench Against Root-Knot Nematode Juveniles

Tomatoes are grown in potting soil until the approximate first true leaf stage (about 2 weeks after planting). Tomatoes are transplanted into play sand. Seven days after transplant, technical material of test compound is dissolved in acetone, and then water is added to achieve a final concentration of 50% acetone. 1 mL of solution is pipetted onto the tomato root zone. One day after treatment (DAT), each pot is infested with about 500 root-knot nematode (*Meliodogyne* spp.) juveniles in 1 ml distilled water. Immediately after infestation, plants are placed in the greenhouse. Plants are top watered and fertilized daily. At 14 DAT, the tomato roots are rinsed off, and the number of galls is counted. Replication is 5-times.

B.2 Control of Phytopathological Fungi

With regard to the control of phytopathological fungi affecting plant propagation material, especially seeds, the following test systems and results demonstrate the fungicidal activity of the carboxamide compound of formula I alone, and its synergistic fungicidal activity in combination with other fungicidal active ingredients.

Microtests for the evaluation of fungicidal activity

The active compounds were formulated separately as a stock solution having a concentration of 10,000 ppm in dimethyl sulfoxide.

B.2.1. Activity Against Rice Blast Pyricu/Aria *Oryzae*

The stock solutions were mixed according to the indicated ratio, pipetted onto a micro titer plate (MTP) and diluted with water to the stated concentrations. A spore suspension of *Pyricularia oryzae* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. The results are given in table B.2.1 hereinbelow.

TABLE B.2.1.

*Pyricularia olyzae*

| Active compound/ active compounds in mixture | Concentration (ppm) | Mixture (ratio) | Observed efficacy | Calculated efficacy according to Colby (%) | Synergism (%) |
|---|---|---|---|---|---|
| carboxamide compound of formula I | 16 | — | 4 | | |
| | 4 | — | 15 | | |
| | 1 | — | 12 | | |
| | 0.063 | — | 2 | | |
| Epoxiconazol | 0.25 | — | 28 | | |
| | 0.063 | — | 1 | | |
| carboxamide compound of formula I | 16 | 64:1 | 100 | 31 | 69 |
| Epoxiconazol | 0.25 | | | | |
| carboxamide compound of formula I | 4 | 63:1 | 100 | 15 | 85 |
| Epoxiconazol | 0.063 | | | | |
| carboxamide compound of formula I | 4 | 16:1 | 100 | 39 | 61 |
| Epoxiconazol | 0.25 | | | | |
| carboxamide compound of formula I | 1 | 16:1 | 100 | 13 | 87 |
| Epoxiconazol | 0.063 | | | | |

B.2.2. Activity Against Early Blight Caused by *Alternaria solani*

The stock solutions were mixed according to the indicated ratio, pipetted onto a micro titer plate (MTP) and diluted with water to the stated concentrations. A spore suspension of *Alternaria solani* in an aqueous biomalt or yeast-bacto-peptone-glycerine solution was then added. The plates were placed in a water vapor-saturated chamber at a temperature of 18° C. Using an absorption photometer, the MTPs were measured at 405 nm 7 days after the inoculation. The results are given in table B.2.2 hereinbelow.

TABLE B.2.2.

*Alternaria solani*

| Active compound/ active compounds in mixture | Concentration (ppm) | Mixture (ratio) | Observed efficacy | Calculated efficacy according to Colby (%) | Synergism (%) |
|---|---|---|---|---|---|
| carboxamide compound of formula I | 63 | — | 0 | | |
| | 16 | — | 0 | | |
| | 4 | — | 0 | | |
| | 1 | — | 0 | | |
| Pyraclostrobin | 0.063 | — | 12 | | |
| | 0.016 | — | 0 | | |
| Triticonazol | 1 | — | 23 | | |
| | 0.25 | — | 0 | | |
| carboxamide compound of formula I | 16 | 254:1 | 36 | 12 | 24 |
| Pyraclostrobin | 0.063 | | | | |
| carboxamide compound of formula I | 63 | 1000:1 | 40 | 12 | 28 |
| Pyraclostrobin | 0.063 | | | | |
| carboxamide compound of formula I | 63 | 4000:1 | 24 | 0 | 24 |

TABLE B.2.2.-continued

Alternaria solani

| Active compound/ active compounds in mixture | Concentration (ppm) | Mixture (ratio) | Observed efficacy | Calculated efficacy according to Colby (%) | Synergism (%) |
|---|---|---|---|---|---|
| Pyraclostrobin | 0.016 | | | | |
| carboxamide compound of formula I | 63 | 63:1 | 43 | 23 | 20 |
| Triticonazol | 1 | | | | |
| carboxamide compound of formula I | 16 | 64:1 | 32 | 0 | 32 |
| Triticonazol | 0.25 | | | | |
| carboxamide compound of formula I | 4 | 16:1 | 20 | 0 | 20 |
| Triticonazol | 0.25 | | | | |
| carboxamide compound of formula I | 4 | 4:1 | 52 | 23 | 29 |
| Triticonazol | 1 | | | | |
| carboxamide compound of formula I | 1 | 4:1 | 34 | 0 | 34 |
| Triticonazol | 0.25 | | | | |

B.2.3. Activity Against *Microdochium nivale*

The stock solutions were mixed according to the indicated ratio, pipetted onto a micro titer plate (MTP) and diluted with water to the stated concentrations. A spore suspension of *Microdochium nivale* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. The results are given in table B.2.3 hereinbelow.

TABLE B.2.3

Microdochium nivale

| Active compound/ active compounds in mixture | Concentration (ppm) | Mixture (ratio) | Observed efficacy | Calculated efficacy according to Colby (%) | Synergism (%) |
|---|---|---|---|---|---|
| carboxamide compound of formula I | 63 | — | 4 | | |
| | 16 | — | 15 | | |
| | 4 | — | 13 | | |
| Pyraclostrobin | 0.016 | — | 46 | | |
| Fluxapyroxad | 0.063 | — | 0 | | |
| | 0.004 | — | 0 | | |
| Epoxiconazol | 0.016 | — | 29 | | |
| | 0.004 | — | 8 | | |
| carboxamide compound of formula I | 4 | 250:1 | 79 | 53 | 26 |
| Pyraclostrobin | 0.016 | | | | |
| carboxamide compound of formula I | 16 | 1000:1 | 74 | 54 | 20 |
| Pyraclostrobin | 0.016 | | | | |
| carboxamide compound of formula I | 63 | 4000:1 | 93 | 48 | 45 |
| Pyraclostrobin | 0.016 | | | | |
| carboxamide compound of formula I | 63 | 1000:1 | 35 | 4 | 31 |
| Fluxapyroxad | 0.063 | | | | |
| carboxamide compound of formula I | 63 | 16000:1 | 25 | 4 | 21 |
| Fluxapyroxad | 0.004 | | | | |
| carboxamide compound of formula I | 4 | 250:1 | 63 | 38 | 25 |
| Epoxiconazol | 0.016 | | | | |
| carboxamide compound of formula I | 63 | 4000:1 | 99 | 31 | 68 |
| Epoxiconazol | 0.016 | | | | |
| carboxamide compound of formula I | 16 | 4000:1 | 99 | 21 | 78 |
| Epoxiconazol | 0.004 | | | | |

B.2.4. Activity Against *Rhizoctonia solani*

The stock solutions were mixed according to the indicated ratio, pipetted onto a micro titer plate (MTP) and diluted with water to the stated concentrations. A spore suspension of *Rhizoctonia solani* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. The results are given in table B.2.4 hereinbelow.

TABLE B.2.4

*Rhizoctonia solani*

| Active compound/active compounds in mixture | Concentration (ppm) | Mixture (ratio) | Observed efficacy | Calculated efficacy according to Colby (%) | Synergism (%) |
|---|---|---|---|---|---|
| carboxamide compound of formula I | 16 | — | 0 | | |
| | 4 | — | 0 | | |
| | 1 | — | 0 | | |
| Epoxiconazol | 0.016 | — | 24 | | |
| | 0.004 | — | 0 | | |
| | 0.001 | — | 0 | | |
| Triticonazol | 0.25 | — | 41 | | |
| carboxamide compound of formula I | 4 | 250:1 | 55 | 24 | 31 |
| Epoxiconazol | 0.016 | | | | |
| carboxamide compound of formula I | 63 | 4000:1 | 96 | 31 | 65 |
| Epoxiconazol | 0.016 | | | | |
| carboxamide compound of formula I | 16 | 4000:1 | 75 | 0 | 75 |
| Epoxiconazol | 0.004 | | | | |
| carboxamide compound of formula I | 4 | 4000:1 | 20 | 0 | 20 |
| Epoxiconazol | 0.001 | | | | |
| carboxamide compound of formula I | 1 | 63:1 | 44 | 24 | 20 |
| Epoxiconazol | 0.016 | | | | |
| carboxamide compound of formula I | 16 | 64:1 | 67 | 41 | 26 |
| Triticonazol | 0.25 | | | | |
| carboxamide compound of formula I | 4 | 16:1 | 67 | 41 | 26 |
| Triticonazol | 0.25 | | | | |
| carboxamide compound of formula I | 1 | 4:1 | 69 | 41 | 28 |
| Triticonazol | 0.25 | | | | |

The measured parameters were compared to the growth of the active compound-free control variant (100%) and the fungus-free and active compound-free blank value to determine the relative growth in % of the pathogens in the respective active compounds.

These percentages were converted into efficacies.

As mentioned above, the expected efficacies of active compound mixtures were determined using Colby's formula [R. S. Colby, "Calculating synergistic and antagonistic responses of herbicide combinations", Weeds 15, 20-22 (1967)] and compared with the observed efficacies.

The invention claimed is:

1. A method for controlling or combating animal pests in soil or plant propagation material comprising applying directly or indirectly to the plant or to plant propagation material by drenching the soil, by drip application onto the soil, by soil injection, by dipping or by treatment of seeds, a composition comprising an agriculturally active compound of formula (I):

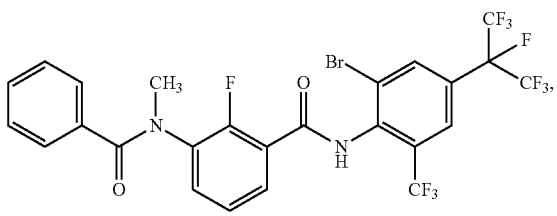

or a tautomer, an enantiomer, a diastereomer or a salt thereof,
wherein the compound of formula (I) is combined with, or is applied together with, fluxapyroxad
wherein the compound of formula (I) and fluxapyroxad are present in a weight ratio of 1000:1 to 16000:1.

2. The method of claim 1, wherein the plant or the plant propagation material to be treated is grown in an artificial growth substrate.

3. The method of claim 2, wherein the artificial growth substrate is selected from rock wool, glass wool, quartz sand, gravel, expanded clay and vermiculite.

4. The method of claim 1, wherein the plant or plant propagation material to be treated is planted or growing in a closed system.

5. The method of claim 1, wherein the compound of formula (I) is applied by drip irrigation.

6. The method of claim 1, wherein the compound of formula (I) is applied with drip application systems.

7. The method of claim 1, wherein the compound of formula (I) is applied by soil injection.

8. A method for protection of plant propagation material comprising contacting the plant propagation material with a pesticidally effective composition comprising an agriculturally active compound of formula (I):

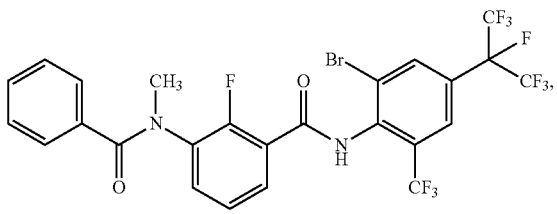

or a tautomer, an enantiomer, a diastereomer or a salt thereof,
wherein the compound of formula (I) is combined with, or is applied together with, fluxapyroxad wherein the compound of formula (I) and fluxapyroxad are present in a weight ratio of 1000:1 to 16000:1;
and wherein the plant propagation material are seeds of transgenic plant.

9. A method according to claim 8, wherein the compound(s) is applied in an amount of from 0.1 g to 100 kg per 100 kg of plant propagation material.

10. A method according to claim 8, wherein the plant roots and shoots resulting from the treated seeds are protected.

11. A method according to claim 8, wherein the active compound(s) is/are applied by drenching the soil.

12. A method according to claim 8, wherein the active compound(s) is/are applied by drip irrigation.

13. A method according to claim 8, wherein the active compound(s) is/are applied by soil injection.

14. A method according to claim 8, wherein the active compound(s) is/are applied with drip application systems.

15. A method according to claim 8, wherein the active compound(s) is/are used in in-furrow applications.

16. A method according to claim 8 wherein the active compound(s) is/are used in T-Band applications.

17. Seed treated with a composition comprising an agriculturally active compound of formula (I):

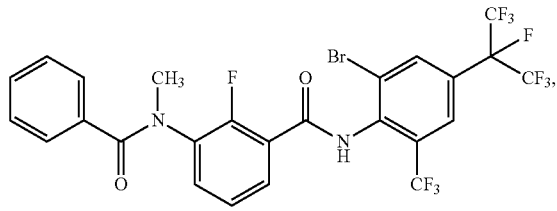

(I)

or a tautomer, an enantiomer, a diastereomer or a salt thereof, and fluxapyroxad wherein the compound of formula (I) and fluxapyroxad are present in a weight ratio of 1000:1 to 16000:1, in an amount of from 0.1 g to 10 kg per 100 kg of seeds.

* * * * *